(12) United States Patent
Van Der Boom et al.

(10) Patent No.: US 9,847,494 B2
(45) Date of Patent: Dec. 19, 2017

(54) METAL-BASED TRIS-BIPYRIDYL COMPLEXES AND USES THEREOF IN ELECTROCHROMIC APPLICATIONS

(71) Applicant: YEDA RESEARCH AND DEVELOPMENT CO. LTD., Rehovot (IL)

(72) Inventors: Milko E. Van Der Boom, Rishon Lezion (IL); Michal Lahav, Rehovot (IL); Sreejith Shankar Pooppanal, Rehovot (IL)

(73) Assignee: YEDA RESEARCH AND DEVELOPMENT CO. LTD., Rehovot (IL)

( * ) Notice: Subject to any disclaimer, the term of this patent is extended or adjusted under 35 U.S.C. 154(b) by 0 days.

(21) Appl. No.: 15/037,406

(22) PCT Filed: Nov. 19, 2014

(86) PCT No.: PCT/IL2014/051005
§ 371 (c)(1),
(2) Date: May 18, 2016

(87) PCT Pub. No.: WO2015/075714
PCT Pub. Date: May 28, 2015

(65) Prior Publication Data

US 2016/0293860 A1    Oct. 6, 2016

Related U.S. Application Data

(60) Provisional application No. 61/906,565, filed on Nov. 20, 2013.

(30) Foreign Application Priority Data

Nov. 20, 2013 (IL) .......................... 229525

(51) Int. Cl.
*H01L 51/00* (2006.01)
*B82Y 10/00* (2011.01)
(Continued)

(52) U.S. Cl.
CPC .......... *H01L 51/0083* (2013.01); *B82Y 10/00* (2013.01); *C07D 401/06* (2013.01);
(Continued)

(58) Field of Classification Search
CPC .............................. C07D 401/06; G11C 11/56
See application file for complete search history.

(56) References Cited

U.S. PATENT DOCUMENTS 5,009,958 A    4/1991 Yamashita et al.
5,818,636 A    10/1998 Leventis et al.
(Continued)

FOREIGN PATENT DOCUMENTS

JP    S63-247731 A    10/1988
WO    WO 86/02734    5/1986
(Continued)

OTHER PUBLICATIONS

Coe et al., J'nal of the ACS, vol. 127, (38), pp. 13399-13410 (2005).*

(Continued)

*Primary Examiner* — Paul V Ward
(74) *Attorney, Agent, or Firm* — Mark S. Cohen; Pearl Cohen Zedek Latzer Baratz LLP

(57) ABSTRACT

The present invention relates to metal-based tris-bipyridyl complexes, e.g., iron-based tris-bipyridyl complexes, and their use in fabrication of surface confined assemblies for electrochromic applications. Formulae I and II.

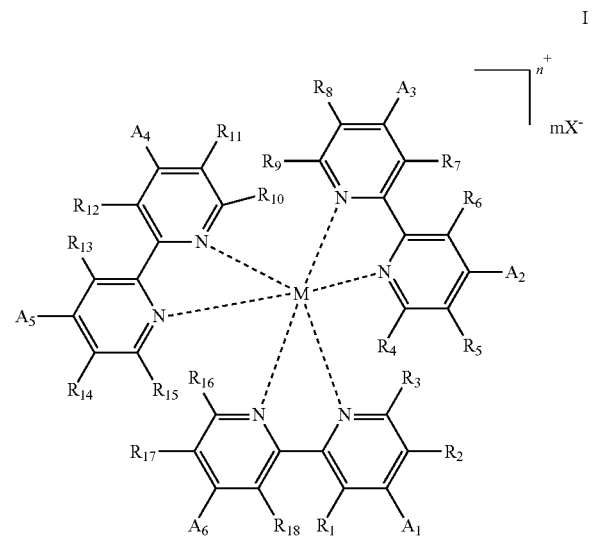

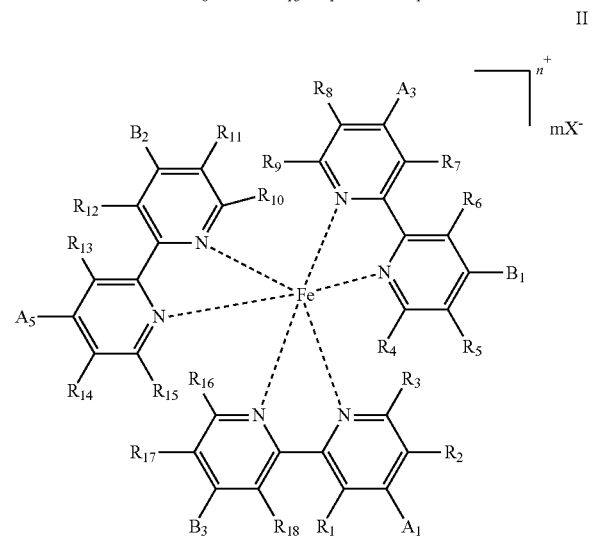

40 Claims, 46 Drawing Sheets

(51) Int. Cl.

| | | |
|---|---|---|
| C07D 401/06 | (2006.01) | |
| C07D 403/06 | (2006.01) | |
| C07F 15/02 | (2006.01) | |
| G02F 1/15 | (2006.01) | |
| G11C 7/00 | (2006.01) | |
| C09B 57/10 | (2006.01) | |
| G11C 13/00 | (2006.01) | |
| H01L 51/05 | (2006.01) | |

(52) U.S. Cl.
CPC .......... *C07D 403/06* (2013.01); *C07F 15/025* (2013.01); *C09B 57/10* (2013.01); *G02F 1/15* (2013.01); *G11C 7/00* (2013.01); *G02F 2001/1502* (2013.01); *G02F 2001/1515* (2013.01); *G11C 13/0014* (2013.01); *H01L 51/0595* (2013.01)

(56) References Cited

U.S. PATENT DOCUMENTS

| | | | |
|---|---|---|---|
| 6,198,655 | B1 | 3/2001 | Heath et al. |
| 6,208,553 | B1 | 3/2001 | Gryko et al. |
| 6,212,093 | B1 | 4/2001 | Lindsey |
| 6,426,827 | B1 | 7/2002 | Bonhote et al. |
| 6,728,129 | B2 | 4/2004 | Lindsey et al. |
| 6,824,837 | B2 | 11/2004 | Abbott et al. |
| 8,722,879 | B2 | 5/2014 | Van Der Boom |
| 8,865,890 | B2 | 10/2014 | Van Der Boom |
| 2004/0159835 | A1 | 8/2004 | Krieger et al. |
| 2004/0175631 | A1 | 9/2004 | Crocker et al. |
| 2005/0207208 | A1 | 9/2005 | Bocian et al. |
| 2005/0232000 | A1 | 10/2005 | Lindsey |
| 2005/0243597 | A1 | 11/2005 | Gallo et al. |
| 2006/0092687 | A1 | 5/2006 | Kuhr et al. |
| 2006/0209587 | A1 | 9/2006 | Bocian et al. |
| 2007/0258147 | A1 | 11/2007 | Van der Boom et al. |
| 2008/0219041 | A1 | 9/2008 | Kuhr et al. |
| 2010/0006794 | A1 | 1/2010 | Hawkins et al. |
| 2010/0118598 | A1 | 5/2010 | Hawkins et al. |

FOREIGN PATENT DOCUMENTS

| | | |
|---|---|---|
| WO | WO 93/12256 | 6/1993 |
| WO | WO 95/08644 A1 | 3/1995 |
| WO | WO 96/40978 | 12/1996 |
| WO | WO 01/03126 A2 | 1/2001 |
| WO | WO 01/52266 A1 | 7/2001 |
| WO | WO 02/10852 | 2/2002 |
| WO | WO 03/038886 A1 | 5/2003 |
| WO | WO 2006/085319 A2 | 8/2006 |
| WO | WO 2009/095924 A1 | 8/2009 |
| WO | WO 2011/141913 A1 | 11/2011 |
| WO | WO 2014/009952 A2 | 1/2014 |
| WO | WO 2014/061018 A2 | 4/2014 |

OTHER PUBLICATIONS

Coe et al. Journal of the American Chemical Society (2010), 132(10), 3496-3513.*
Graham et al., Proceeedings of SPI, vol. 8725, pp. 872509 (2013).*
Altman et al. "Controlling structure from the bottom-up: structural and optical properties of layer-by-layer assembled palladium coordination-based muitilayers" Journal of the American Chemical Society. Jun. 7, 2006;128(22):7374-82.
Altman et al. "Designing Surface-Confined Coordination Oligorriers" Chemistry—A European Journal. Jun. 18, 2010;16(248744-7.
Altman et al. "Molecular assembly of a 3D-ordered multilayer" Journal of the American Chemical Society. Mar. 26, 2008;130(15):5040-1.
Andres et al. "Inkjet deposition of layer-by-layer assembled films" Journal of the American Chemical Society. Sep. 23, 2010;132(41):14496-502.

Ariga et al. "Chailenges and breakthroughs in recent research on self-assembly" Science and Technology of Advanced Materials. 2008 9 014109.
Beaujuge et al. "The donor—acceptor approach allows a black-to-transmissive switching polymeric electrochrorrie" Nature materials. Oct. 1, 2008;7(10):795-9.
Beley et al. "Luminescent dinuclear complexes containing ruthenium (II)-and osmium (II)-terpyridine-type chromophores bridged by a rigid biscyciometalating ligand" Inorganic Chemistry. Jun. 1994;33(12):2543-7.
Börje et al. "A new bridging ligand for the synthesis of luminescent polynuclear Ru (II) and Os (II) polypyridine complexes" New Journal of Chemistry. 2001;25(2):'191-3.
Braga et al. "Rates of electron transfer from osmium (II) to iron (III) complex ions containing 2, 2'-bipyridine or its derivatives as ligands. Effects of electrolytes at low concentrations and reactant-separation distance" The Journal of Physical Chemistry. Dec. 1985;89(26):5822-8.
Braterman et al. "Electronic absorption spectra of The iron (II) complexes of 2, 2'-bipyridine, 2, 2'-bipyrimidine, 1, 10-phenanthroline, and 2, 2': 6', 2"-terpyridine and their reduction products" Inorganic Chemistry. Feb. 1992;31(4).555-9.
Carroll et al. "The genesis of molecular electronics" Angewandte Chemie International Edition. Dec. 2, 2002;41(23):4378-400.
Choudhury et al. "Linear vs exponential formation of molecular-based assemblies" Journal of the American Chemical Society. Jun. 22, 2010;132(27).9295-7.
Coe et al. "Combining very large quadratic and cubic nonlinear optical responses in extended, tris-chelate rnetallochromophores with six π-conjugated pyridinium substituents" Journal of the American CrielllCal Society. Feb. 18, 2010;132(10)3496-513.
Coe et al. "Three-dimensional nonlinear optical chromophores based on metal-to ligand charge-transfer from ruthenium (Ii) or iron (11) centers" Journal of the American Chemical Society, 2005 Sep 28;127(38)13399-410. El.
Collier et al. "A [2] catenane-based solid state electronically reconfigurable switch" Science. Aug. 18, 2000;289(5482):1172-5.
De Ruiter et al. "Sequence-Dependent Assembly to Control Molecular Interface Properties" Angewandte Chemie International Edition. Jan. 7, 2013;52(2).704-9.
De Ruiter et al. "Composite molecular assemblies: Nanoscale structural control and spectroelectrochernical diversity" Journal of the American Chemical Society. Oct. 25, 2013;135(44):16533-44.
De Ruiter et al."Selective optical recognition and quantification of parts per million levels of Cr6+ in aqueous and organic media by immobilized polypyridyl complexes on glass" Journal of the American Chemical Society. Mar. 5, 2008;130(9):2744-5.
De Ruiter et al. "Sequential Logic Operations with Surface-Confined Polypyridyl Complexes Displaying Molecular Random Access Memory Features" Angewandte Chemie International Edition. Jan. 4, 2010;49(1):189-72.
De Ruiter et al. "Sequential logic and random access memory (RAM): A molecular approach" Journal of Materials Chemistry, 2011;21(44):17575-81.
De Ruiter et al. "Electrically Addressable Multistate Volatile Memory with Flip- Flop and Flip- Flap- Flop Logic Circuits on a Solid Support" Angew. Chem. int. Ed. 2010, 49, 4780-4783.
De Ruiter et al. "Poiyrneric memory elements and logic circuits that store multiple bit states" ACS applied materials & interfaces. Nov. 29, 2010;2(12):3578-85.
De Ruiter et al. "Surface-confined assemblies and polymers for molecular logic" Accounts of chemical research. Jun. 16, 2011;44(8):563-73.
De Ruiter et al. "Surface-confined assemblies and polymers for sesing and molecular logic"InSPIE Defense, Security, and Sensing May 29, 2013 (pp. 872509-0872509). International Society for Optics and Photonics.
Desiraju G.R. "Crystal engineering: a holistic view" Angewandte Chemie international Edition. Nov. 12, 2007;46(44):8342-56.
Doherty et al. "Speciation of iron(II) and iron(III) using a dual electrode modified with electrocatalytic polymers" Analytical Chemistry. Mar. 1992;64(5):572-5.

(56) References Cited

OTHER PUBLICATIONS

Evans et al. "Self-assembled monolayers of alkanethiols containing a polar aromatic group: effects of the dipole position on molecular packing, orientation, and surface wetting properties" Journal of the American Chemical Society. May 1991;113(11):4121-31.

Facchetti et al. "Layer-by-layer self-assembled pyrrole-based donor-acceptor chromophores as electro-optic materials" Chemistry of materials. Mar. 11, 2003;15(5):1064-72.

Facchetti et al. "Very large electro-optic response in H-bonded heteroaromatic films grown by phyhsical vapour deposition" Nature materials. Dec. 1, 2004;3(12):910-7.

Fang et al. "A "mix and match" ionic-covalent strategy for self-assembly of inorganic multilayer films" Journal of the American Chemical Society, Dec. 17, 1997;119(50):12184-91.

Finklea et al. "Elecron-transfer kinetics in organized thiol monolayers with attached pentaammine (pyridine) ruthenium redox centers" Journal of the American Chemical Society. Apr. 1992:114(9):3173-81.

Garcia-Canadas et al. "Electrochromic switching in the visible and near IR with a Ru-dioxolene complex adsorbed on a nanocrystalline SnO 2 electrode" Electrochemistry communications. May 31, 2003;5(5):416-20.

Gillaizeau-Gauthier et al. "Phosphonate-based bipyridine dyes for stable photovoltaic devices" Inorganic chemistry. Nov. 5, 2001;40(23):6073-9.

Gupta et al. "Optical sensing of parts per million levels of water in organic solvents using redox-active osmium chromophore-based monolayers" Journal of the American Chemical Society, Jul. 5, 2006;128(26):8400-1.

Handy et al. "Solid-state light-emitting devices based on the tris-chelated ruthenium (II) complex. 2. Tris (bipyridyl) ruthenium (II) as a high-brightness emitter" Journal of the American Chemical Society. Apr. 14, 1999;121 (14).3525-8.

Hoertz et al. "Light-to-chemical energy conversion in lamellar solids and thin films" Inorganic chemistry. Oct. 3, 2005;44(20):6828-40.

international Search Report for PCT Application No. PCT/1L2014/051005 dated Feb. 20, 2015.

Jandrasics et al. "Synthesis and properties of mononuclear tris (heteroleptic) osmium (II) complexes containing bidentate polypyridyl ligands" Journal of the Chemical Society, Dalton Transactions. 1997(2):153-60.

Katz et al. "Polar orientation of dyes in robust multilayers by zirconium phosphate-phosphonate interlayers" Science. Dec. 6, 1991;254(5037):1435-7.

Kim et al. "Noncovaiently Linked Zinc Porphyrin-Ru (bpy)~ 3 Dyad Assembled via Axial Coordination" Bulletin-Korean Chemical Society. Oct. 20, 2003;24(10):1490-4.

Kovtyukhova et al. "Layer-by-layer assembly of rectifying junctions in and on metal nanowires" The Journal of Physical Chemistry B. Sep. 20, 2001;105(37):8762-9.

Lahann et ai. "A reversibly switching surface" Science. Jan. 17, 2003;299(5605):371-4.

Lee et al. "Organosilicate thin film containing Ru (bpy) 3 2+ for an electrogenerated chemiluminescence (ECL) sensor" Chemical Communications. 2003(13):1602-3.

Lee et al. "Adsorption of ordered zirconium phosphonate multilayer films on silicon and gold surfaces" The Journal of Physical Chemistry. 1988 May 1988;92(9):2597-601.

Lee et al. "Inorganic analogs of Langmuir-Biodgett films: Adsorption of ordered zirconium 1, 10-decanebisphosphonate multilayers on silicon surfaces" Journal of the American Chemical Society. Jan. 1988;110(2):618-20.

Li et al. "Capacitance and conductance characterization of ferrocene-containing self- assembled monolayers on silicon surfaces for memory applications" Applied physics letters. Aug. 19, 2002;81(8):1494-6.

Li et al. "Chromophoric sell-assembled multilayers. Organic superlattice approaches to thin-film nonlinear optical materials" Journal of the American Chemical Society. Sep. 1990;112(20):7389-90.

Liu et al. "Molecular memories that survive silicon device processing and real-world operation" Science. Nov. 28, 2003;302(5650):1543-5.

Loi et al. "Supramolecular organization in ultra-thin films of α-sexithiophene on silicon dioxide" Nature materials. Jan. 1, 2005;4(1):81-5.

Maoz et al. "Hydrogen-bonded multilayers of self-assembling silanes: structure elucidation by combined Fourier transform infrared spectroscopy and X-ray scattering techniques" Supramolecular Science. Dec. 31, 1995;2(1):9-24.

Maoz et al. "Self-replicating amphiphilic monolayers" Nature. 1996;384(6605):150-3.

Min et al. "Electrochemical biomernory device consisting of recombinant protein molecules" Biotechnology and Bioprocess Engineering. Feb. 1, 2010;15(1):30-9.

Motiei et al. "Self-propagating assembly of a molecular-based multilayer" Journal of the American Chemical Society. Jun. 24, 2008;130(28):8913-5.

Motiei et al. "Electrochromic behavior of a self-propagating molecular-based assembly" Journal of the American Chemical Society, Feb. 18, 2009;131(10):3468-9.

Motiei et al. "Self-propagating molecular assemblies as intedayers for efficient inverted bulk-heterojunction solar cells" Journal of the American Chemical Society. Aug. 24, 2010;132(36):12528-30.

Motiei et al. "Controlling growth of self-propagating molecular assemblies" Chemical Science. 2012;3(1):66-71.

Motiei et al. "Electrocnernical Characteristics of a Self-Propagating Molecular-Based Assembly" The Journal of Physical Chemistry B. Jan. 20, 2010;114(45):14283-6.

Motiei et al. "Synergism in Multicomponent Self-Propagating Molecular Assemblies" Langmuir. Dec. 3, 2010;27(4):1319-25.

Netzer. et al. "A new approach to construction of artificial monolayer assemblies" Journal ofthe American Chemical Society. Feb. 1983;105(3):674-6.

Nitahara et al. "A photoelectronic switching device using a mixed self-assembled monolayer" The Journal of Physical Chemistry B. Mar. 10, 2005;109(9):3944-8.

Nugent et al. "Porous materials with optimal adsorption thermodynamics and kinetics for CO2 separation" Nature. Mar. 7, 2013;495(7439):80-4.

Oki et al. "An efficient preparation of 4, 4'-dicarboxy-2, 2'-bipyridine" Synthetic; communications. Dec. 1, 1995;25(24):4093-7.

Putvinski, et al., "Self-assembly of organic multilayers with polar order using zirconium Phosphate bonding between layers" Langmuir. Oct. 1990;6(10):1567-71.

Richardson et al. "Spctroelectrochemical sensing based on multimode selectivity simultaneously achievable in a single device. 13. Dectection of aqueous iron by in situ comlexation with 2, 2'-bipyridine" Analytical chemistry. Jul. 15, 2002;74(14):3330-5.

Sagiv J. "Organized monolayers by adsorption. 1. Formation and structure of oleophobic mixed monolayers on solid surfaces" Journal of the American Chemical Society. Jan. 1980;102(1):92-8.

Shinbo et al. "Fabrication and electrochemical properties of layer-by-layer deposited films containing phthalocyanine dyes" Thin Solid Films. Aug. 22, 2003;438:177-81.

Shirman et al. "Assembly of crystalline halogen-bonded materials by physical vapor deposition". Journal of the American Chemical Society, Jun. 5, 2008;130(26):8162-3.

Sortino et al. "Novel self-assembled Monolayers of dipolar ruthenium (III/II) pentaammine (4, 4'-bipyridinium) complexes on ultrathin platinum films as redox molecular switches" Journal of the American Chemical Society, Feb. 5, 2003;125(5)1122-3.

Stalnaker et al. "Electron-transfer between iron, ruthenium, and osmium complexes containing 2, 2'-bipyridyl, 1, 10-phenanthroline, or their derivatives. Effects of electrolytes on rates" The Journal of Physical Chemistry. Apr. 1977;81(7):601-4.

(56) References Cited

OTHER PUBLICATIONS

Thompson et at "Hydrolysis and condensation of self-assembled monolayers of (3-meroaptopropyl) trimethoxysilane on Ag and Au surfaces" Langmuir. Apr. 18, 1997;13(8):2291-302.
Ulman A. "Formation arid structure of self-assembled monolayers" Chemical reviews. Jun. 20, 1996;96(4):1533-54.
Van Der Boom et al. "Nanoscale consecutive self-assembly of thin-film molecular materials for electrooptic switchings. Chemical streamlining and ultrahigh response chromophores" Langmuir. Apr. 30, 2002;18(9):3704-7.
Walsh et al. "Modulation of heterogeneous electron-transfer dynamics across the electrode/monolayer interface" The Journal of Physical Chemistry B. Feb. 26, 2004;108(8).2631-6.
Yang et al. "Growth and characterization of metal (II alkanebisphosphonate multilayer thin films on gold surfaces". Journal of the American Chemical Society. Dec. 1993;115(25):11855-62.
Yasutomi et al. "A molecular photodicAe system that can switch photocurrent direction" Science. Jun 25, 2004;304(5679)1944-7.
Yerushalmi et al. "Stimuli responsive materials: new avenues toward smart organic devices" Journal of Materials Chemistry. 2005;15(42):4480-7.
Yonemoto et al. "Electron-transfer reactions of ruthenium trisbipyridyl-violoc.len donor-acceptor molecules: comparison of the distance dependence of electron transfer-rates in the normal and Marcus inverted regions" Journal of the American Chemical Society. Jun. 1994;116(11):4786-95.

\* cited by examiner

Fig. 1
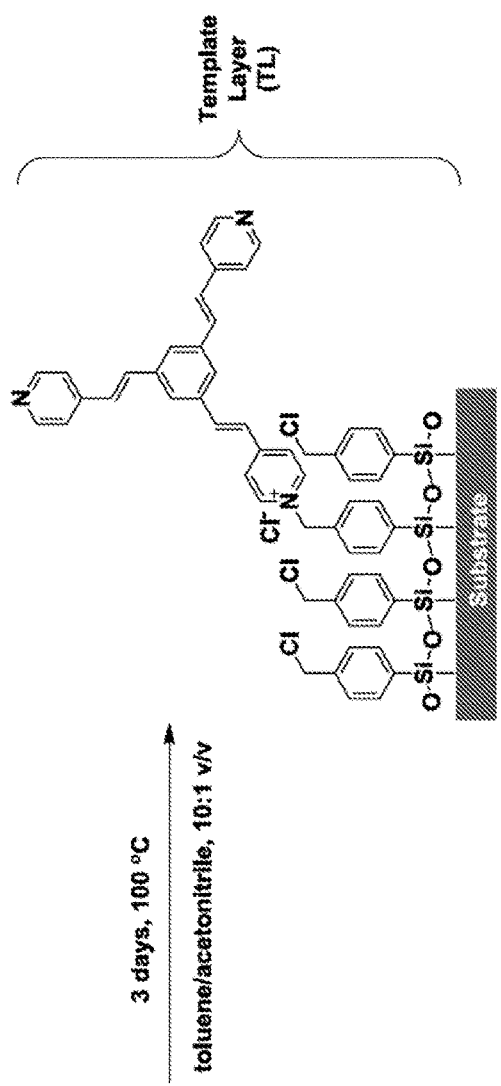
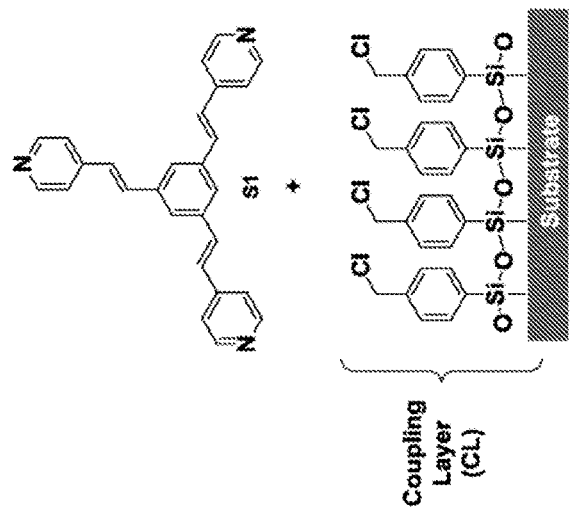

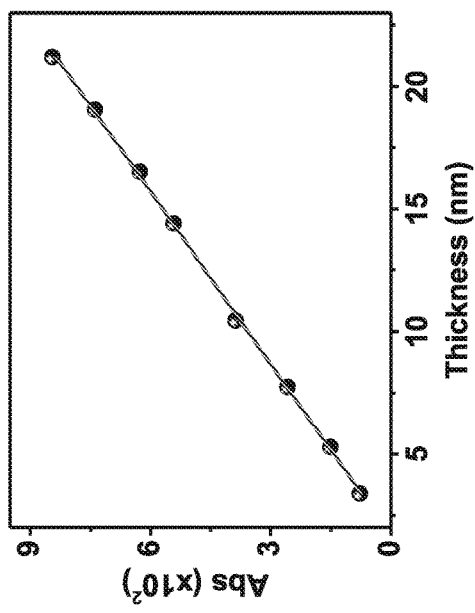
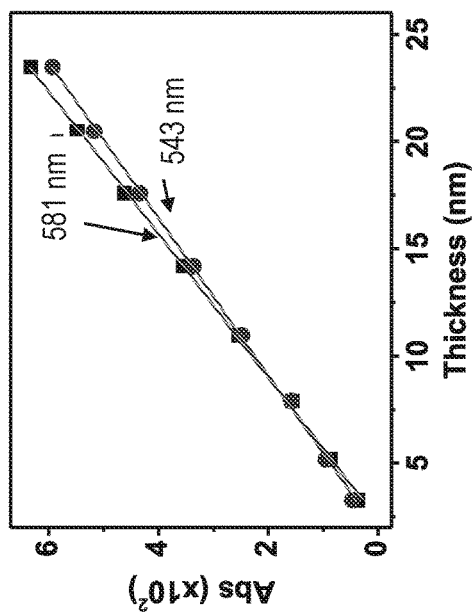
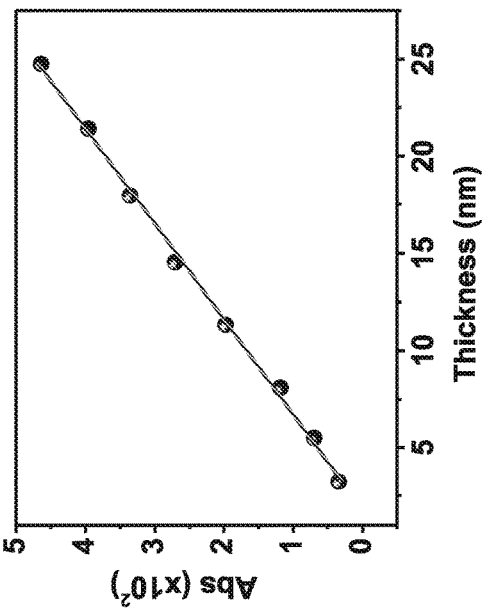
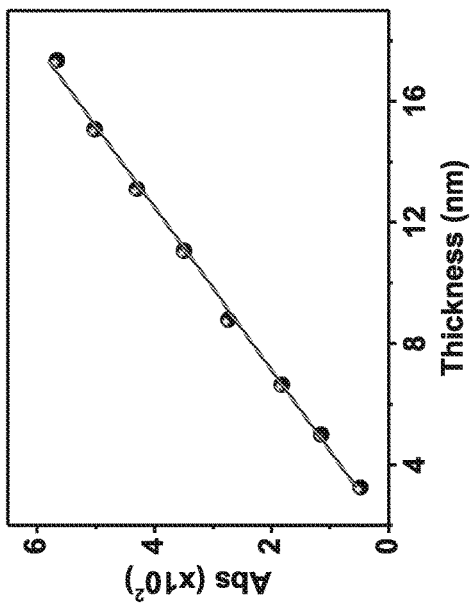

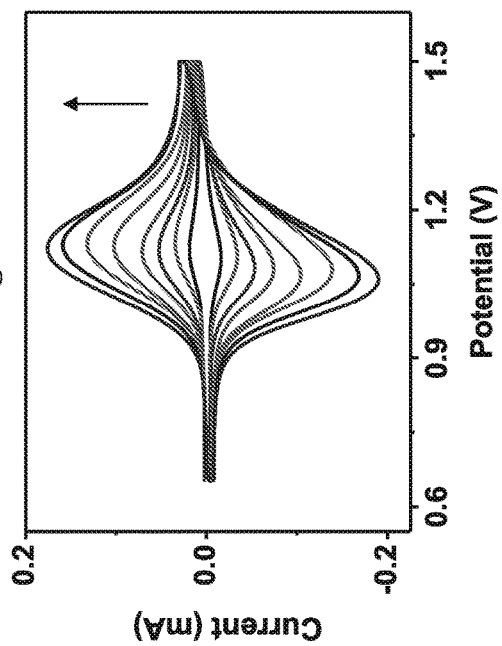
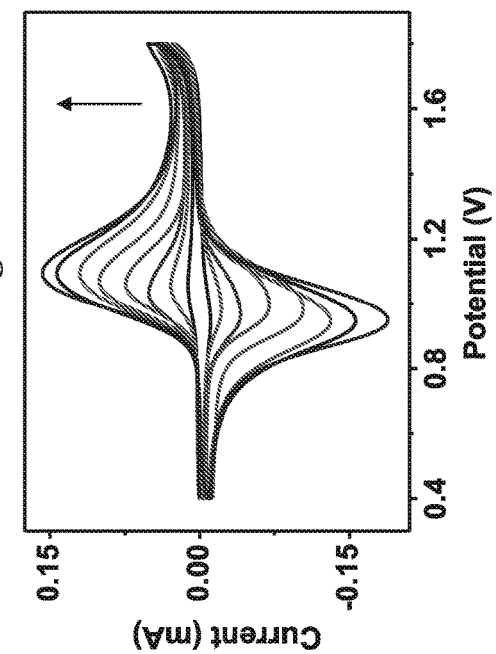
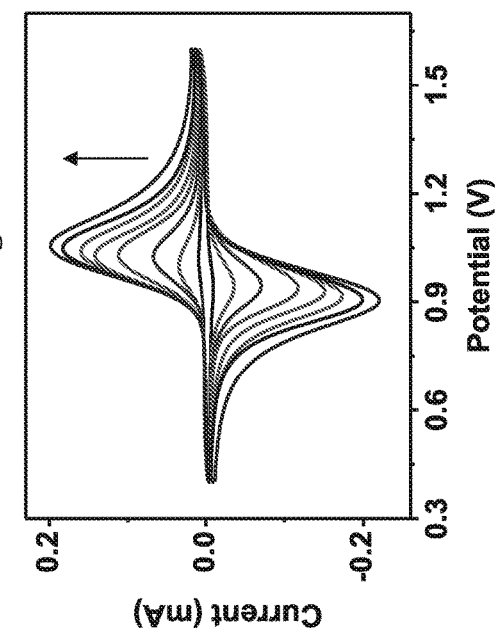
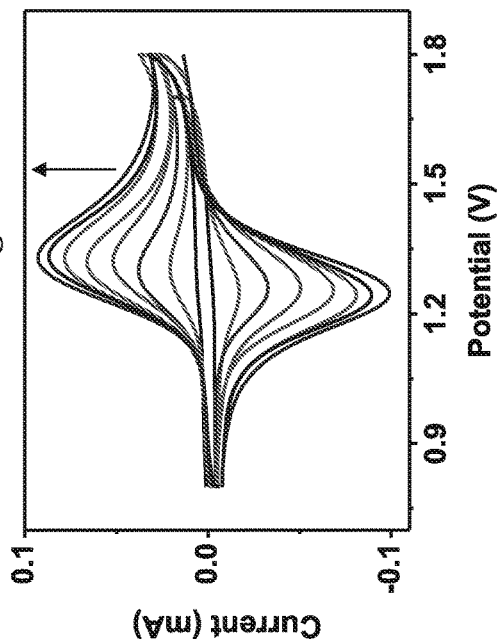

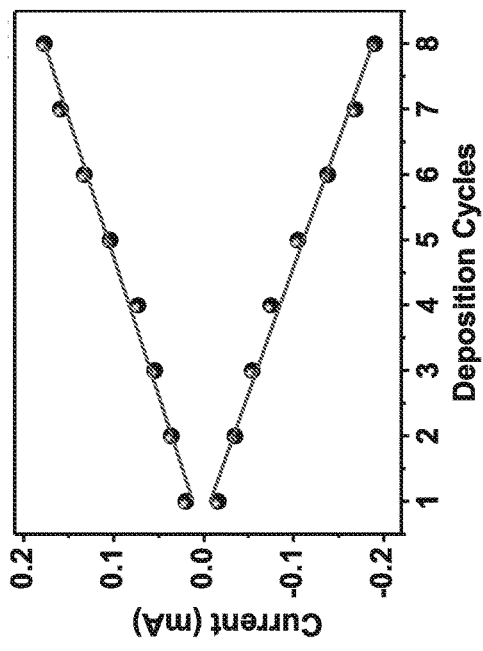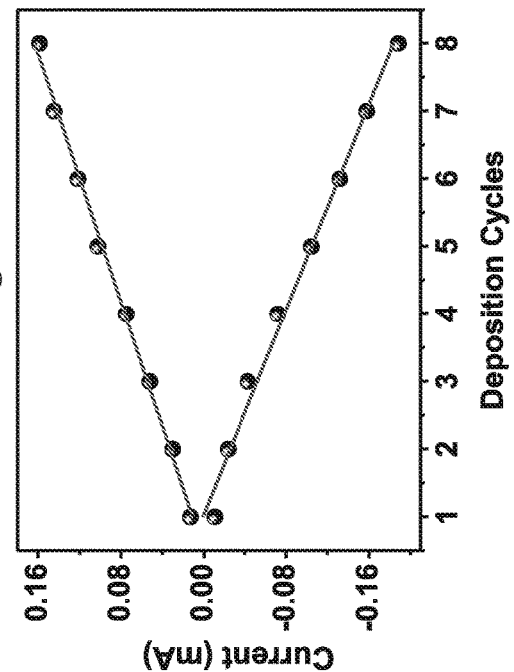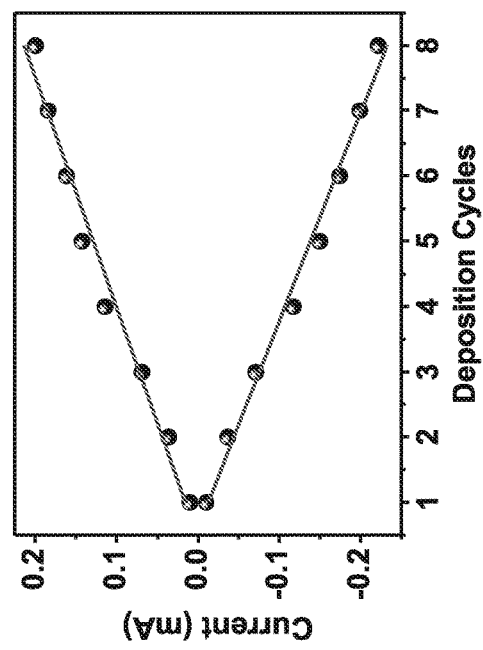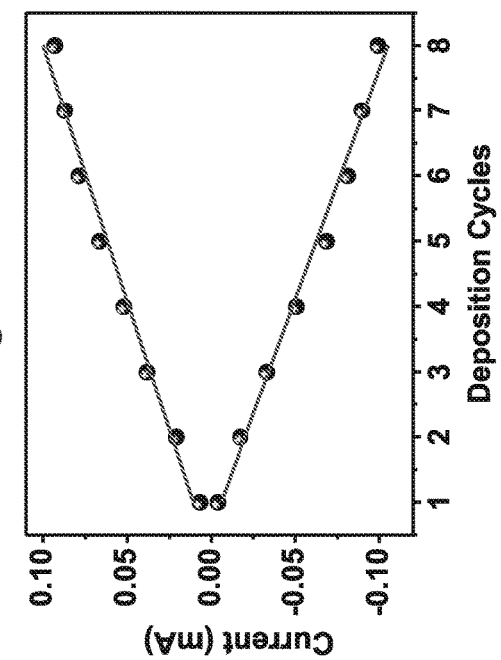

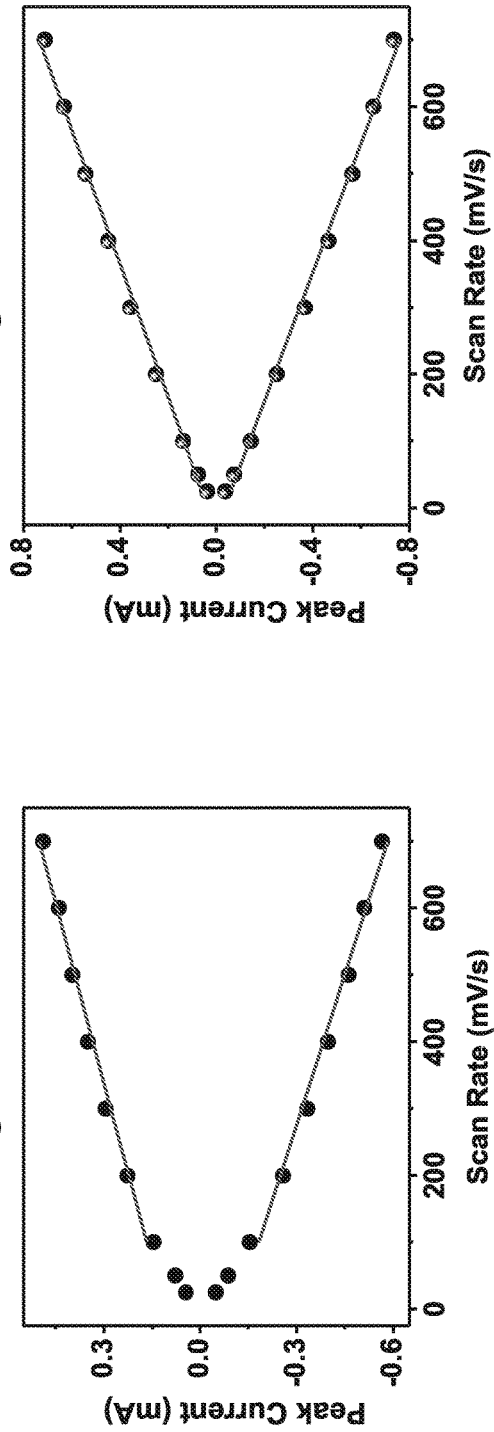
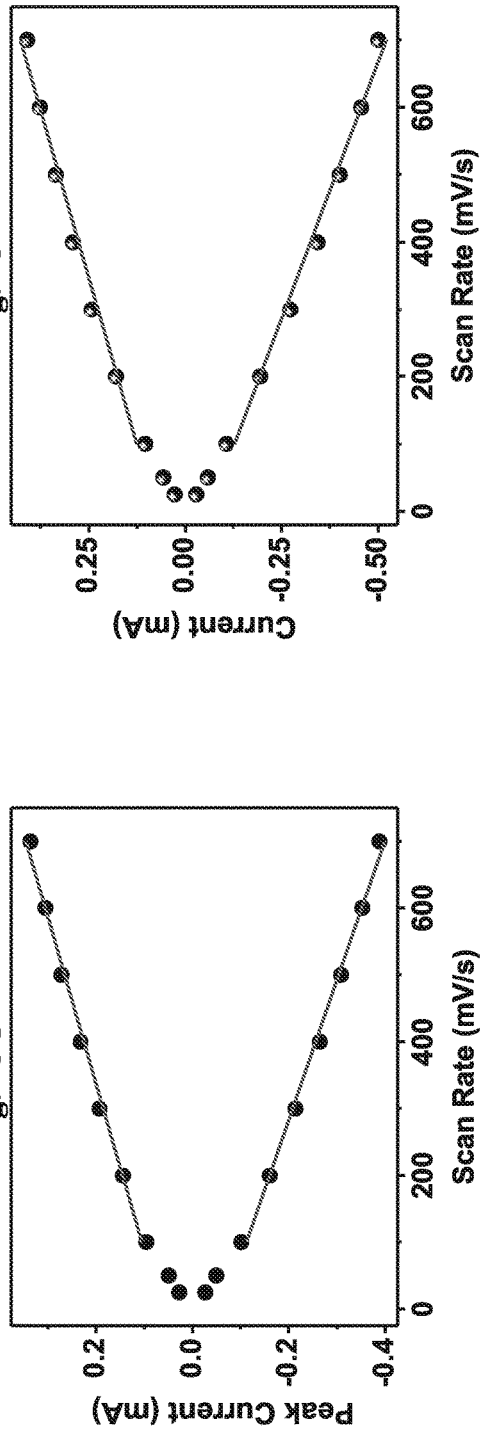
Fig. 23A
Fig. 23B
Fig. 23C
Fig. 23D

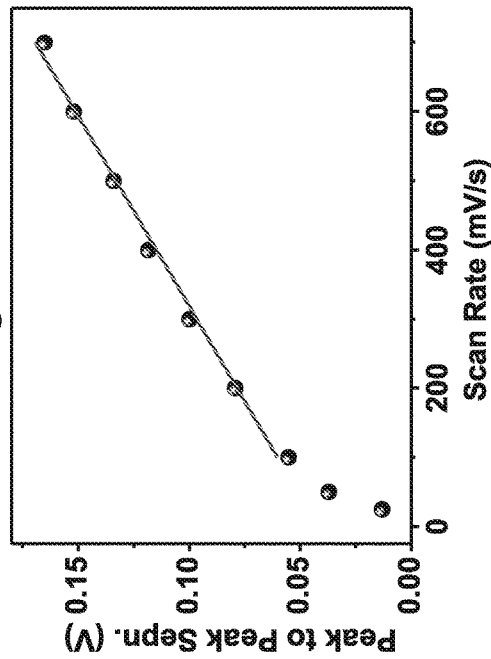
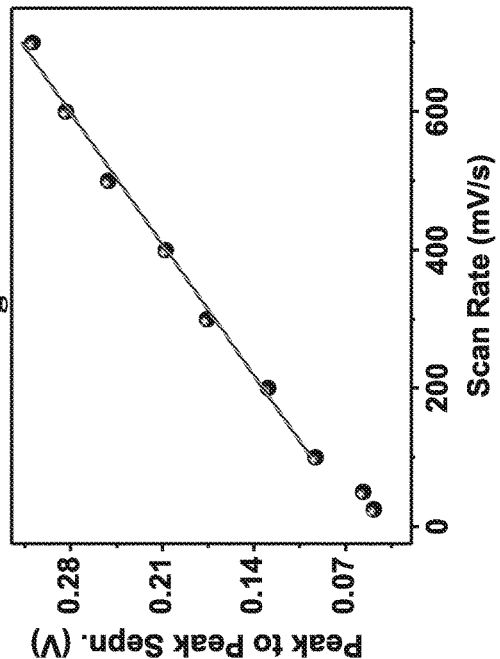
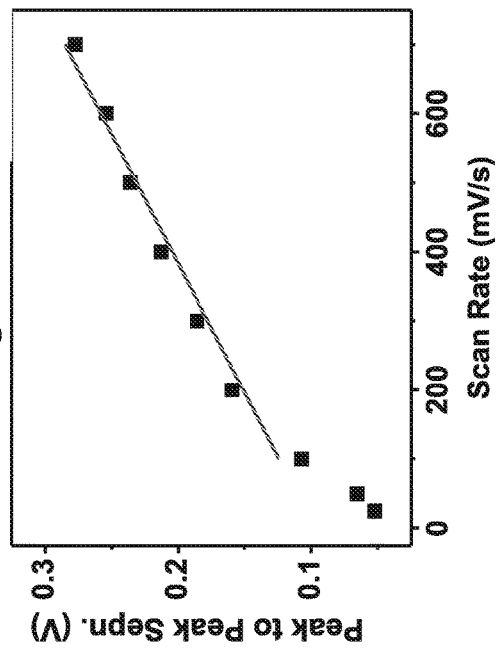
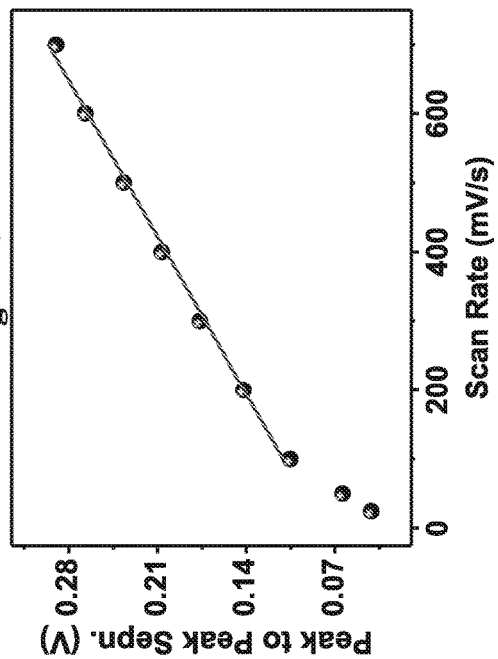

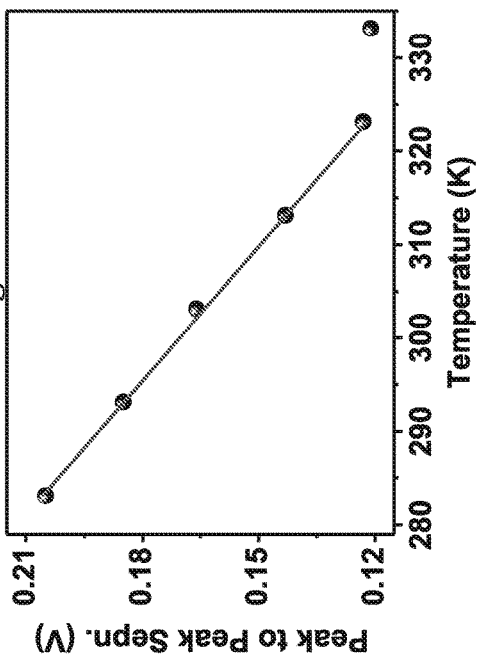
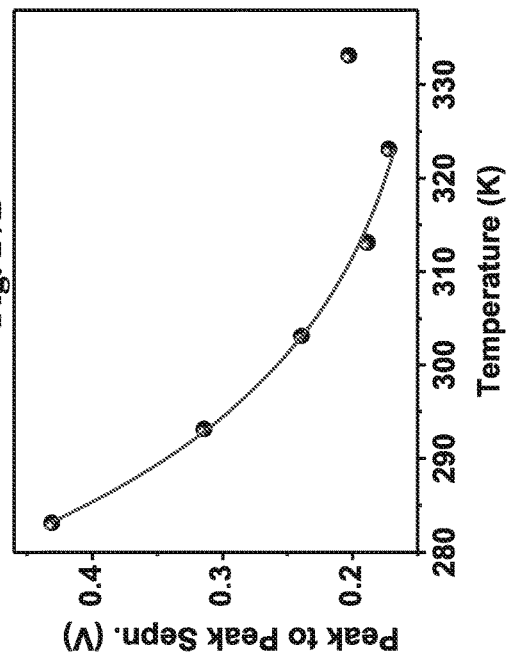
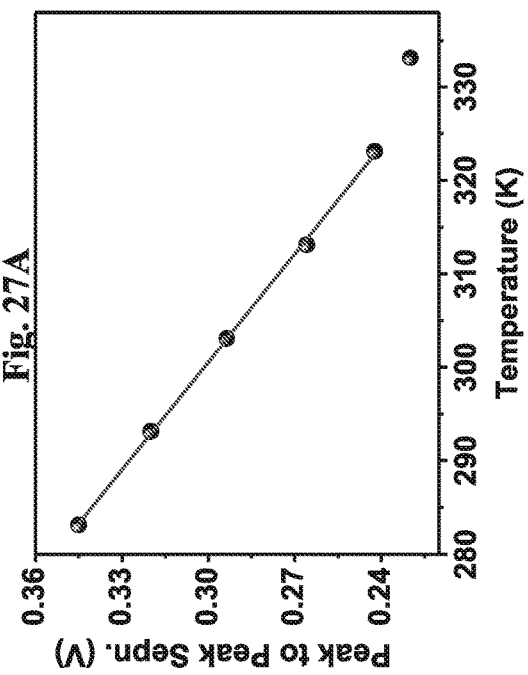
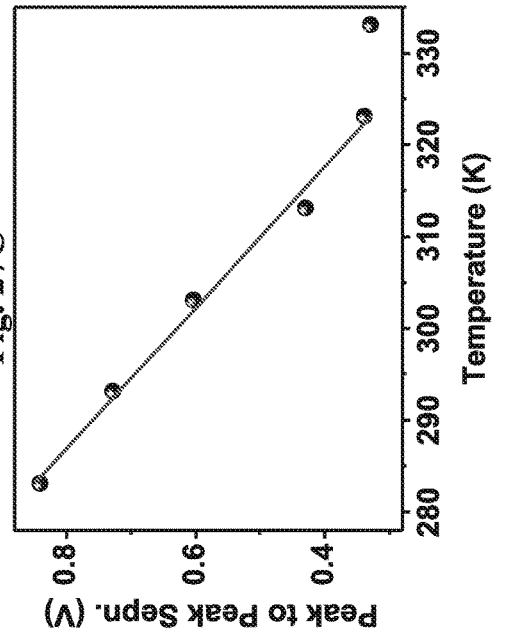

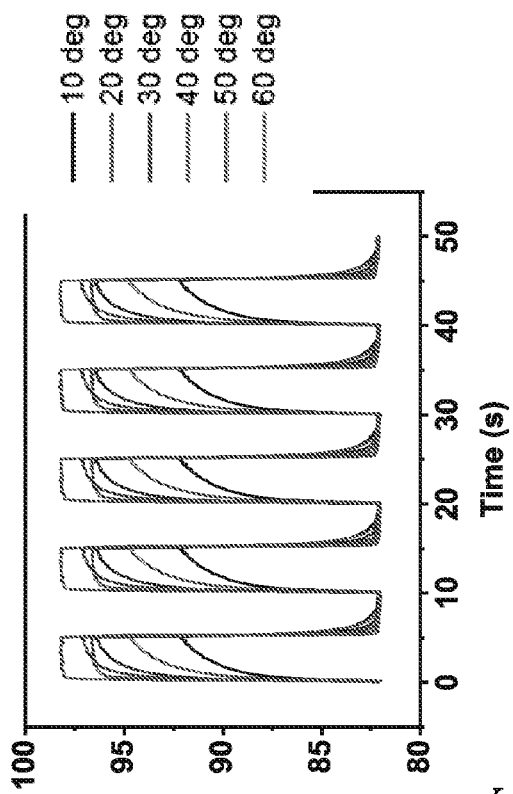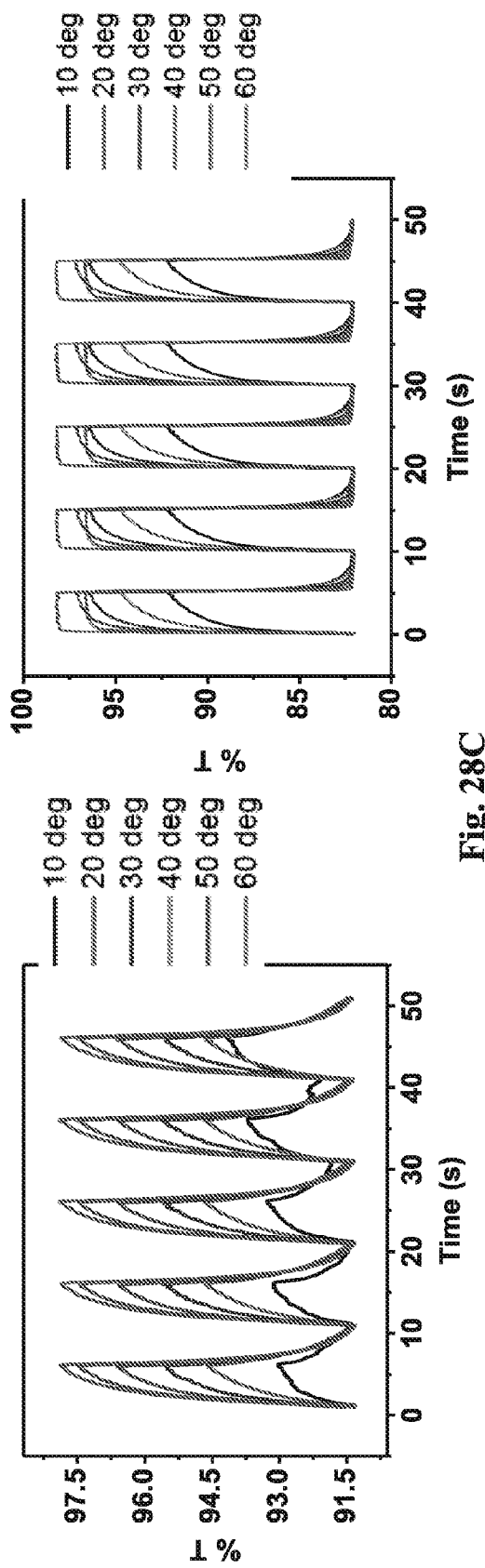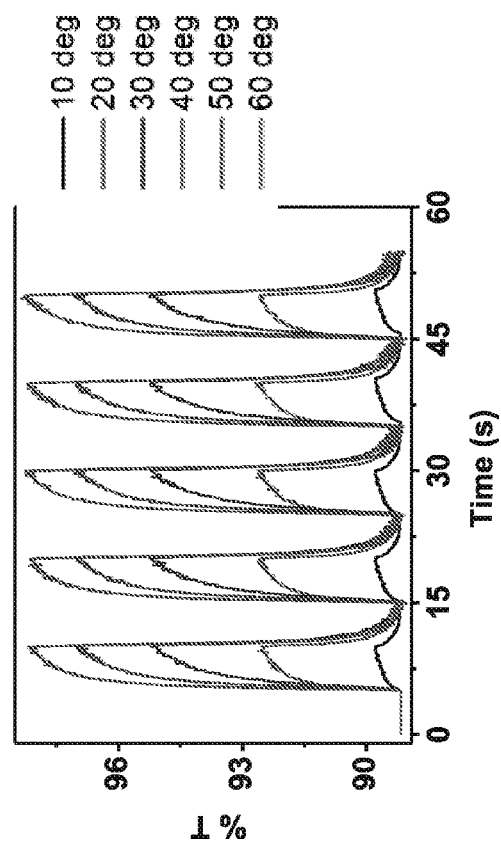
Fig. 28A
Fig. 28B
Fig. 28C

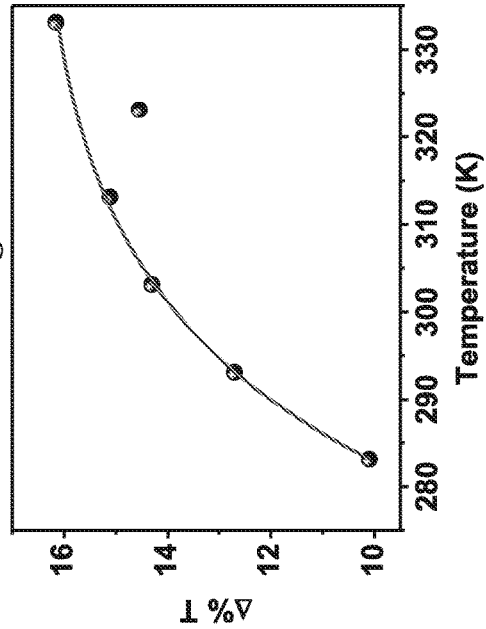
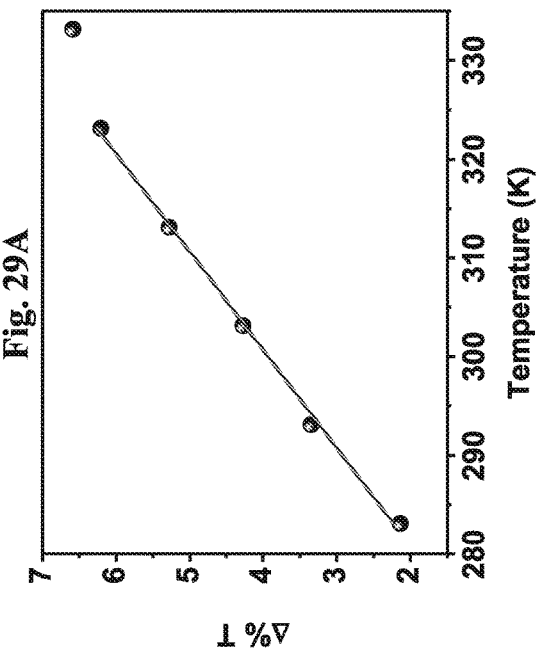
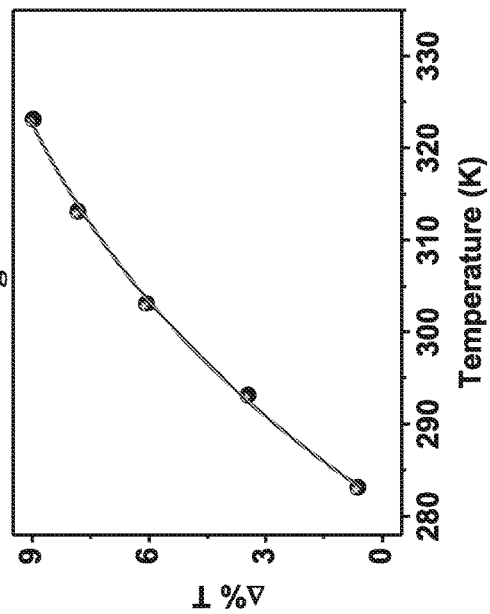

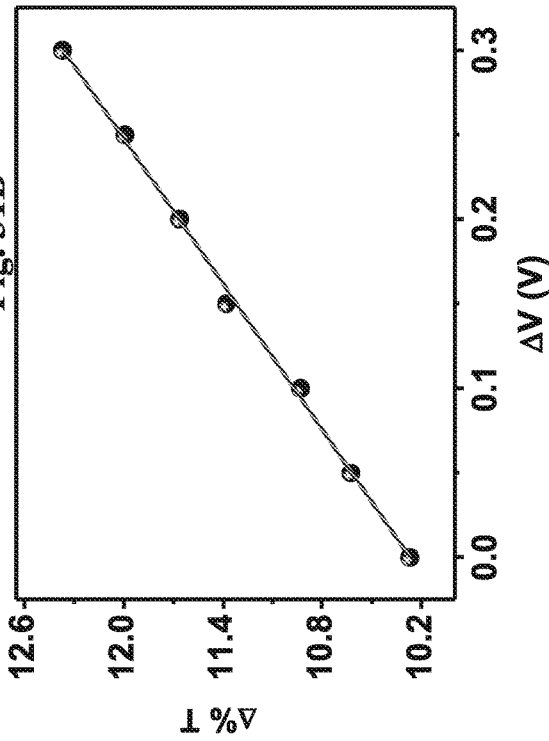
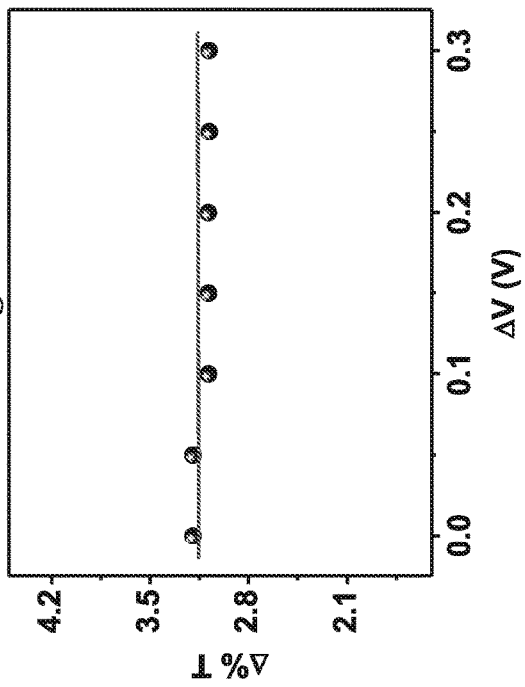
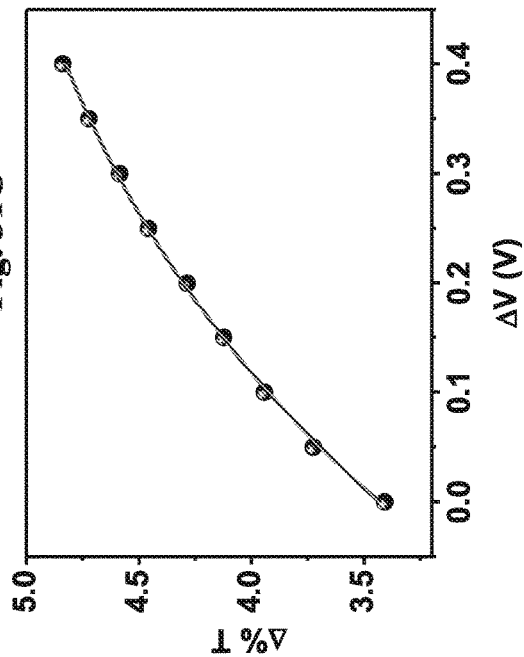

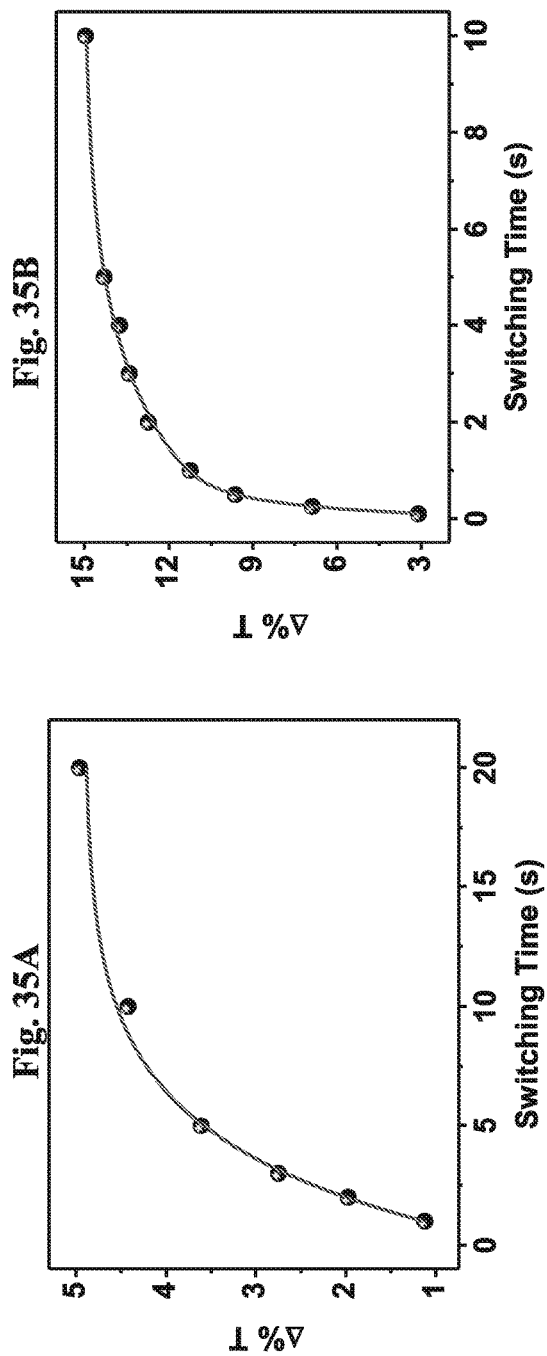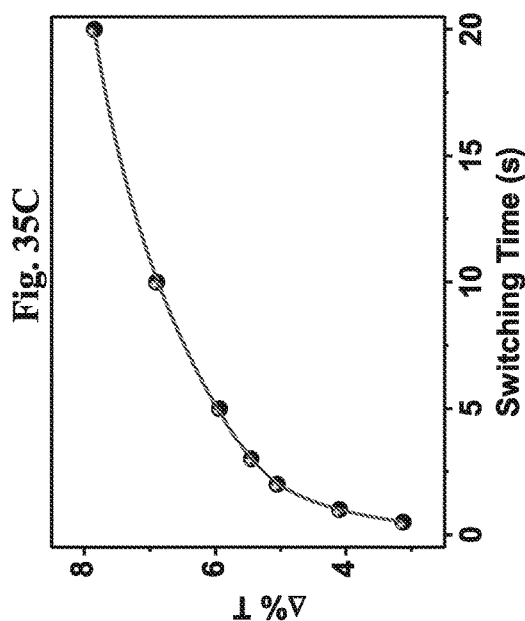

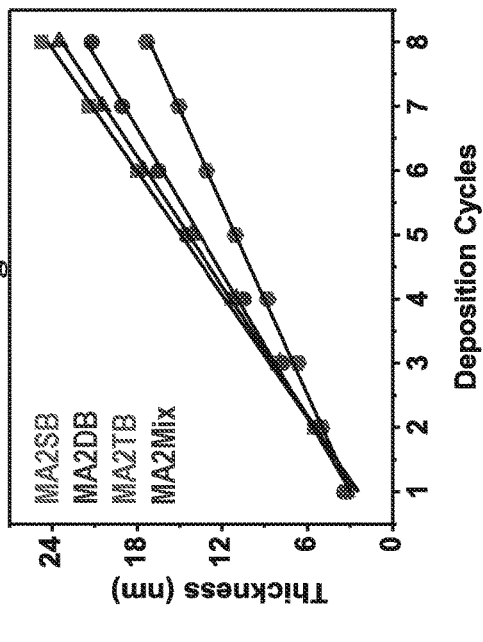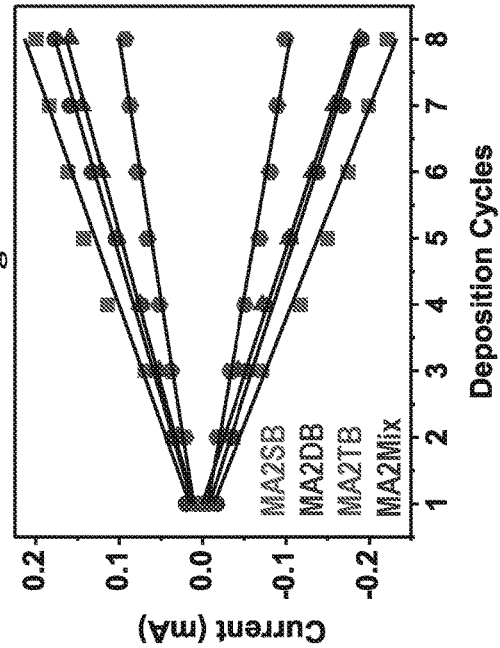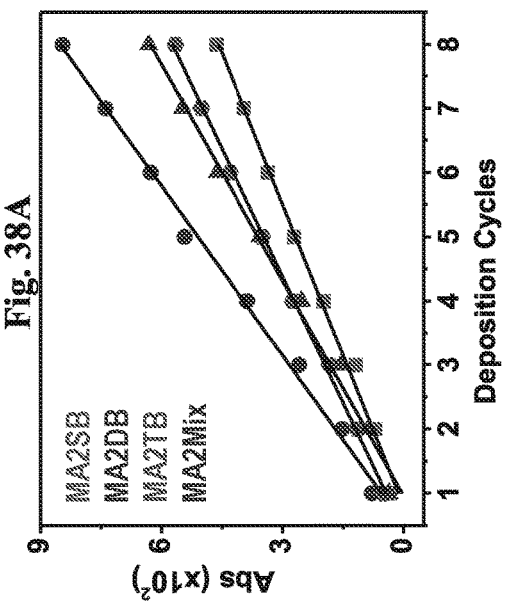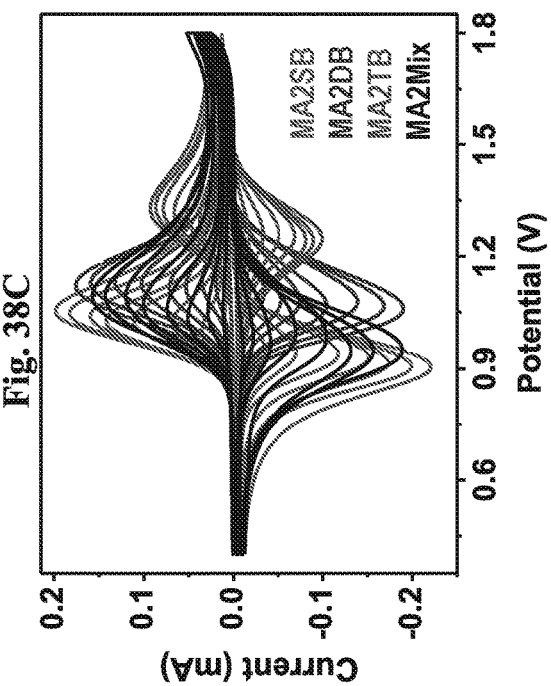
Fig. 38A
Fig. 38B
Fig. 38C
Fig. 38D

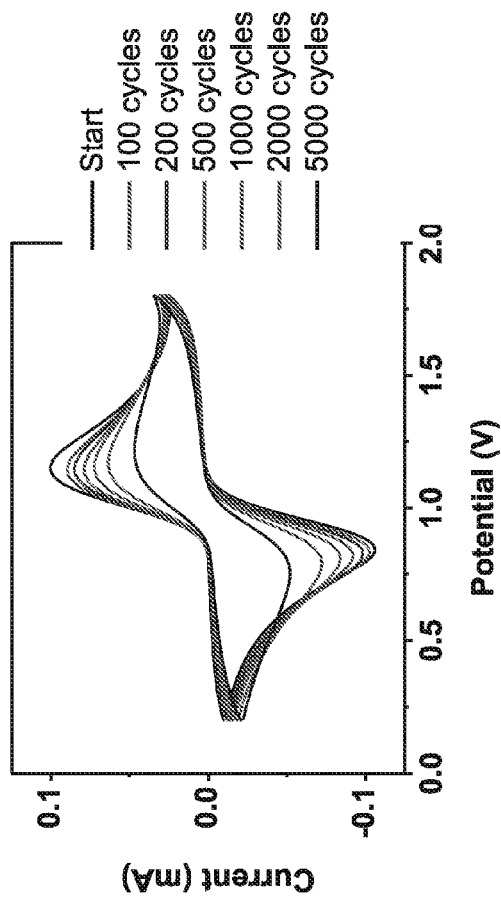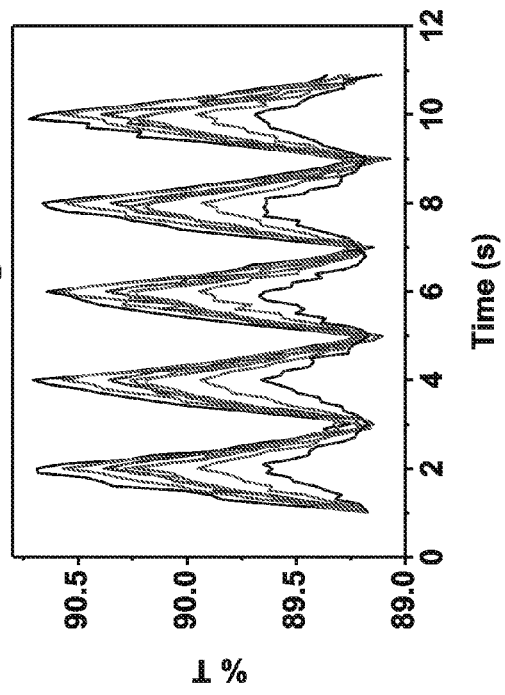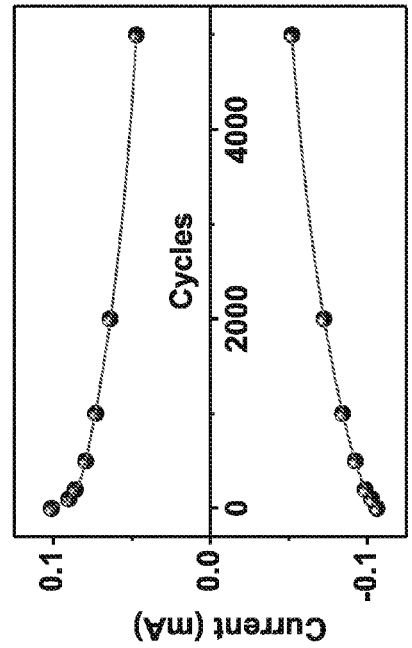

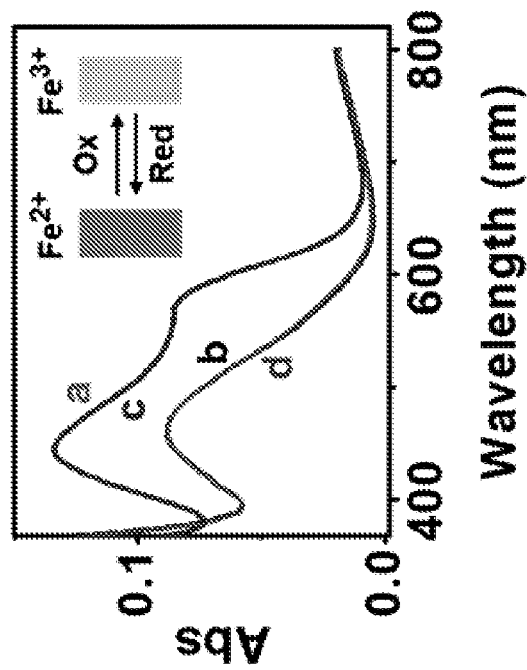
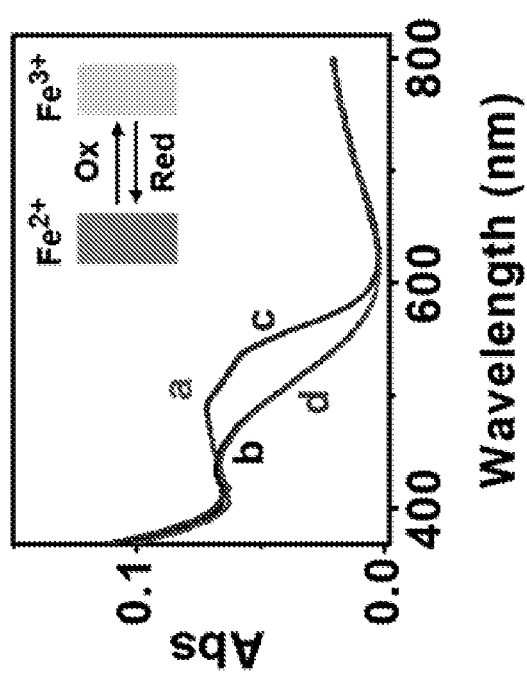
Fig. 44A
Fig. 44B

METAL-BASED TRIS-BIPYRIDYL COMPLEXES AND USES THEREOF IN ELECTROCHROMIC APPLICATIONS

CROSS-REFERENCE TO RELATED APPLICATIONS

This application is a National Phase Application of PCT International Application No. PCT/IL2014/051005, International Filing Date Nov. 19, 2014, claiming priority and the benefit from U.S. Provisional Application Ser. No. 61/906,565 filed on Nov. 20, 2013, and claiming priority and the benefit from Israel Patent Application Serial No. IL 229525, filed on Nov. 20, 2013, which are hereby incorporated by reference.

TECHNICAL FIELD

The present invention relates to metal-based tris-bipyridyl complexes, and their use in fabrication of surface confined assemblies for electrochromic applications.

Abbreviations

AFM, atomic force microscopy; CV, cyclic voltammetry; CPNF, coordination polymer network film; DMF, dimethylformamide; ECD, electrochromic device; FTO, fluorine doped tin oxide; ITO, indium tin oxide; MA, molecular assembly; MLCT, metal-to-ligand charge-transfer; RT, room temperature; SEC, spectroelectrochemistry; SELD, single electrochrome laminated device; SPMA, self-propagating molecule-based assembly; SSD, solid state device; TCO, transparent conductive oxide; THF, tetrahydrofuran; XPS, X-ray photoemission spectroscopy; XRR, X-ray reflectivity.

BACKGROUND ART

Layer by layer deposition technique in combination with selective metal-ligand coordination has been a powerful tool for generation of complex, self-driven, supramolecular surface confined architectures consisting of functional superlattices. These molecular assemblies, owing to their diverse intrinsic properties, span a wide variety of potential applications ranging from molecular electronics, display and sensor technologies, to solar cells and data storage. It has been reported that the complex properties of these assemblies could be fine-tuned by controlling their growth and mode of deposition. This, in turn, depends on the coordination geometry and molecular structure of the components. Hence, careful and rational design of the backbone structure and geometry could provide a simple, but challenging alternative for achieving control over the properties of multi-component layer by layer assemblies.

One of the most intriguing properties of selected redox active metal-organic materials—electrochromism—arises from their ability to exhibit valance electron transitions (MLCT, intraligand excitation or intravalance charge transfer) upon electrochemical oxidation or reduction. Electrochromic materials are of profound significance as promising candidates for use in smart windows (electrochromic windows), smart mirrors, display devices (electrochromic paper, goggles, helmet visors), etc. By definition, an electrochromic material is one which, by the application of a potential difference, can alter its optical properties upon reversible redox transformation, with distinguishable absorption/reflection spectra in its oxidized and reduced states. CPNFs constructed from such electrochromic materials of metal-organic nature exemplifies the combined advantages of organic and inorganic thin films. These advantages include long range processibility, transmittance modulation, high coloration efficiency, low switching time, open circuit memory effect and high stability.

International Publication No. WO 2006/085319 discloses a device having reversible and optically readable properties, the device comprising a substrate having an electrically conductive surface and carrying a redox-active layered structure, configured to have at least one predetermined electronic property including at least one of electrodensity and oxidation state, said at least one electronic property being changeable by subjecting the layer structure to an electric field, wherein the electronic properties of the layered structure define an optical characteristic of the structure thereby determining an optical response of the structure to certain incident light, the device enabling to effect a change in said electronic property that results in a detectable change in the optical response of the layered structure. International Publication No. WO 2009/095924 discloses such a device comprising, as a redox-active layered structure, a charged tris-bipyridyl $Os^{2+}$, $Fe^{2+}$ or $Ru^{2+}$ complex, for the optical detection, quantification and detoxification of $Cr^{6+}$ by reversible metal-substrate electron transfer.

International Publication No. WO 2011/141913 discloses a solid-state, multi-valued, molecular random access memory device, comprising an electrically, optically and/or magnetically addressable unit, a memory reader, and a memory writer. The addressable unit comprises a conductive substrate; one or more layers of electrochromic, magnetic, redox-active, and/or photochromic materials deposited on the conductive substrate; and a conductive top layer deposited on top the one or more layers. The memory writer applies a plurality of predetermined values of potential biases or optical signals or magnetic fields to the unit, wherein each predetermined value applied results in a uniquely distinguishable optical, magnetic and/or electrical state of the unit, thus corresponding to a unique logical value. The memory reader reads the optical, magnetic and/or electrical state of the unit.

International Publication No. WO 2014/009952 discloses a logic circuit for performing a logic operation comprising a plurality of predetermined solid-state molecular chips, each molecular chip having multiple states obtained after application of a corresponding input. After applying predetermined inputs on the molecular chips, reading the states of the molecular chips produces a logical output according to the logic operation.

International Publication No. WO 2014/061018 discloses a device having an electrically conductive surface and carrying a molecular assembly, preferably composed of two or more redox-active based molecular components arranged in a specific order or sequence, such that the sequence of the components and their thickness dictate the assembly properties and consequently the uses of the device. Such a device can be used in fabrication of a multistate memory, electrochromic window, smart window, electrochromic display, binary memory, solar cell, molecular diode, charge storage device, capacitor, or transistor.

The aforesaid patent publications are herewith incorporated by reference in their entirety as if fully disclosed herein.

SUMMARY OF INVENTION

In one aspect, the present invention relates to a tris-bipyridyl complex of the general formula I:

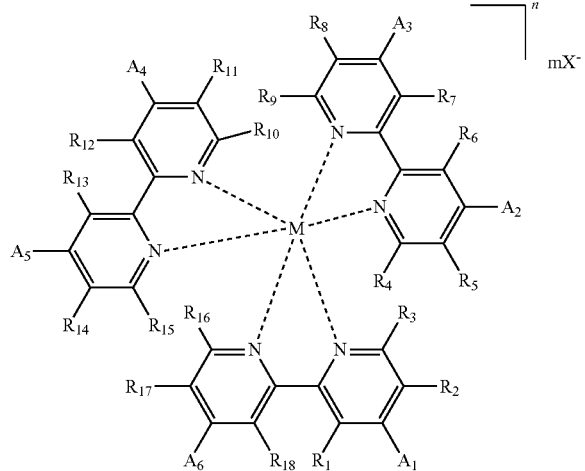

wherein

M is a transition metal selected from Mn, Fe, Co, Ni, Cu, Zn, Ti, V, Cr, Rh or Ir;

n is the formal oxidation state of the transition metal, wherein n is 0-6;

X is a counter anion;

m is a number ranging from 0 to 6;

$R_1$ to $R_{18}$ each independently is selected from H, halogen, —OH, —$N_3$, —$NO_2$, —CN, —N($R_{20}$)$_2$, —CON($R_{20}$)$_2$, —COOR$_{20}$, —SR$_{20}$, —SO$_3$H, —CH=CH-pyridyl, ($C_1$-$C_{10}$)alkyl, ($C_2$-$C_{10}$)alkenyl, ($C_2$-$C_{10}$)alkynyl, ($C_1$-$C_{10}$)alkoxy, cycloalkyl, heterocycloalkyl, aryl, heteroaryl, protected carboxyl, or protected amino, wherein said ($C_1$-$C_{10}$)alkyl, ($C_2$-$C_{10}$)alkenyl, ($C_2$-$C_{10}$)alkynyl, cycloalkyl, heterocycloalkyl, aryl and heteroaryl may optionally be substituted with halogen, —OR$_{20}$, —COR$_{20}$, —COOR$_{20}$, —OCOOR$_{20}$, —OCON($R_{20}$)$_2$, —($C_1$-$C_8$)alkylene-COOR$_{20}$, —CN, N($R_{20}$)$_2$, —NO$_2$, —SR$_{20}$, —($C_1$-$C_8$)alkyl, —O—($C_1$-$C_8$)alkyl, —CON($R_{20}$)$_2$, or —SO$_3$H;

$A_1$ to $A_6$ each independently is a group of the formula III, i.e., a pyridine or pyridine derivative moiety, or of the formula IV, i.e., a pyrimidine or pyrimidine derivative moiety, linked to the ring structure of the complex of general formula I via $R_{19}$

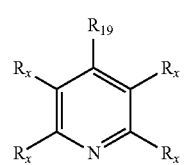

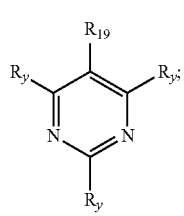

$R_{19}$ each independently is selected from a covalent bond, C—C, C=C, C≡C, N=N, C=N, N=C, C—N, N—C, —COO—, —CONH—, —CON(OH)—, —NR$_{20}$—, —Si(R$_{20}$)$_2$—, an alkylene optionally interrupted by one or more heteroatoms selected from O, S or N, phenylene, biphenylene, a peptide moiety consisting of 3 to 5 amino acid residues,

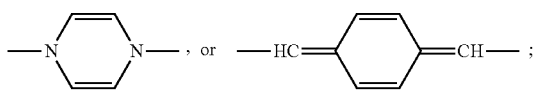

$R_x$ and $R_y$ each independently is selected from H, halogen, —OH, —$N_3$, —$NO_2$, —CN, —N($R_{20}$)$_2$, —CON($R_{20}$)$_2$, —COOR$_{20}$, —SR$_{20}$, —SO$_3$H, —CH=CH-pyridyl, ($C_1$-$C_{10}$)alkyl, ($C_2$-$C_{10}$)alkenyl, ($C_2$-$C_{10}$)alkynyl, ($C_1$-$C_{10}$)alkoxy, cycloalkyl, heterocycloalkyl, aryl, heteroaryl, protected carboxyl, or protected amino, wherein said ($C_1$-$C_{10}$)alkyl, ($C_2$-$C_{10}$)alkenyl, ($C_2$-$C_{10}$)alkynyl, cycloalkyl, heterocycloalkyl, aryl and heteroaryl may optionally be substituted with halogen, —OR$_{20}$, —COR$_{20}$, —COOR$_{20}$, —OCOOR$_{20}$, —OCON($R_{20}$)$_2$, —($C_1$-$C_8$)alkylene-COOR$_{20}$, —CN, N($R_{20}$)$_2$, —NO$_2$, —SR$_{20}$, —($C_1$-$C_8$)alkyl, —O—($C_1$-$C_8$)alkyl, —CON($R_{20}$)$_2$, or —SO$_3$H; and $R_{20}$ each independently is H, ($C_1$-$C_6$)alkyl or aryl.

In another aspect, the present invention relates to an iron-based tris-bipyridyl complex of the general formula II:

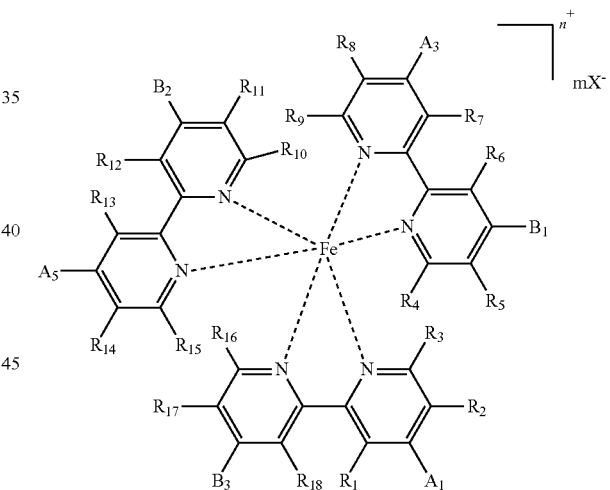

wherein n is the formal oxidation state of the Fe, wherein n is 0-6;

X is a counter anion;

m is a number ranging from 0 to 6;

$R_1$ to $R_{18}$ each independently is selected from H, halogen, —OH, —$N_3$, —$NO_2$, —CN, —N($R_{20}$)$_2$, —CON($R_{20}$)$_2$, —COOR$_{20}$, —SR$_{20}$, —SO$_3$H, —CH=CH-pyridyl, ($C_1$-$C_{10}$)alkyl, ($C_2$-$C_{10}$)alkenyl, ($C_2$-$C_{10}$)alkynyl, ($C_1$-$C_{10}$)alkoxy, cycloalkyl, heterocycloalkyl, aryl, heteroaryl, protected carboxyl, or protected amino, wherein said ($C_1$-$C_{10}$)alkyl, ($C_2$-$C_{10}$)alkenyl, ($C_2$-$C_{10}$)alkynyl, cycloalkyl, heterocycloalkyl, aryl and heteroaryl may optionally be substituted with halogen, —OR$_{20}$, —COR$_{20}$, —COOR$_{20}$, —OCOOR$_{20}$, —OCON($R_{20}$)$_2$, —($C_1$-$C_8$)alkylene-COOR$_{20}$, —CN, N($R_{20}$)$_2$, —NO$_2$, —SR$_{20}$, —($C_1$-$C_8$)alkyl, —O—($C_1$-$C_8$)alkyl, —CON($R_{20}$)$_2$, or —SO$_3$H;

$A_1$, $A_3$ and $A_5$ each independently is a group of the formula III, i.e., a pyridine or pyridine derivative moiety, or of the formula IV, i.e., a pyrimidine or pyrimidine derivative moiety, linked to the ring structure of the complex of general formula II via $R_{19}$

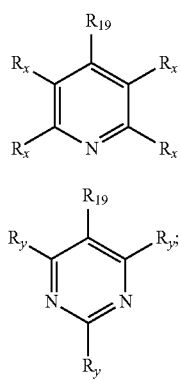

$R_{19}$ is selected from a covalent bond, C—C, cis/trans C=C, C≡C, N=N, C=N, N=C, C—N, N—C, —COO—, —CONH—, —CON(OH)—, —NR$_{20}$—, —Si(R$_{20})_2$—, an alkylene optionally interrupted by one or more heteroatoms selected from O, S or N, phenylene, biphenylene, a peptide moiety consisting of 3 to 5 amino acid residues,

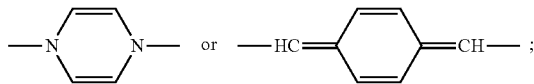

$R_x$ and $R_y$ each independently is selected from H, halogen, —OH, —N$_3$, —NO$_2$, —CN, —N(R$_{20})_2$, —CON(R$_{20})_2$, —COOR$_{20}$, —SR$_{20}$, —SO$_3$H, —CH=CH-pyridyl, ($C_1$-$C_{10}$)alkyl, ($C_2$-$C_{10}$)alkenyl, ($C_2$-$C_{10}$)alkynyl, ($C_1$-$C_{10}$) alkoxy, cycloalkyl, heterocycloalkyl, aryl, heteroaryl, protected carboxyl, or protected amino, wherein said ($C_1$-$C_{10}$) alkyl, ($C_2$-$C_{10}$)alkenyl, ($C_2$-$C_{10}$)alkynyl, cycloalkyl, heterocycloalkyl, aryl and heteroaryl may optionally be substituted with halogen, —OR$_{20}$, —COR$_{20}$, —COOR$_{20}$, —OCOOR$_{20}$, —OCON(R$_{20})_2$, —(C$_1$-C$_8$)alkylene-COOR$_{20}$, —CN, N(R$_{20})_2$, —NO$_2$, —SR$_{20}$, —(C$_1$-C$_8$)alkyl, —O—(C$_1$-C$_8$)alkyl, —CON(R$_{20})_2$, or —SO$_3$H;

$B_1$ to $B_3$ each independently is selected from H, halogen, —OH, —N$_3$, —NO$_2$, —CN, —N(R$_{20})_2$, —CON(R$_{20})_2$, —COOR$_{20}$, —SR$_{20}$, —SO$_3$H, —CH=CH-pyridyl, ($C_1$-$C_{10}$)alkyl, ($C_2$-$C_{10}$)alkenyl, ($C_2$-$C_{10}$)alkynyl, ($C_1$-$C_{10}$) alkoxy, cycloalkyl, heterocycloalkyl, aryl, heteroaryl, protected carboxyl, or protected amino, wherein said ($C_1$-$C_{10}$) alkyl, ($C_2$-$C_{10}$)alkenyl, ($C_2$-$C_{10}$)alkynyl, cycloalkyl, heterocycloalkyl, aryl and heteroaryl may optionally be substituted with halogen, —OR$_{20}$, —COR$_{20}$, —COOR$_{20}$, —OCOOR$_{20}$, —OCON(R$_{20})_2$, —(C$_1$-C$_8$)alkylene-COOR$_{20}$, —CN, N(R$_{20})_2$, —NO$_2$, —SR$_{20}$, —(C$_1$-C$_8$)alkyl, —O—(C$_1$-C$_8$)alkyl, —CON(R$_{20})_2$, or —SO$_3$H; and $R_{20}$ each independently is H, ($C_1$-$C_6$)alkyl or aryl.

In a further aspect, the present invention provides a device comprising a substrate having an electrically conductive surface and a layered structure disposed thereon, said layered structure comprising at least one redox-active compound configured to have a predetermined oxidation state being changeable upon subjecting said layered structure to an electric field, wherein exposure of said device to a potential change causes reversible electron transfer, which results in a change in the electrochromic properties of said layered structure with high coloration efficiency, said device having high electrochemical stability when repeatedly exposed to a potential change, wherein said redox-active compound each independently is a tris-bipyridyl complex of the general formula I or an iron-based tris-bipyridyl complex of the general formula II as defined above. Such a device may be used, e.g., in smart windows, electrochromic windows, smart mirrors, optical filters, frequency doubling devices, optical switches, modulators, spatial light modulators, phase masks, data transfer devices, data storage devices, pulse shapers, optical processors, electrochromic display devices, smart papers, electrochromic goggles, electrochromic helmets, electrochromic paints, or visors; as well as in memory devices.

In yet another aspect, the present invention provides a memory device comprising a substrate having an electrically conductive surface and a layered structure disposed thereon, said layered structure comprising at least one redox-active compound configured to have at least one a predetermined electronic property, including at least one of electrodensity and oxidation state, said predetermined electronic property being changeable upon subjecting said layered structure to an electric field, wherein said redox-active compound each independently is a tris-bipyridyl complex of the general formula I or an iron-based tris-bipyridyl complex of the general formula II as defined above.

BRIEF DESCRIPTION OF DRAWINGS

FIG. 1 shows the formation of the template layers (TLs). The TLs were generated by reaction of S1 with benzylchloride terminated coupling layers (CLs) covalently attached to silicon, quartz and glass substrates.

FIGS. 19A-19D show MLCT Abs Maxima vs. ellipsometer derived thickness of MA2SB (19A, R>0.99), MA2DB (19B, $R^2>0.99$), MA2TB (19C, $R^2>0.99$) and MA2Mix (18D, $R^2>0.99$), showing the uniformity of the assemblies.

FIGS. 20A-20D show CV of MA2SB (20A), MA2DB (20B), MA2TB (20C) and MA2Mix (20D) for 1-8 deposition cycles (as shown by the arrow) at 100 mV/s as immersed in a 0.1M TBAPF6 electrolyte solution using the modified ITO as working electrode, Pt wire as counter electrode and Ag/Ag$^+$ reference electrode.

FIGS. 21A-21D show peak currents derived from CV of MA2SB (21A, R=0.98, 0.99), MA2DB (21B, $R^2=0.99$), MA2TB (21C, $R^2=0.98$) and MA2Mix (21D, $R^2=0.99$) vs. deposition cycles (for 1-8 deposition cycles at 100 mV/s as immersed in a 0.1M TBAPF6 electrolyte solution using the modified ITO as working electrode, Pt wire as counter electrode and Ag/Ag$^+$ reference electrode).

FIGS. 23A-23D show linear correlation between scan rate (mVs$^{-1}$) and peak current (mA) of MA2SB (23A, $R^2=0.98$), MA2DB (23B, $R^2=0.99$), MA2TB (23C, $R^2=0.99$) and MA2Mix (23D, $R^2=0.98$) for ~14 nm thick assemblies during oxidative and reductive directions (as immersed in a 0.1M TBAPF6 electrolyte solution using the modified ITO as working electrode, Pt wire as counter electrode and Ag/Ag$^+$ reference electrode).

FIGS. 24A-24D show linear correlation between scan rate (mVs$^{-1}$) and peak to peak separation (V) of MA2SB (24A, $R^2=0.97$), MA2DB (24B, $R^2=0.99$), MA2TB (24C, $R^2>0.99$) and MA2Mix (24D, $R^2=0.99$) for ~14 nm thick assemblies (as immersed in a 0.1M TBAPF6 electrolyte solution using the modified ITO as working electrode, Pt wire as counter electrode and Ag/Ag$^+$ reference electrode).

FIGS. 27A-27D show peak to peak separation (V) derived from CV of MA2SB (27A, $R^2>0.99$), MA2DB (27B, $R^2>0.99$), MA2TB (27C, $R^2=0.99$) and MA2Mix (27D, $R^2>0.99$) after 8 deposition cycles vs. temperature (at 100 mV/s as immersed in a 0.1M TBAPF6 electrolyte solution using the modified ITO as working electrode, Pt wire as counter electrode and Ag/Ag$^+$ reference electrode).

FIGS. 28A-28C show SEC of MA2SB (28A), MA2DB (28B) and MA2TB (28C) (8 deposition cycles) at different temperature (at a pulse width of 5 s. as immersed in a 0.1M TBAPF6 electrolyte solution using the modified ITO as working electrode, Pt wire as counter electrode and Ag/Ag$^+$ reference electrode).

FIGS. 29A-29C show Δ% T of MA2SB (29A, $R^2>0.99$), MA2DB (29B, $R^2>0.99$) and MA2TB (29C, $R^2>0.99$) (8 deposition cycles) vs. temperature (at a pulse width of 5 s. as immersed in a 0.1M TBAPF6 electrolyte solution using the modified ITO as working electrode, Pt wire as counter electrode and Ag/Ag$^+$ reference electrode).

FIGS. 31A-31C show the effect of overpotential on the SEC of MA2SB (31A, 20° C.), MA2DB (31B, 10° C.) and MA2TB (31C, 20° C.) (8 deposition cycles) at low temperature (at a pulse width of 5 s. as immersed in a 0.1M TBAPF6 electrolyte solution using the modified ITO as working electrode, Pt wire as counter electrode and Ag/Ag$^+$ reference electrode). There was no detectable effect of overpotential on MA2SB and MA2TB assemblies at 10° C. and the signal to noise ratio was poor.

FIGS. 35A-35C show the effect of switching time (pulse width) on the SEC of MA2SB (35A, RT, $R^2>0.99$), MA2DB (35B, RT, $R^2>0.99$) and MA2TB (35C, RT, $R^2>0.99$) (8 deposition cycles, as immersed in a 0.1M TBAPF6 electrolyte solution using the modified ITO as working electrode, Pt wire as counter electrode and Ag/Ag$^+$ reference electrode, RT).

FIGS. 38A-38H show MA2SB, MA2DB, MA2TB and MA2Mix. (38A) Intensities of absorption bands (MLCT) at 535 nm (MA2SB, $R^2=0.99$), 590 nm (MA2DB, $R^2=0.99$), 576 nm (MA2TB, $R^2>0.99$), and 581 nm (MA2Mix, $R^2=0.99$) vs. the number of deposition cycles; (38B) Thickness of MA2SB, MA2DB, MA2TB and MA2Mix vs. the number of deposition cycles ($R^2>0.99$); (38C) CVs of MA2SB, MA2DB, MA2TB and MA2Mix; (38D) Peak currents of MA2SB, MA2DB, MA2TB and MA2Mix vs. the number of deposition cycles ($R^2>0.98$); (38E) Peak currents of MA2SB, MA2DB, MA2TB and MA2Mix at various temperature ($R^2>0.96$); (38F) Peak to peak separation of MA2SB, MA2DB, MA2TB and MA2Mix at various temperature ($R^2>0.98$); (38G) Response time (for >95% switching) of MA2SB, MA2DB, MA2TB and MA2Mix at various temperature (5 s gap, $R^2>0.99$); (38H) Switching time of MA2SB, MA2DB, MA2TB and MA2Mix at various temperature ($R^2>0.99$).

FIGS. 42A-42C show the electrochemical stability of MA2SB. (42A) CV of MA2SB up to 5000 switching cycles; (42B) Maximum current as in 42A vs. the number of switching cycles ($R^2>0.99$); (42C) SEC of MA2SB on ITO at 535 nm over a potential range of 0.5 to 1.5V with a 1 s pulse width. Each segment in 42C corresponds to the first five switching cycles in every interval. This multistep square-wave potential measurement was carried out using a 0.1 M Bu$_4$NPF$_6$/PC electrolyte solution.

(43B) Maximum current as in 43A vs. the number of switching cycles ($R^2>0.98$); (43C) SEC of MA2SB on ITO at 575 nm over a potential range of 0.8 to 1.9V with a 1 s pulse width. Each segment in 43C corresponds to the first five switching cycles in every interval. This multistep square-wave potential measurement was carried out using a 0.1 M $Bu_4NPF_6$/PC electrolyte solution.

FIGS. 44A-44B show electrochromic switching of the MAs. Optical absorption spectra corresponding to consecutive oxidation and reduction of (44A) MA2SB and (44B) MA2TB. SEC was done using double-potential steps between 0.2 and 1.6 V (MA2SB) and 0.5 and 1.9V (MA2TB): (a) reduced ($Fe^{2+}$), (b) oxidized ($Fe^{3+}$), (c) reduced ($Fe^{2+}$) and (d) oxidized ($Fe^{3+}$) states. Inset: photographs of MA2SB and MA2TB showing the colored ($Fe^{2+}$) and the bleached ($Fe^{3+}$) states.

Figure 45:
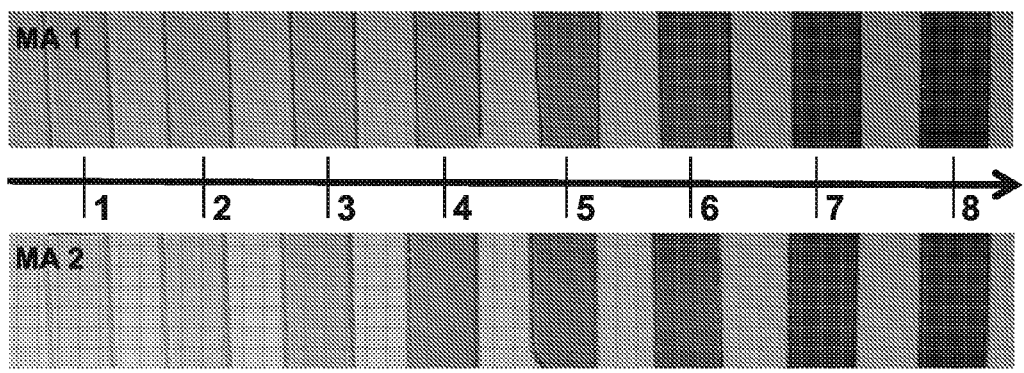

FIG. 45 shows color profile of quartz slides functionalized with MA1DB (top) and MA2DB (bottom).

Figure 46:
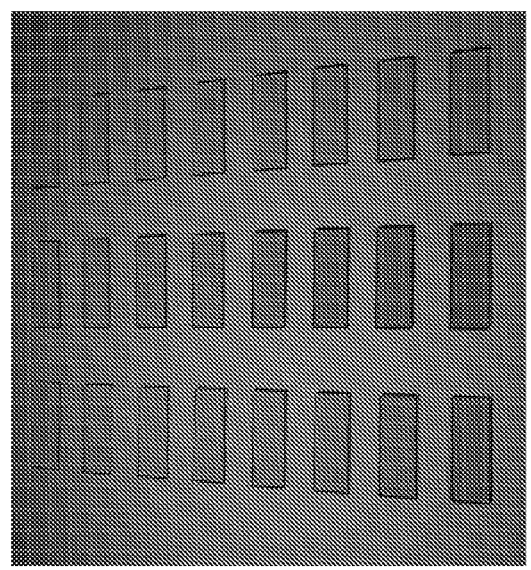

FIG. 46 shows color profile of quartz slides functionalized with MA2SB (top), MA2DB (middle) and MA2TB (bottom).

Figure 47:
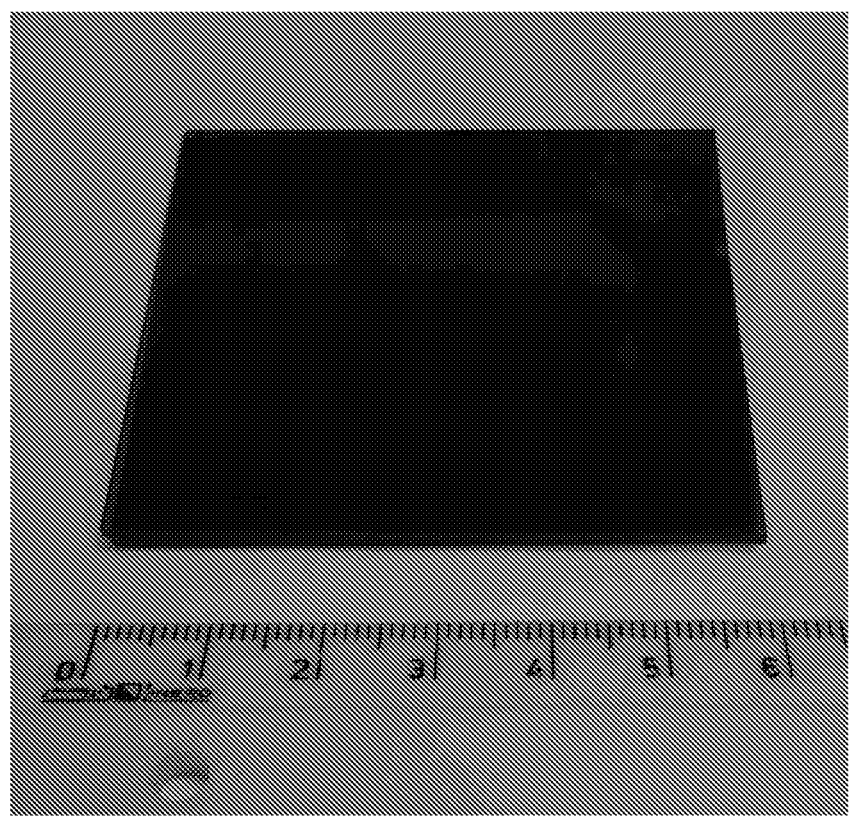

FIG. 47 shows two TCO coated functionalized (with MA2DB) glass slides as required for a smart window.

Figure 48:
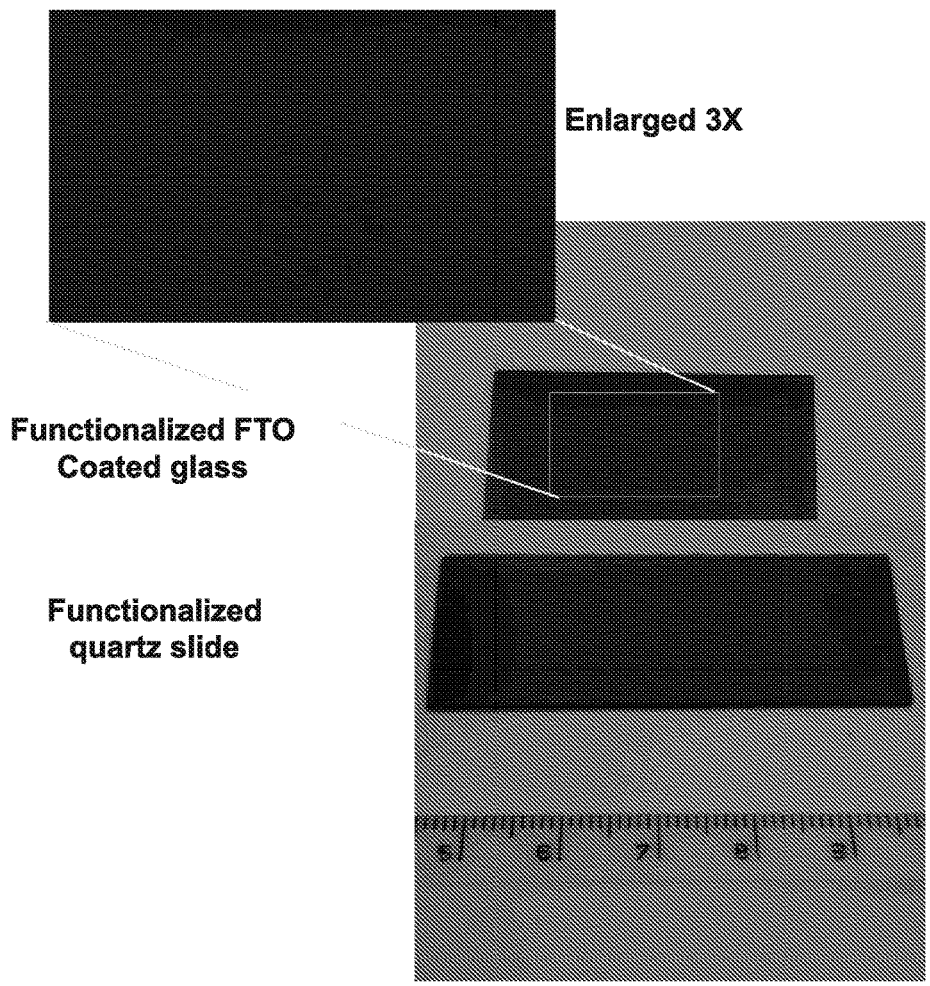

FIG. 48 shows photographs showing the uniformity of the assemblies on large surface area slides. Functionalized FTO coated glass slide (top) and functionalized quartz slide (bottom).

Figure 49:
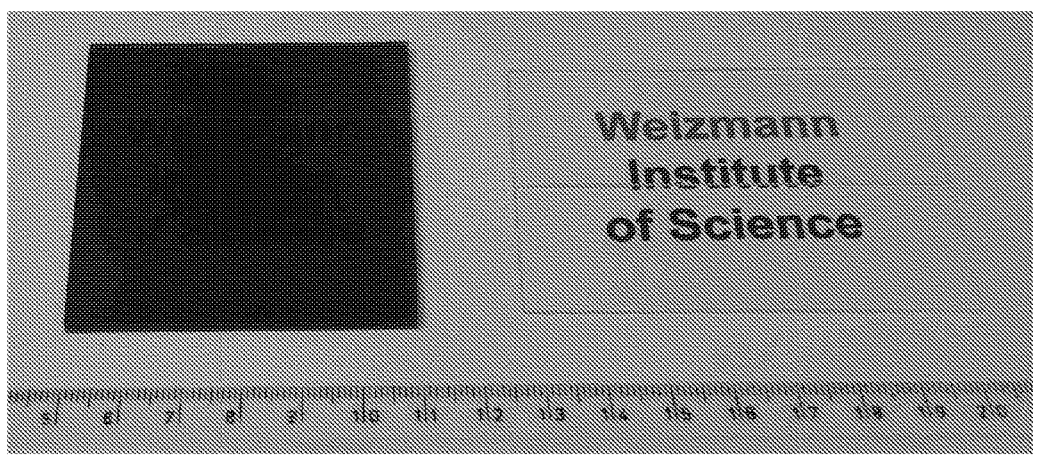

FIG. 49 shows a photograph of functionalized (with MA2DB) FTO coated glass slides proving the opacity (left) and see through properties of uncoated glass (right).

DETAILED DESCRIPTION OF THE INVENTION

The present invention relates to a tris-bipyridyl complex of the general formula I and to an iron-based tris-bipyridyl complex of the general formula II as defined above.

The term "oxidation state" also known as "oxidation number" is an indicator of the degree of oxidation of an atom in a chemical compound. As used herein, this term refers to the oxidation state of the tris-bipyridyl complexes of the present invention, more particularly to the oxidation state of the metal atom in the complex which may be either the electrically neutral state of said metal atom or any state other than said neutral state produced/caused by the gain or loss of electrons, i.e., reduction or oxidation, respectively.

The term "optical properties", as used herein, refers to the absorption spectrum of the tris-bipyridyl complex of the present invention, wherein the change in the optical properties is caused electrochemically by addition or withdrawal of one or more electrons to or from said tris-bipyridyl complex, more particularly, to or from the metal atom in the complex.

The counter anion "X" in the tris-bipyridyl complexes of the present invention may be any suitable anion having a negative charge of, e.g., −1 or −2, such as $Br^-$, $Cl^-$, $F^-$, $I^-$, $PF_6^-$, $BF_4^-$, $OH^-$, $ClO_4^-$, $SO_3^{2-}$, $SO_4^{2-}$, $CF_3COO^-$, $CN^-$, alkylCOO⁻, arylCOO⁻, or a combination thereof. The value of "m" represents the ratio between the oxidation state of the transition metal and the valence of said anion, and may thus be, e.g., 0.5, 1, 1.5, 2, 2.5, 3, 4, 5 or 6.

The term "halogen", as used herein, includes fluoro, chloro, bromo, and iodo.

The term "alkyl", as used herein, typically means a straight or branched hydrocarbon radical having preferably 1-10 carbon atoms, and includes, e.g., methyl, ethyl, n-propyl, isopropyl, n-butyl, isobutyl, sec-butyl, tert-butyl, n-pentyl, isopentyl, 2,2-dimethylpropyl, n-hexyl, n-heptyl, n-octyl, n-nonyl, n-decyl, and the like. The alkyl may be substituted, e.g., with one or more substituents each independently selected from halogen, —$OR_{20}$, —$COR_{20}$, —$COOR_{20}$, —$OCOOR_{20}$, —$OCON(R_{20})_2$, —($C_1$-$C_8$)alkylene-$COOR_{20}$, —CN, —$N(R_{20})_2$, —$NO_2$, —$SR_{20}$, —($C_1$-$C_8$)alkyl, —O—($C_1$-$C_8$)alkyl, —$CON(R_{20})_2$, or —$SO_3H$, wherein $R_{20}$ each independently is H, ($C_1$-$C_6$)alkyl or aryl. The term "alkylCOO" particularly refers to an alkyl group substituted by a carboxyl group on any one of its carbon atoms, e.g., $CH_3COO^-$ or $C_2H_5COO^-$. The term "alkylene" refers to a linear divalent hydrocarbon chain having preferably 1-10 carbon atoms and includes, e.g., methylene, ethylene, propylene, butylene, pentylene, hexylene, heptylene, octylene, and the like.

The terms "alkenyl" and "alkynyl" typically mean straight or branched hydrocarbon radicals having preferably 2-10 carbon atoms and at least one double or triple bond, respectively. Non-limiting examples of such alkenyls are ethenyl, propenyl, 3-buten-1-yl, 2-ethenylbutyl, 3-octen-1-yl, and the like, and propynyl, 2-butyn-1-yl, 3-pentyn-1-yl, and the like. Each one of the alkenyl and alkynyl may be substituted, e.g., with one or more substituents each independently selected from halogen, —$OR_{20}$, —$COR_{20}$, —$COOR_{20}$, —$OCOOR_{20}$, —$OCON(R_{20})_2$, —($C_1$-$C_8$)alkylene-$COOR_{20}$, —CN, —$N(R_{20})_2$, —$NO_2$, —$SR_{20}$, —($C_1$-$C_8$)alkyl, —O—($C_1$-$C_8$)alkyl, —$CON(R_{20})_2$, or —$SO_3H$, wherein $R_{20}$ each independently is H, ($C_1$-$C_6$)alkyl or aryl.

The term "alkoxy" refers to the group —OR, wherein R is an alkyl group.

The term "cycloalkyl" typically means a mono- or bicyclic saturated hydrocarbyl group having preferably 3-10 carbon atoms such as cyclopropyl, cyclobutyl, cyclopentyl, cyclohexyl, cycloheptyl, cyclooctyl, cyclodecyl, bicyclo[3.2.1]octyl, 10 bicyclo[2.2.1]heptyl, and the like. The term "heterocycloalkyl" refers to a cycloalkyl, in which at least one of the carbon atoms of the ring is replaced by a heteroatom selected from N, O or S. Each one of the cycloalkyl and heterocycloalkyl may be substituted, e.g., with one or more substituents each independently selected from halogen, —$OR_{20}$, —$COR_{20}$, —$COOR_{20}$, —$OCOOR_{20}$, —$OCON(R_{20})_2$, —($C_1$-$C_8$)alkylene-$COOR_{20}$, —CN, —$N(R_{20})_2$, —$NO_2$, —$SR_{20}$, —($C_1$-$C_8$)alkyl, —O—($C_1$-$C_8$)alkyl, —$CON(R_{20})_2$, or —$SO_3H$, wherein $R_{20}$ each independently is H, ($C_1$-$C_6$)alkyl or aryl.

The term "aryl" denotes an aromatic carbocyclic group, preferably having 6-14 carbon atoms, consisting of a single ring or multiple rings either condensed or linked by a covalent bond such as, but not limited to, phenyl, naphthyl, phenanthryl, and biphenyl. The aryl group may be substituted by any known substituent. The aryl may be substituted, e.g., with one or more substituents each independently selected from halogen, —$OR_{20}$, —$COR_{20}$, —$COOR_{20}$, —$OCOOR_{20}$, —$OCON(R_{20})_2$, —($C_1$-$C_8$)alkylene-$COOR_{20}$, —CN, —$N(R_{20})_2$, —$NO_2$, —$SR_{20}$, —($C_1$-$C_8$)alkyl, —O—($C_1$-$C_8$)alkyl, —$CON(R_{20})_2$, or —$SO_3H$, wherein $R_{20}$ each independently is H, ($C_1$-$C_6$)alkyl or aryl. The term "arylCOO" refers to such a substituted aryl, in this case being substituted by a carboxylate group.

The term "heteroaryl" refers to a radical derived from a mono- or polycyclic heteroaromatic ring containing one to three, preferably 1-2, heteroatoms selected from the group consisting of N, O and S. When the heteroaryl is a monocyclic ring, it is preferably a radical of a 5-6-membered ring such as, but not limited to, pyrrolyl, furyl, thienyl, thiazinyl, pyrazolyl, pyrazinyl, imidazolyl, oxazolyl, isoxazolyl, thiazolyl, isothiazolyl, pyridyl, pyrimidinyl, 1,2,3-triazinyl, 1,3,4-triazinyl, and 1,3,5-triazinyl. Polycyclic heteroaryl radicals are preferably composed of two rings such as, but not limited to, benzofuryl, isobenzofuryl, benzothienyl, indolyl, quinolinyl, isoquinolinyl, imidazo[1,2-a]pyridyl, benzimidazolyl, benzthiazolyl, benzoxazolyl, pyrido[1,2-a]pyrimidinyl and 1,3-benzodioxinyl. The heteroaryl may be substituted, e.g., with one or more substituents each independently selected from halogen, —$OR_{20}$, —$COR_{20}$, —$COOR_{20}$, —$OCOOR_{20}$, —$OCON(R_{20})_2$, —$(C_1-C_8)$alkylene-$COOR_{20}$, —CN, —$N(R_{20})_2$, —$NO_2$, —$SR_{20}$, —$(C_1-C_8)$alkyl, —O—$(C_1-C_8)$alkyl, —$CON(R_{20})_2$, or —$SO_3H$, wherein $R_{20}$ each independently is H, $(C_1-C_6)$alkyl or aryl. It is to be understood that when a polycyclic heteroaryl is substituted, the substitution may be in any of the carbocyclic and/or heterocyclic rings.

The term "amino" refers to the group —$NH_2$ or to substituted amino including secondary, tertiary and quaternary substitutions wherein the substituents are alkyl or aryl. The term "protected amino" refers to such groups which may be converted to the amino group.

The term "carboxyl" refers to the group —COOH. The term "protected carboxyl" refers to such groups which may be converted into the carboxyl group, e.g., esters such as —COOR, wherein R is an alkyl group or an equivalent thereof, and others which may be known to a person skilled in the art of organic chemistry.

The term "amino acid" as used herein refers to an organic compound comprising both amine and carboxylic acid functional groups, which may be either a natural or non-natural amino acid. The twenty two natural amino acids are aspartic acid (Asp), tyrosine (Tyr), leucine (Leu), tryptophan (Trp), arginine (Arg), valine (Val), glutamic acid (Glu), methionine (Met), phenylalanine (Phe), serine (Ser), alanine (Ala), glutamine (Gln), glycine (Gly), proline (Pro), threonine (Thr), asparagine (Asn), lysine (Lys), histidine (His), isoleucine (Ile), cysteine (Cys), selenocysteine (Sec), and pyrrolysine (Pyl). Non-limiting examples of non-natural amino acids include diaminopropionic acid (Dap), diaminobutyric acid (Dab), ornithine (Orn), aminoadipic acid, β-alanine, 1-naphthylalanine, 3-(1-naphthyl)alanine, 3-(2-naphthyl)alanine, γ-aminobutiric acid (GABA), 3-(aminomethyl) benzoic acid, p-ethynyl-phenylalanine, p-propargly-oxy-phenylalanine, m-ethynyl-phenylalanine, p-bromophenylalanine, p-iodophenylalanine, p-azidophenylalanine, p-acetylphenylalanine, azidonorleucine, 6-ethynyl-tryptophan, 5-ethynyl-tryptophan, 3-(6-chloroindolyl)alanine, 3-(6-bromoindolyl)alanine, 3-(5-bromoindolyl)alanine, azidohomoalanine, p-chlorophenylalanine, α-aminocaprylic acid, O-methyl-L-tyrosine, N-acetylgalactosamine-α-threonine, and N-acetylgalactosamine-α-serine. The term "peptide" as used herein refers to a short chain of amino acid monomers linked by peptide bonds, i.e., the covalent bond formed when a carboxyl group of one amino acid reacts with an amino group of another amino acid. Particular peptides comprise 2, 3, 4, 5, 6, 7, 8 or more, preferably 3-5, amino acid monomers.

In certain embodiments, the tris-bipyridyl complex of the present invention is a complex of the general formula I, wherein $R_1$ to $R_{18}$ each independently is H, halogen, —OH, —$N_3$, —$NO_2$, —CN, —$N(R_{20})_2$, —$SR_{20}$, —CH=CH-pyridyl, $(C_1-C_{10})$alkyl, aryl, or heteroaryl, wherein said $(C_1-C_{10})$alkyl, aryl and heteroaryl may optionally be substituted with halogen, —$OR_{20}$, —$COR_{20}$, —$COOR_{20}$, —$OCOOR_{20}$, —$OCON(R_{20})_2$, —$(C_1-C_8)$alkylene-$COOR_{20}$, —CN, $N(R_{20})_2$, —$NO_2$, —$SR_{20}$, —$(C_1-C_8)$alkyl, —O—$(C_1-C_8)$alkyl, —$CON(R_{20})_2$, or —$SO_3H$; and $R_{20}$ each is H. Preferred such embodiments are those wherein $R_1$ to $R_{18}$ each is H.

In certain embodiments, the tris-bipyridyl complex of the present invention is a complex of the general formula I, wherein $A_1$ to $A_6$ each independently is a pyridine moiety, i.e., a group of the formula III wherein $R_x$ is H, or a pyrimidine moiety, i.e., a group of the formula IV wherein $R_y$ is H.

In certain embodiments, the tris-bipyridyl complex of the present invention is a complex of the general formula I, wherein $R_{19}$ each independently is C—C, C=C, C≡C, N=N, C=N, N=C, C—N, N—C, —COO—, —CONH—, —CON(OH)—, —$NR_{20}$—, —$Si(R_{20})_2$—, or an alkylene optionally interrupted by one or more heteroatoms selected from O, S or N, preferably C—C, C=C or C≡C.

In certain embodiments, the tris-bipyridyl complex of the present invention is a complex of the general formula I, wherein $A_1$ to $A_6$ each is a pyridine moiety, i.e., a group of the formula III, wherein $R_x$ is H and $R_{19}$ is C—C, C=C or C≡C; or a pyrimidine moiety, i.e., a group of the formula IV, wherein $R_y$ is H and $R_{19}$ is C—C, C=C or C≡C.

In certain embodiments, the tris-bipyridyl complex of the present invention is a complex of the general formula I as defined in any one of the embodiments above, wherein $R_1$ to $R_{18}$ each independently is H, halogen, —OH, —$N_3$, —$NO_2$, —CN, —$N(R_{20})_2$, —$SR_{20}$, —CH=CH-pyridyl, $(C_1-C_{10})$alkyl, aryl, or heteroaryl, wherein said $(C_1-C_{10})$alkyl, aryl and heteroaryl may optionally be substituted with halogen, —$OR_{20}$, —$COR_{20}$, —$COOR_{20}$, —$OCOOR_{20}$, —$OCON(R_{20})_2$, —$(C_1-C_8)$alkylene-$COOR_{20}$, —CN, $N(R_{20})_2$, —$NO_2$, —$SR_{20}$, —$(C_1-C_8)$alkyl, —O—$(C_1-C_8)$alkyl, —$CON(R_{20})_2$, or —$SO_3H$; $A_1$ to $A_6$ each independently is a group of the formula III, wherein $R_x$ is H, or of the formula IV, wherein $R_y$ is H; $R_9$ each independently is C—C, C=C, C≡C, N=N, C=N, N=C, C—N, N—C, —COO—, —CONH—, —CON(OH)—, —$NR_{20}$—, —$Si(R_{20})_2$—, or an alkylene optionally interrupted by one or more heteroatoms selected from O, S or N; and $R_{20}$ each is H.

In particular such embodiments, the tris-bipyridyl complex of the present invention is a complex of the general formula I, wherein $R_1$ to $R_{18}$ each is H; $A_1$ to $A_6$ each independently is a group of the formula III, wherein $R_x$ is H, or of the formula IV, wherein $R_y$ is H; and $R_{19}$ each independently is C—C, C=C or C≡C. More particular such complexes are those wherein M is Fe, i.e., iron-based tris-bipyridyl complexes, most particularly wherein n is 2 or 3.

In certain specific embodiments, the tris-bipyridyl complex of the invention is a complex of the general formula I, wherein M is Fe; n and m each is 2 or 3; X is $PF_6^-$; $R_1$ to $R_{18}$ each is H; $A_1$ to $A_6$ each independently is a group of the formula III, wherein $R_x$ is H; and (i) $R_{19}$ each is C—C, i.e., [tris[4,4'-bis(2-(4-pyridyl)ethyl)-2,2'-bipyridine]iron(II)] bis(hexafluoro-phosphate), or [tris[4,4'-bis(2-(4-pyridyl)ethyl)-2,2'-bipyridine]iron(III)] tris(hexafluoro-phosphate), herein identified complex 2SB($Fe^{2+}$) or 2SB($Fe^{3+}$), respectively; (ii) $R_{19}$ each is C=C, i.e., [tris[4,4'-bis(2-(4-pyridyl)ethenyl)-2,2'-bipyridine]iron(II)] bis(hexafluoro-phosphate), or [tris[4,4'-bis(2-(4-pyridyl)ethenyl)-2,2'-bipyridine]iron(II)] tris(hexafluoro-phosphate), herein identified complex 2DB($Fe^{2+}$) or 2DB($Fe^{3+}$), respectively; or (ii) $R_{19}$ each is C≡C, i.e., [tris[4,4'-bis(2-(4-pyridyl)ethynyl)-2,2'-bipyridine]iron(II)] bis(hexafluoro-phosphate), or [tris[4,4'-bis(2-(4-pyridyl)ethynyl)-2,2'-bipyridine]iron(III)] tris(hexafluoro-phosphate), herein identified complex 2TB($Fe^{2+}$) or 2TB($Fe^{3+}$), respectively (see Appendix).

In other specific embodiments, the tris-bipyridyl complex of the invention is a complex of the general formula I, wherein M is Fe; n and m each is 2 or 3; X is $PF_6^-$; $R_1$ to $R_{18}$ each is H; $A_1$ to $A_6$ each independently is a group of the formula IV, wherein $R_y$ is H; and (i) $R_{19}$ each is C—C, i.e., [tris[4,4'-bis(2-(4-pyrimidinyl)ethyl)-2,2'-bipyridine]iron (II)] bis(hexafluoro-phosphate), or [tris[4,4'-bis(2-(4-pyrimidinyl)ethyl)-2,2'-bipyridine]iron(III)] tris(hexafluoro-phosphate), herein identified complex 4SB($Fe^{2+}$) or 4SB($Fe^{3+}$), respectively; (ii) $R_{19}$ each is C═C, i.e., [tris[4,4'-bis(2-(4-pyrimidinyl)ethenyl)-2,2'-bipyridine]iron(II)] bis(hexafluoro-phosphate), or [tris[4,4'-bis(2-(4-pyrimidinyl)ethenyl)-2,2'-bipyridine] iron(III)] tris(hexafluoro-phosphate), herein identified complex 4DB($Fe^{2+}$) or 4DB($Fe^{3+}$), respectively; or (iii) $R_{19}$ each is C≡C, i.e., [tris[4,4'-bis(2-(4-pyrimidinyl)ethynyl)-2,2'-bipyridine]iron(II)] bis(hexafluoro-phosphate), or [tris[4,4'-bis(2-(4-pyrimidinyl)ethynyl)-2,2'-bipyridine]iron(III)] tris(hexafluoro-phosphate), herein identified complex 4TB($Fe^{2+}$) or 4TB($Fe^{3+}$), respectively (see Appendix).

In certain embodiments, the iron-based tris-bipyridyl complex of the present invention is a complex of the general formula II, wherein $R_1$ to $R_{18}$ each independently is H, halogen, —OH, —$N_3$, —$NO_2$, —CN, —$N(R_{20})_2$, —$SR_{20}$, —CH═CH-pyridyl, ($C_1$-$C_{10}$)alkyl, aryl, or heteroaryl, preferably H, wherein said ($C_1$-$C_{10}$)alkyl, aryl and heteroaryl may optionally be substituted with halogen, —$OR_{20}$, —$COR_{20}$, —$COOR_{20}$, —$OCOOR_{20}$, —$OCON(R_{20})_2$, —($C_1$-$C_8$)alkylene-$COOR_{20}$, —CN, $N(R_{20})_2$, —$NO_2$, —$SR_{20}$, —($C_1$-$C_8$)alkyl, —O—($C_1$-$C_8$)alkyl, —$CON(R_{20})_2$, or —$SO_3H$; and $R_{20}$ each is H. Preferred such embodiments are those wherein $R_1$ to $R_{18}$ each is H.

In certain embodiments, the iron-based tris-bipyridyl complex of the present invention is a complex of the general formula II, wherein $A_1$, $A_3$ and $A_5$ each independently is a pyridine moiety, i.e., a group of the formula III wherein $R_x$ is H, or a pyrimidine moiety, i.e., a group of the formula IV wherein $R_y$ is H.

In certain embodiments, the iron-based tris-bipyridyl complex of the present invention is a complex of the general formula II, wherein $R_{19}$ each independently is C—C, C═C, C≡C, N═N, C═N, N═C, C—N, N—C, —COO—, —CONH—, —CON(OH)—, —$NR_{20}$—, —Si($R_{20}$)$_2$—, or an alkylene optionally interrupted by one or more heteroatoms selected from O, S or N, preferably C—C, C═C or C≡C.

In certain embodiments, the iron-based tris-bipyridyl complex of the present invention is a complex of the general formula II, wherein $A_1$, $A_3$ and $A_5$ each is a pyridine moiety, i.e., a group of the formula III, wherein $R_x$ is H and $R_{19}$ is C—C, C═C or C≡C; or a pyrimidine moiety, i.e., a group of the formula IV, wherein $R_y$ is H and $R_{19}$ is C—C, C═C or C≡C.

In certain embodiments, the iron-based tris-bipyridyl complex of the present invention is a complex of the general formula II, wherein $B_1$ to $B_3$ each independently is H, halogen, —OH, —$N_3$, —$NO_2$, —CN, —$N(R_{20})_2$, —$SR_{20}$, —CH═CH-pyridyl, ($C_1$-$C_{10}$)alkyl, aryl, or heteroaryl, preferably ($C_1$-$C_4$)alkyl, more preferably methyl or ethyl, wherein said ($C_1$-$C_{10}$)alkyl, aryl and heteroaryl may optionally be substituted with halogen, —$OR_{20}$, —$COR_{20}$, —$COOR_{20}$, —$OCOOR_{20}$, —$OCON(R_{20})_2$, —($C_1$-$C_8$)alkylene-$COOR_{20}$, —CN, $N(R_{20})_2$, —$NO_2$, —$SR_{20}$, —($C_1$-$C_8$)alkyl, —O—($C_1$-$C_8$)alkyl, —$CON(R_{20})_2$, or —$SO_3H$; and $R_{20}$ each is H.

In certain embodiments, the iron-based tris-bipyridyl complex of the present invention is a complex of the general formula II as defined in any one of the embodiments above, wherein $R_1$ to $R_{18}$ each independently is H, halogen, —OH, —$N_3$, —$NO_2$, —CN, —$N(R_{20})_2$, —$SR_{20}$, —CH═CH-pyridyl, ($C_1$-$C_{10}$)alkyl, aryl, or heteroaryl, wherein said ($C_1$-$C_{10}$)alkyl, aryl and heteroaryl may optionally be substituted with halogen, —$OR_{20}$, —$COR_{20}$, —$COOR_{20}$, —$OCOOR_{20}$, —$OCON(R_{20})_2$, —($C_1$-$C_8$)alkylene-$COOR_{20}$, —CN, $N(R_{20})_2$, —$NO_2$, —$SR_{20}$, —($C_1$-$C_8$)alkyl, —O—($C_1$-$C_8$)alkyl, —$CON(R_{20})_2$, or —$SO_3H$; $A_1$, $A_3$ and $A_5$ each independently is a group of the formula III, wherein $R_x$ is H, or of the formula IV, wherein $R_y$ is H; $R_{19}$ each independently is C—C, C═C, C≡C, N═N, C═N, N═C, C—N, N—C, —COO—, —CONH—, —CON(OH)—, —$NR_{20}$—, —Si($R_{20}$)$_2$—, or an alkylene optionally interrupted by one or more heteroatoms selected from O, S or N; $B_1$ to $B_3$ each independently is H, halogen, —OH, —$N_3$, —$NO_2$, —CN, —$N(R_{20})_2$, —$SR_{20}$, —CH═CH-pyridyl, ($C_1$-$C_{10}$)alkyl, aryl, or heteroaryl, wherein said ($C_1$-$C_{10}$)alkyl, aryl and heteroaryl may optionally be substituted with halogen, —$OR_{20}$, —$COR_{20}$, —$COOR_{20}$, —$OCOOR_{20}$, —$OCON(R_{20})_2$, —($C_1$-$C_8$)alkylene-$COOR_{20}$, —CN, $N(R_{20})_2$, —$NO_2$, —$SR_{20}$, —($C_1$-$C_8$)alkyl, —O—($C_1$-$C_8$)alkyl, —$CON(R_{20})_2$, or —$SO_3H$; and $R_{20}$ each is H.

In particular such embodiments, the iron-based tris-bipyridyl complex of the present invention is a complex of the general formula II, wherein $R_1$ to $R_{18}$ each is H; $A_1$, $A_3$ and $A_5$ each independently is a group of the formula III, wherein $R_x$ is H, or of the formula IV, wherein $R_y$ is H; $R_{19}$ each independently is C—C, C═C or C≡C; and $B_1$ to $B_3$ each is ($C_1$-$C_4$)alkyl, preferably methyl or ethyl. Preferred such embodiments are those wherein n is 2 or 3.

In certain specific embodiments, the iron-based tris-bipyridyl complex of the invention is a complex of the general formula II, wherein X is $PF_6^-$; n and m each is 2 or 3; $R_1$ to $R_{18}$ each is H; $A_1$, $A_3$ and $A_5$ each is a group of the formula III, wherein $R_x$ is H; $B_1$ to $B_3$ each is methyl; and $R_{19}$ each is C—C, i.e., [tris[4'-methyl-4-(2-(4-pyridyl)ethyl)-2,2'-bipyridine]iron(II)] bis(hexafluoro-phosphate), or [tris[4'-methyl-4-(2-(4-pyridyl)ethyl)-2,2'-bipyridine] iron(III)] tris (hexafluoro-phosphate), herein identified complex 1SB($Fe^{2+}$) or 1SB($Fe^{3+}$), respectively; (ii) $R_{19}$ each is C═C, i.e., [tris[4'-methyl-4-(2-(4-pyridyl)ethenyl)-2,2'-bipyridine]iron (II)] bis(hexafluoro-phosphate), or [tris[4'-methyl-4-(2-(4-pyridyl)ethenyl)-2,2'-bipyridine]iron(III)] tris(hexafluoro-phosphate), herein identified complex 1DB($Fe^{2+}$) or 1DB ($Fe^{3+}$), respectively; or (iii) $R_{19}$ each is C≡C, i.e., [tris[4'-methyl-4-(2-(4-pyridyl)ethynyl)-2,2'-bipyridine]iron(II)] bis(hexafluoro-phosphate), or [tris[4'-methyl-4-(2-(4-pyridyl)ethynyl)-2,2'-bipyridine]iron(III)] tris(hexafluoro-phosphate), herein identified complex 1TB($Fe^{2+}$) or 1TB ($Fe^{3+}$), respectively (see Appendix).

In other specific embodiments, the iron-based tris-bipyridyl complex of the invention is a complex of the general formula II, wherein X is $PF_6^-$; n and m each is 2 or 3; $R_1$ to $R_{18}$ each is H; $A_1$, $A_3$ and $A_5$ each is a group of the formula IV, wherein $R_y$ is H; $B_1$ to $B_3$ each is methyl; and $R_{19}$ each is C—C, i.e., [tris[4'-methyl-4-(2-(5-pyrimidinyl)ethyl)-2, 2'-bipyridine]iron(II)] bis(hexafluoro-phosphate), or [tris[4'-methyl-4-(2-(5-pyrimidinyl) ethyl)-2,2'-bipyridine] iron (III)] tris(hexafluoro-phosphate), herein identified complex 3SB($Fe^{2+}$) or 3SB($Fe^{3+}$), respectively; (ii) $R_{19}$ each is C═C, i.e., [tris[4'-methyl-4-(2-(5-pyrimidinyl)ethenyl)-2,2'-bipyridine]iron(II)] bis(hexafluoro-phosphate), or [tris[4'-methyl-4-(2-(5-pyrimidinyl) ethenyl)-2,2'-bipyridine]iron (III)] tris(hexafluoro-phosphate), herein identified complex 3DB($Fe^{2+}$) or 3DB($Fe^{3+}$), respectively; or (iii) $R_{19}$ each is C≡C, i.e., [tris[4'-methyl-4-(2-(5-pyrimidinyl)ethynyl)-2, 2'-bipyridine]iron(II)] bis(hexafluoro-phosphate), or [tris[4'-methyl-4-(2-(5-pyrimidinyl) ethynyl)-2,2'-bipyridine]iron (III)] tris(hexafluoro-phosphate), herein identified complex 3TB($Fe^{2+}$) or 3TB($Fe^{3+}$), respectively (see Appendix).

The complexes of the present invention, i.e., both the tris-bipyridyl complex of the general formula I and the iron-based tris-bipyridyl complex of the general formula II, can be prepared using any suitable procedure or technique known in the art, e.g., as described in Materials and Methods hereinafter for the various iron-based tris-bipyridyl complexes exemplified. This procedure may of course be extended for the preparation of any tris-bipyridyl complex of the general formula I wherein the metal atom is Fe or one of the other metal atoms represented by the group M in the general formula I.

The tris-bipyridyl complex of the general formula I and the iron-based tris-bipyridyl complex of the general formula II, e.g., the complexes exemplified herein, are chiral complexes and consequently exist as enantiomers, i.e., optically pure isomers (Δ (delta) and Λ (lambda)), racemate, or a mixture wherein a certain enantiomer is enantiomerically enriched. Particular tris-bypyridyl complexes of the general formula II, e.g., complex 1DB($Fe^{2+}$), consist of facial and/or meridional isomers, depending on the ligand geometry with respect to the central metal ion, and may occur either as single isomers or as mixtures composed of any ratio of isomers. It should be understood that the present invention encompasses all such enantiomers, isomers, and mixtures thereof.

Optically active forms of the tris-bipyridyl complexes of the invention may be prepared/obtained using any method known in the art. Non-limiting examples of such methods include chiral chromatography including simulated moving bed chromatography, resolution of the racemic form by recrystallization techniques, resolution using optically pure reagents which form pairs of diastereomers which can be separated by any technique known in the art, and extraction with chiral solvents. A wide variety of chiral stationary phases are commercially available.

The facial and meridional isomers of the tris-bipyridyl complexes of the invention may be prepared/obtained using any method known in the art, e.g., by chemical synthesis using tethers and/or protective groups, or by chromatographic separation using suitable stationary phases (e.g., silica, alumina or sephadex), including simulated moving bed chromatography.

In study 1 hereinafter, pyridine terminated template layers were generated from silane based coupling layers covalently attached to silicon, quartz and glass substrates, and subsequently, two different multi-component molecular assemblies, herein identified MA1DB and MA2DB, were constructed, layer by layer, via iterative immersion of these functionalized substrates in a 1 mM solution of $PdCl_2$ $(PhCN)_2$ in THF and 0.2 mM solution of the respective iron-based tris-bypiridyl complex 1DB($Fe^{2+}$) (for the construction of MA1DB) or 2DB($Fe^{2+}$) (for the construction of MA2DB) in $CH_2Cl_2$/MeOH (1:1, v/v) with sonication-wash cycles in between, thereby controlling the electrochemical and photophysical properties of the surface confined architectures. Introducing symmetric 4,4'-bis(vinyl pyridine) bipyridyl ligands on Fe(II), due to its steric constraints, resulted in a slower and linear growth of the assemblies, whereas the one with non-symmetric (4-methyl-4'-vinyl pyridine) bipyridyl analogue grew exponentially. The trend in growth was also reflected on their properties allowing a fine-control of thickness, optical properties, electrochemistry and chromophorism.

The electrochromic behavior of the molecular assemblies was investigated by SEC, wherein the electro-optical response during the switching of potential in a stepwise manner between the oxidized (transmissive) and reduced (colored) states was recorded at the corresponding absorption maxima ($\lambda_{max}$=575 nm for MA1DB and 591 nm for MA2DB) as percentage transmittance (% T) over time, and a superior degree of electro-optic response was evidenced for MA2DB, suggesting an enhanced electrochromic performance and efficiency (Δ% T [$MA1DB_8$]$_{\lambda max=574\ nm}$ (41.3); Δ% T [$MA2DB_8$]$_{\lambda max=591\ nm}$ (33.8)). In view of their vibrant switching from coloured to transmissive states, and consequently their potential for applications in ECDs, the electrochemical stability of the assemblies were followed by CV and SEC in $TBAPF_6$-propylene carbonate electrolyte solution over time. The CV of MA2DB after every few thousands of continuous spectroelectrochemical switching cycles confirmed its ultra-high stability. No detectable decrease in the maximum current (in both oxidative and reductive directions) was observed at least until 112,000 cycles. The decrease in Δ% T was found to be negligible (compared to maximum Δ% T) after 30,000 redox cycles. MA1DB was found to electrochemically less stable compared to MA2DB. The electrochemical stability of MA2DB was further proved by repeating the same experiments (for 30,000 cycles) over 6 days with continuous exposure to UV/vis light and intentional stoppage of cycling for periods ranging from a few minutes to 10 hours, and leaving the assembly in the electrolyte solution for the whole duration. The extra stability of MA2DB over MA1DB could be justified by the larger number of binding sites; and the extended delocalization of electrons and the positive charge over a larger chain of the ligands, which in turn reduces the susceptibility of coordination based systems to dissociate, as explained by the anodic shift in the $E_{1/2}$ of MA2DB.

We also fabricated various gel electrolyte-based SELDs of multi-component metal-organic CPNFs capable of switching colors efficiently, with applied potential difference.

One of the key parameters determining the performance and power efficiency of any ECD is its coloration efficiency (CE), which is defined as the change in optical density (ΔOD) per unit charge injected/ejected per unit area of the electrode, and calculated as:

$$\Delta OD = \log(T_{colored}/T_{bleached})$$
$$CE(\eta) = \frac{\log(T_{colored}/T_{bleached})}{Q_d}$$

where $T_{colored}$ and $T_{bleached}$ are the transmittance in colored (reduced) and bleached (oxidized) states, respectively, and $Q_d$ is the total injected or ejected charge per unit area.

The coloration efficiency of the assemblies MA1DB and MA2DB after 8 deposition cycles were calculated at their MLCT $\lambda_{max}$ and were found to be 955 and 1488 $cm^2C^{-1}$, respectively, which are exceptionally high for surface confined coordination-based metal-organic assembles.

In Study 2, pyridine terminated template layers were generated from silane based coupling layers covalently attached to silicon, quartz and glass substrates, and subsequently, four different multi-component MAs, herein identified MA2SB, MA2DB, MA2TB and MA2Mix, were constructed as described in Study 1, via iterative immersion of those functionalized substrates in a solution of the iron-based tris-bypiridyl complex 2SB($Fe^{2+}$) (for the construction of MA2SB); 2DB($Fe^{2+}$) (for the construction of MA2TB); 2TB($Fe^{2+}$) (for the construction of MA2TB); or an equimolar mixture of 2SB($Fe^{2+}$), 2DB($Fe^{2+}$) and 2TB ($Fe^{2+}$) (for the construction of MA2Mix). Using different ligands that coordinate to the Fe centers, the electro-optical properties of the assemblies were controlled. All these assemblies grew linearly and showed electrochemical switchings between colored (reduced) and transmissive (oxidized) states upon application of the right potential. Combined effect of the ligands and experimental parameters (temperature, switching time (=pulse width), overpotential, etc.) modulates the electro-optical signature of these assemblies. The assemblies showed better optical and electrochemical responses at higher temperature (up to 50° C.) and on application of higher overpotential. Higher the temperature, smaller was the response time for all the MAs. At higher switching times (=pulse width), the MAs showed superior electro-optical response. Application of overpotential at low temperature or smaller pulse width also resulted in better spectroelectrochemical properties.

In Study 3, the effect of the molecular structure of the ligands in determining the stability and coloration efficiencies of the coordination based assemblies was determined. MA2DB was found to be electrochemically the most stable in the family and exhibited the highest coloration efficiency. MA2DB was electrochemically stable at lower temperature (10° C.) and at RT, eventhough showed a slightly diminished stability at 40° C. The thermal stability of MA1DB and MA2DB was also very high as no detectable loss in the intensity of MLCT band was observed after 60 days at 70° C. The coloration efficiency for MA2DB (1488 $cm^2C^{-1}$) and MA1DB (955 $cm^2C^{-1}$) are amongst the highest reported values for such coordination based assemblies. The uniformity and color intensity of the assemblies was also found to be superlative.

In a further aspect, the present invention provides a device comprising a substrate having an electrically conductive surface and a layered structure disposed thereon, said layered structure comprising at least one redox-active compound configured to have a predetermined oxidation state being changeable upon subjecting said layered structure to an electric field, wherein exposure of said device to a potential change causes reversible electron transfer, which results in a change in the electrochromic properties of said layered structure with high coloration efficiency, said device having high electrochemical stability when repeatedly exposed to a potential change, wherein said redox-active compound each independently is a tris-bipyridyl complex of the general formula I or an iron-based tris-bipyridyl complex of the general formula II as defined above. Such a device may be used, e.g., in smart windows, electrochromic window, smart mirrors, electrochromic display devices, smart paper, electrochromic goggles, electrochromic helmet, electrochromic paint, or visors.

The term "high electrochemical stability", as used herein with respect to the device of the present invention, refers to the capability of the device to retain high values of % ΔT, i.e., >90%, >95% or >97%, after at least 1,000 but preferably more than 3,000, 5,000 or 10,000, more preferably more than 20,000 or 30,000, electrochemical switching cycles as immersed in an electrolyte solution, and exposed to air and UV light over a period of a few hours to a few days.

In certain embodiments, exposure of the device of the present invention to a potential change causes reversible electron transfer, which results in a change in the electrochromic properties of said layered structure with coloration efficiency higher than 500 $cm^2C^{-1}$, preferably higher than 600 $cm^2C^{-1}$, 700 $cm^2C^{-1}$, 800 $cm^2C^{-1}$, or 900 $cm^2C^{-1}$, more preferably higher than 1000 $cm^2C^{-1}$.

In certain embodiments, the substrate comprised within the device of the present invention is hydrophilic, hydrophobic or a combination thereof.

In certain embodiments, the substrate comprised within the device of the present invention includes a material selected from glass, a doped glass, ITO-coated glass, TCO, silicon, a doped silicon, Si(100), Si(111), $SiO_2$, SiH, silicon carbide mirror, quartz, a metal, metal oxide, a mixture of metal and metal oxide, group IV elements, mica, a polymer such as polyacrylamide and polystyrene, a plastic, a zeolite, a clay, wood, a membrane, an optical fiber, a ceramic, a metalized ceramic, an alumina, an electrically-conductive material, a semiconductor, steel or a stainless steel. In particular such embodiments, said substrate is in the form of beads, microparticles, sub-microparticles, nanoparticles, quantum dots, metal-organic framework, or nanotubes. In more particular such embodiments, said substrate is optically transparent to the ultraviolet (UV), infrared (IR), near-IR (NIR) and/or visible spectral ranges.

As stated above, the device of the present invention comprises a substrate having an electrically conductive surface and carrying a layered structure comprising at least one redox-active compound configured to have a predetermined oxidation state, wherein each redox-active compound independently a transition metal-based tris-bipyridyl complex of the general formula I or an iron-based tris-bipyridyl complex of the general formula II as defined above.

In certain embodiments, the layered structure comprises (i) a monolayer of either one redox-active compound as defined above or two or more, i.e., two, three, four or more, redox-active compounds each as defined above, said redox-active compounds having identical or different metals; or (ii) a plurality of layers each comprising either one redox-active compound as defined above or two or more, i.e., two, three, four or more, redox-active compounds each as defined above, said redox-active compounds having identical or different metals. In particular such devices, said redox-active compound each independently is an iron-based tris-bipyridyl complex of the general formula I or II as defined above, wherein n is 2 or 3.

In particular such embodiments, the layered structure comprises a monolayer of either one redox-active compound or two or more redox-active compounds, or a plurality of layers each comprising either one redox-active compound or two or more redox-active compounds, said redox-active compound each independently is (i) a tris-bipyridyl complex of the general formula I as defined above, wherein M is Fe; n and m each is 2 or 3; $R_1$ to $R_{18}$ each is H; and $A_1$ to $A_6$ each is a group of the formula III, wherein $R_x$ is H and $R_{19}$ is C—C, C=C or C≡C, or a group of the formula IV, wherein $R_y$ is H and $R_{19}$ is C—C, C=C or C≡C; or (ii) an iron-based tris-bipyridyl complex of the general formula II as defined above, wherein n and m each is 2 or 3; $R_1$ to $R_{18}$ each is H; $A_1$, $A_3$ and $A_5$ each is a group of the formula III, wherein $R_x$ is H and $R_{19}$ is C—C, C=C or C≡C, or a group of the formula IV, wherein $R_y$ is H and $R_{19}$ is C—C, C=C or C≡C; and $B_1$ to $B_3$ each is methyl. In more particular such embodiments, X is $PF_6^-$.

The device of the present invention, in any one of the embodiments defined above, can be used in smart windows, electrochromic windows, smart mirrors, optical filters, frequency doubling devices, optical switches, modulators, spatial light modulators, phase masks, data transfer devices, data storage devices, pulse shapers, optical processors, electrochromic display devices, smart papers, electrochromic goggles, electrochromic helmets, electrochromic paints, or visors.

In particular embodiments, the device is used in smart or electrochromic windows, wherein said layered structure comprises a plurality of layers each comprising either one redox-active compound or two or more redox-active compounds, said redox-active compound each independently is (i) a tris-bipyridyl complex of the general formula I as defined above, wherein M is Fe; n and m each is 2 or 3; $R_1$ to $R_{18}$ each is H; and $A_1$ to $A_6$ each is a group of the formula III, wherein $R_x$ is H and $R_{19}$ is C—C, C=C or C≡C, or a group of the formula IV, wherein $R_y$ is H and $R_{19}$ is C—C, C=C or C≡C; or (ii) an iron-based tris-bipyridyl complex of the general formula II as defined above, wherein n and m each is 2 or 3; $R_1$ to $R_{18}$ each is H; $A_1$, $A_3$ and $A_5$ each is a group of the formula III, wherein $R_x$ is H and $R_{19}$ is C—C, C=C or C≡C, or a group of the formula IV, wherein $R_y$ is H and $R_{19}$ is C—C, C=C or C≡C; and $B_1$ to $B_3$ each is methyl. In more particular such embodiments, X is $PF_6^-$.

The device of the present invention, in any one of the embodiments defined above, can also be used as a memory device.

In yet another aspect, the present invention thus provides a memory device comprising a substrate having an electrically conductive surface and a layered structure disposed thereon, said layered structure comprising at least one redox-active compound configured to have at least one a predetermined electronic property, including at least one of electrodensity and oxidation state, said predetermined electronic property being changeable upon subjecting said layered structure to an electric field, wherein said redox-active compound each independently is a tris-bipyridyl complex of the general formula I or an iron-based tris-bipyridyl complex of the general formula II as defined above.

The term "electrodensity", as used herein and also known as "electron density", refers to the measure of the probability of an electron being present at a specific location.

The invention will now be illustrated by the following non-limiting Examples.

Examples

Materials and Methods

Most reagents were purchased from Sigma Aldrich, BDH or Merck. All chemicals were used as received. Solvents (Reagent Grade) were purchased from Bio-Lab (Jerusalem), Sigma Aldrich, and Merck. Toluene was dried using an M. Braun solvent purification system and degased with argon for 30 minutes before introducing into a nitrogen filled glove box. All reaction vessels were cleaned with piranha solution (7:3 (v/v) $H_2SO_4$:30% $H_2O_2$) for 20 minutes (caution: piranha is an extremely dangerous oxidizing agent and should be handled with care using appropriate personal protection), washed with excess of water, acetone and dried for at least 5 hours in an air oven at 130° C. Monolayers were prepared and characterized as previously reported (Motiei et al., 2008) with slight changes in the cleaning procedure. Single crystal silicon (100) substrates were purchased from Wafernet (San Jose, Calif.) and were cleaned (10×20 mm) by sonication for 8 minutes each in $CH_2Cl_2$, n-hexane, acetone and ethanol followed by drying under a flow of nitrogen and subsequent treatment in a UVOCS cleaning system (Montgomery, Pa.) for 30 minutes, washings with ethanol and sonication. ITO coated glass slides (unpolished Float Glass, 7×50×0.5 mm, $SiO_2$ passivated/ ITO coated two surfaces, $R_s$=8-12Ω) were purchased from Delta Technologies Ltd. (Loveland, Colo.) and were cleaned via exactly the same procedure as described above. Quartz slides were purchased from Chemglass Life Sciences (USA) and were cleaned by washing several times with deionized (DI) water, followed by immersion in a piranha solution (7:3 (v/v) $H_2SO_4$: 3% $H_2O_2$) for 1 hour. Thereafter, the glass substrates were rinsed with deionized water and cleaned for 1 hour using the Radio Corporation of America (RCA) cleaning protocol (1:5:1 (v/v) $NH_4OH$:$H_2O$:30% $H_2O_2$). Subsequently, the substrates were rinsed with ethanol, dried under a $N_2$ flow and all the substrates (Silicon, ITO coated glass and quartz) oven dried for at least 3 hours at 130° C.

UV/vis spectra were recorded at RT, unless stated otherwise, on a Cary 100 spectrophotometer in transmission mode (200-800 nm). The functionalised quartz substrates were fixed in a Teflon holder (1.5×0.75 cm window) and an identical quartz substrate without monolayer was used to compensate for the background absorption.

$^1H$, $^{13}C$ ($^1H$), $^{19}F$ and $^{31}P$ NMR spectra were recorded on a Bruker 300 MHz NMR spectrometer. Atomic Force Microscope (P47 Solver AFM (NT-MDT, Zelenograd, Russia)) in intermittent contact/tapping mode, using AC240 probes (Olympus) in intermittent contact/tapping mode) was used to estimate the roughness of the MAs as well as film morphologies. Film thickness was estimated on silicon substrates using a J.A. Woollam (Lincoln, Nebr.) model M-2000 V variable angle spectroscopic ellipsometer with the VASE32 software. XRR measurements were performed at BeamlineX6B of the National Synchrotron Light Source, Brookhaven (Upton, N.Y.) using a four-circle Huber diffractometer in the specular reflection mode (i.e., incident angle I was equal to the exit angle).

Electrochemical measurements, unless otherwise stated, were performed using a potentiostat (CHI660A) and a three-electrode cell configuration consisting of (a) an ITO modified substrate (working electrode), (b) Ag/Ag$^+$ (reference electrode) and (c) a Pt wire (counter electrode), at RT using 0.1 M solution of tetrabutylammoniumhexafluoro phosphate ($Bu_4NPF_6$) in anhydrous $CH_3CN$ or propylene carbonate ($H_2O$<0.001% v/v) (both were purchased from Sigma Aldrich).

The experimental data were fitted to the expression $y=y_0+c_1\exp(c_2x)$ or $y=y_0+c_1\exp(c_2x)+c_3\exp(c_4x)$, for exponential fits and $y=a+bx$, for linear fits, where y is the measured absorption, thickness, current, charge or intensity after x deposition steps or at a particular experimental condition, $c_1$, $c_2$, $c_3$ and $c_4$ are fitting parameters, a is a constant and b is the slope of the linear fit. Similar fitting models have earlier been used.

Synthesis of 4-[2-(4-pyridyl)ethenyl]-4'-methyl-2,2'-bipyridine (ligand L1DB)

As demonstrated in Scheme 1, ligand L1DB was synthesized from 4,4'-dimethyl-2,2'-bipyridine 1 in a two-step reaction involving its deprotonation and attack on pyridine-4-carboxaldehyde, followed by dehydration (Choudhury el al., 2010). In particular, to a solution of di-isoproplylamine (2.83 ml, 20 mmol) in freshly distilled THF (10 ml) was added dropwise nBuLi (12.5 ml, 20 mmol, 1.6 M solution in hexanes) at −20° C. under an inert atmosphere. The solution was stirred for an additional 15 min, where after 4,4'-dimethyl-2,2'-bipyridine (3.7 g, 20 mmol) in 120 ml THF was added drop wise, where upon the color changed to dark red-brown. After 2 h, a solution of pyridine-4-carboxaldehyde (1.89 ml, 20 mmol) in 15 ml THF was added which resulted in a color change from red-brown to yellow-green. The solution was stirred for 2 h at −20° C., and allowed to warm to RT overnight. The reaction was quenched with water (20 ml) and the THF evaporated under reduced pressure. The resulting solution was extracted with $CH_2Cl_2$ (3×150 ml). The organic fractions were pooled together, dried with $Na_2SO_4$ and the solvent was removed under reduced pressure to yield a crude yellow solid (5.04 g). The yellow solid was dissolved in dry pyridine (50 ml) at 0° C. and a solution of $POCl_3$ (2.25 ml, 0.25 mmol) in 16 ml dry pyridine was added during the course of 30 min. Upon addition, the mixture turned dark red. An additional amount of $POCl_3$ (0.75 ml) was added, and the mixture was stirred for an additional 4 hours at RT. The pyridine was removed under reduced pressure, and ice-water was added to destroy any excess of $POCl_3$. The aqueous solution was stirred for 30 min., before the pH was adjusted to 7-8. The solution was extracted with $CH_2Cl_2$ (4×150 ml). The extracts were pooled together and dried with $Na_2SO_4$. The solvent was removed under reduced pressure and the crude product was purified by column chromatography (neutral alumina, G-II) to afford 4-[2-(4-pyridyl)-2-ethenyl]-4'-methyl-2,2'-bipyridine (L1DB) as an off white solid (4.06 g, 74%). $^1$H NMR (400 MHz, $CDCl_3$) δ 8.68 (d, J=5.1 Hz, 1H), 8.6 (dd, J=1.6, 4.6 Hz, 2H), 8.56-8.59 (m, 2H), 8.28 (s, 1H), 7.42 (dd, J=1.6, 4.6 Hz, 2H), 7.39 (dd, J=1.7, 5.1 Hz, 1H), 7.34 (AB ethenyl, J=16.5 Hz, 2H), 7.18 (d, J=5.0 Hz, 1H), 2.46 (s, 3H); ESI-MS 274.46 $[M+H]^+$, 296.54 $[M+Na]^+$.

Synthesis of 4,4'-bis((E)-2-(pyridin-4-yl)vinyl)-2,2'-bipyridine (ligand L2DB)

Two different routes have been envisaged for the synthesis of ligand L2DB, both starting from the commercially available 4,4'-dimethyl-2,2'-bipyridine. The initial synthetic strategy consists of two steps as in the synthesis of L1DB, but with low overall yield (Choudhury et al., 2010); and the second one is a multi-step protocol with higher overall yields (Oki and Morgan, 1995; Gillaizeau-Gauthier et al., 2001; Coe et al., 2010). Route 1: Deprotonation of the methyl groups in 4,4'-dimethyl-2,2'-bipyridine 1, followed by nucleophilic attack on pyridine-4-carboxaldehyde gave the corresponding diol in 71% yield. The crude diol was then double-dehydrated using pyridine-$POCl_3$ to yield the ligand L2DB in 6-8% overall yield. Route 2: Oxidation of the methyl groups in 4,4'-dimethyl-2,2'-bipyridine 1 using chromic acid yielded the diacid 3 in 95% yield, which was esterified and subsequently reduced to give the corresponding diol 5. The diol on reaction with HBr—$H_2SO_4$ gave the dibromide 6 in 85% yield, which on further treatment with triethyl phosphite gave the corresponding bisphosphonate 7. The addition of pyridine-4-carboxaldehyde 2 in presence of a base under anhydrous conditions yielded the ligand L2DB in near quantitative yield (overall yield 46% over 6 steps).

Synthesis of Ligand L2DB According to Route 1

As demonstrated in Scheme 1, to a solution of di-isopropylamine (11.8 ml, 83.6 mmol) in freshly distilled THF (50 ml) was added dropwise nBuLi (52.2 ml, 83.6 mmol, 1.6 M solution in hexanes) at −20° C. under an inert atmosphere. The solution was stirred for an additional 15 min, where after 4,4'-dimethyl-2,2'-bipyridine (7 g, 38 mmol) in 250 ml THF was added drop wise, where upon the color changed to dark red-brown. After 2 h, a solution of pyridine-4-carboxyaldehyde 2 (7.9 ml, 83.6 mmol) in 40 ml THF was added which resulted in a color change from red-brown to yellow-green. The solution was stirred for 2 h at −20° C., and allowed to warm to RT overnight. The reaction was quenched with water (100 ml) and THF evaporated under reduced pressure. The resulting solution was extracted with $CH_2Cl_2$ (3×400 ml). The organic fractions were pooled together, dried with $Na_2SO_4$ and the solvent was removed under reduced pressure to yield a crude yellow solid (10.79 g, 71%) and was used in the next step without further purification or characterization. The yellow solid (10.79 g, 23.1 mmol) was dissolved in dry pyridine (100 ml) and a solution of $POCl_3$ (7.6 ml, 81.2 mmol) in 40 ml dry pyridine was added during the course of 30 min. Upon addition, the mixture turned dark red. An additional amount of $POCl_3$ (2.5 ml, 27.1 mmol) was added, and the mixture was stirred for another 4 hours. Pyridine was removed under reduced pressure, and ice was added to quench excess $POCl_3$. The aqueous solution was stirred for 30 min., before the pH was adjusted to 7-8 using NaOH. The solution was extracted with $CH_2Cl_2$ (4×250 ml). The extracts were pooled together and dried with $Na_2SO_4$. The solvent was removed under reduced pressure and the crude product was purified by column chromatography (3-5% MeOH/$CHCl_3$+0.5% $Et_3N$ as eluent) to afford L2DB as an off white solid (1.01 g, 12%). $^1$H NMR ($CDCl_3$) δ: 8.72 (2H, d, J=5.1 Hz), 8.64 (4H, d, J=6.1 Hz), 8.60 (s, 2H), 7.45-7.41 (6H, m), 7.39 (2H, d, J=16.5 Hz), 7.32 (2H, d, J=16.4 Hz). ESI-MS 363.13 $[M+H]^+$, 385.13 $[M+Na]^+$, 747.07 $[2M+Na]^+$ (For complete data, see Coe et al., 2010).

Synthesis of Ligand L2DB According to Route 2

As demonstrated in Scheme 2, to a stirred solution of 4,4'-dimethyl-2,2'-bipyridine 1 (10 g, 41 mmol) in sulfuric acid (95-98%, 250 ml) at 0° C. was added potassium dichromate (48 g, 163 mmol) in small portions over 20 min. The inside temperature of the mixture was maintained at 70-80° C. by occasional cooling using ice/water bath. The resultant mixture was stirred at RT until the inside temperature fell below 40° C. (3-4 h) while the color turned deep green. The reaction mixture was poured into ice, filtered and washed with cold water until the filtrate became colorless. The solid was dried, refluxed in 50% $HNO_3$ for 4 h and the solution was poured over ice and diluted with water (2 l). The aqueous mixture was cooled to <5° C. and the precipitate was filtered, washed with water (4×100 ml), acetone (3×30 ml) and dried to give [2,2'-bipyridine]-4,4'-dicarboxylic acid 3 as an off-white solid (9.51 g, 95%). The crude product obtained was used in the next step without further characterization or purification.

To a suspension of the diacid 3 (9.51 g, 39 mmol) in 1 l of absolute ethanol was added concentrated sulfuric acid (20 ml, 95-98%). The suspension was kept under reflux for 2 days to obtain a clear solution and then cooled to RT. The mixture was poured into ice was added and excess ethanol removed under vacuum. The pH was adjusted to neutral with 2M NaOH solution, and the resulting precipitate was filtered, washed with water (5×200 ml) and dried to obtain the diester diethyl [2,2'-bipyridine]-4,4'-dicarboxylate 4 as a yellowish-white solid (10.41 g, 89%). $^1$H NMR (300 MHz, $CDCl_3$) δ 8.98-8.92 (m, 2H), 8.87 (d, J=4.9 Hz, 2H), 7.91 (dd, J=5.0, 1.6 Hz, 2H), 4.45 (q, J=7.1 Hz, 4H), 1.44 (t, J=7.1 Hz, 6H). $^{13}$C NMR (75 MHz, $CDCl_3$) δ 165.4, 156.7, 150.4, 139.4, 123.7, 121.0, 62.3, 14.6. ESI-MS 301.11 $[M+H]^+$, 323.11 $[M+Na]^+$, 623.14 $[2M+Na]^+$.

To a suspension of the diester 4 (10.0 g, 33.3 mmol) in 300 ml of absolute ethanol was added sodium borohydride (25.19 g, 665.9 mmol) in one portion. The mixture was refluxed for 3 h and cooled to RT, and excess borohydride was decomposed by the dropwise addition saturated ammonium chloride solution (300 ml). Ethanol was removed under vacuum and the precipitated solid was filtered and the solid was dissolved in ethyl acetate (400 ml), washed with water (100 ml), dried over anhy. $Na_2SO_4$ and the solvent was removed under vacuum to yield the diol [2,2'-bipyridine]-4,4'-diyldimethanol 5 as a white powder (5.9 g, 82%). $^1H$ NMR (300 MHz, $CD_3OD$) δ 8.63-8.56 (m, 2H), 8.30-8.21 (m, 2H), 7.53-7.38 (m, 2H), 4.76 (s, 4H). $^{13}C$ NMR (75 MHz, $CD_3OD$) δ 157.2, 154.3, 150.2, 122.7, 120.2, 63.6. ESI-MS 217.08 $[M+H]^+$, 239.02 $[M+Na]^+$, 455.20 $[2M+Na]^+$.

A solution of the diol 5 (10.0 g, 46.2 mmol) in a mixture of HBr (48%, 200 ml) and concentrated $H_2SO_4$ (95-98%, 67 ml) was refluxed for 6 h and then allowed to cool to RT. Water (400 ml) was then added to the mixture and the pH was adjusted to neutral with 2M NaOH solution. The resulting precipitate filtered, washed with water (4×100 ml), and dried. The solid was dissolved in chloroform (200 ml) and filtered. The solution was dried over anhy. $Na_2SO_4$ and the solvent was removed under vacuum, yielding the dibromide 4,4'-bis(bromomethyl)-2,2'-bipyridine 6 (13.5 g, 85.4%) as an off-white powder. $^1H$ NMR (300 MHz, $CDCl_3$) δ 8.72 (d, J=5.1 Hz, 2H), 8.58 (s, 2H), 7.47 (d, J=5.1 Hz, 2H), 4.52 (s, 4H). $^{13}C$ NMR (75 MHz, $CDCl_3$) δ 154.2, 149.2, 149.0, 124.8, 122.2, 30.4. ESI-MS 342.90 $[M+H]^+$, 364.84 $[M+Na]^+$, 706.63 $[2M+Na]^+$.

To a solution of the dibromide 6 (12.0 g, 35.1 mmol) in dry chloroform (100 ml) was added triethyl phosphite (100 ml) and the resulting mixture was refluxed for 3 h under nitrogen. The excess phosphite was removed under high vacuum, and the remaining solid was purified by flash chromatography (Silica gel, 4-8% MeOH/$CHCl_3$ as eluent) yielding the bisphosphonate tetraethyl ([2,2'-bipyridine]-4,4'-diylbis(methylene))bis(phosphonate) 7 as a yellowish-white solid (13.0 g, 81%). $^1H$ NMR (300 MHz, $CDCl_3$) δ 8.60 (d, J=5.1 Hz, 2H), 8.38 (s, 2H), 7.37-7.32 (m, 2H), 4.05 (dq, J=14.2, 7.1 Hz, 8H), 3.23 (d, J=22.3 Hz, 4H), 1.24 (t, J=7.1 Hz, 12H). $^{13}C$ NMR (75 MHz, $CDCl_3$) δ 154.9, 148.8, 143.4, 125.5, 125.4, 123.1, 123.0, 62.6, 62.53, 34.7, 32.8, 16.5, 16.4. $^{31}P$ NMR (121 MHz, $CDCl_3$) δ 25.40. ESI-MS 457.10 $[M+H]^+$, 479.04 $[M+Na]^+$, 935.07 $[2M+Na]^+$, 1391.10 $[3M+Na]^+$, 455.20 $[M-H]^-$.

To a stirred solution of the bisphosphonate 7 (11.8 g, 25.8 mmol) in dry THF (400 ml) under $N_2$, potassium tert-butoxide (7.25 g, 64.6 mmol) was added, followed by pyridine-4-carboxaldehyde (5.5 ml, 58.2 mmol). The mixture was stirred in the dark at RT for 3 h. after which triple distilled water (400 ml) was added, and was stirred for another 2 min. The solid was filtered off, washed with water (5×100 ml) and diethyl ether (3×50 ml), and dried under vacuum to give ligand L1DB (9.0 g, 96%) as an off-white solid. $^1H$ NMR (300 MHz, $CD_3OD$) δ 8.71-8.67 (m, 2H), 8.56 (dd, J=4.7, 1.6 Hz, 4H), 8.54 (d, J=0.9 Hz, 2H), 7.59 (dd, J=4.8, 1.6 Hz, 4H), 7.52 (dd, J=5.2, 1.7 Hz, 2H), 7.44 (s, 4H). $^{13}C$ NMR (75 MHz, $CD_3OD$) δ 156.2, 149.9, 148.7, 146.0, 145.2, 132.3, 130.8, 122.4, 122.3, 119.4. ESI-MS 363.13 $[M+H]^+$, 385.13 $[M+Na]^+$, 747.07 $[2M+Na]^+$.

Synthesis of Ligand L2SB and L2TB

The synthesis of ligands L2SB and L2TB was carried out as demonstrated in Scheme 3, starting from ligand L2DB and based on the procedure for the synthesis of 1,2-bis(4-pyridyl)acetylene (Nugent et al., 2013).

To a solution of L2DB (1.0 g, 2.76 mmol) in MeOH—AcOEt (1:1 v/v, 15 ml) inside a Fisher-Porter tube, was added 5 wt % Pd—C (50 mg). The resulting mixture was stirred under $H_2$ (8 bar) for 12 h. with the exclusion of light. The mixture was then filtered over celite, and washed with MeOH—AcOEt (1:1 v/v, 15 ml). The filtrate was evaporated under reduced pressure to obtain L2SB as an off-while solid (990 mg, 98%). $^1H$ NMR (300 MHz, $CDCl_3$) δ 8.47 (d, J=5.0 Hz, 2H), 8.36 (dd, J=4.7, 1.2 Hz, 4H), 8.14 (s br, 2H), 7.20-7.07 (m, 4H), 7.06 (dd, J=5.0, 1.5 Hz, 2H), 2.98 (s, 8H). $^{13}C$ NMR (75 MHz, $CDCl_3$) δ 155.9, 151.0, 150.6, 149.1, 149.0, 124.2, 124.1, 121.4, 35.8, 35.6. ESI MS 367.18 [M+H], 389.19 [M+Na], 755.25 [2M+Na].

To a stirred solution of L2DB (1.0 g, 2.76 mmol) in HBr (48%, 15 ml) at 0° C., $Br_2$ (1.05 ml, 19.3 mmol) was added dropwise. The mixture was then heated to 120° C. and stirred for 2 hours. Subsequent cooling to room temperature yielded a dark orange precipitate. After chilling in an ice-acetone bath for 1 h, the solid was filtered, washed with water (3×50 ml). An aqueous solution of NaOH (2 M, 50 ml) was added to the solid and was stirred for 30 min. The resulting off-white solid was filtered, washed with water (3×100 ml), and dried under vacuum for 24 hours to give the dibromo adduct 8 (1.6 g, 85%). $^1H$ NMR (300 MHz, DMSO) δ 8.87 (d, J=5.1 Hz, 2H), 8.78-8.71 (m, 6H), 7.83 (d, J=6.2 Hz, 6H), 6.39 (dd, J=28.4, 11.9 Hz, 4H). $^{13}C$ NMR (75 MHz, DMSO) δ 155.5, 150.2, 150.0, 149.6, 123.5, 123.4, 123.1, 119.9, 51.1, 51.0. MS (Maldi-TOF) 683.2 [M+H], 682.21 [M], 599.25, 601.26, 603.26, 605.27, 606.27, 609.31 [M-Br], 517.14, 520.17, 521.17, 523.33, 525.33, 526.34, 527.34, 529.37, 532.39 [M-2Br].

Finely cut pieces of Na (454 mg, 19.7 mmol) was added t-BuOH (20 ml, dried over 4 Å molecular sieves for 3 days) and was heated to 80° C. under nitrogen for 24 h until complete dissolution. The dibromo adduct obtained above (897 mg, 1.3 mmol) was added in four portions over 15 min and the mixture was stirred at 80° C. for 6 hrs. The mixture was then allowed to cool to RT and dry EtOH (10 ml) was added dropwise, followed by water (10 ml, caution: any left-over sodium can react violently with water) using a dropping funnel. The resultant mixture was extracted with $CHCl_3$ (50 ml) until the extracts became colorless (6×). The combined extracts were dried over $Na_2SO_4$ and then evaporated under reduced pressure. The light brown solid was dissolved in $CH_2Cl_2$ (10 ml) and $Et_3N$ (300 □l) was added and evaporated to dryness to obtain L2DB as an off-white solid (300 mg, 64%). $^1H$ NMR (400 MHz, $CDCl_3$+MeOD) δ 8.67 (dd, J=5.0, 0.7 Hz, 2H), 8.55 (dd, J=4.5, 1.6 Hz, 4H), 8.48 (dd, 0.1=1.3, 0.8 Hz, 2H), 7.45-7.40 (m, 6H). $^{13}C$ NMR (101 MHz, $CDCl_3$+MeOD) δ 155.6, 149.8, 149.5, 131.5, 130.9, 126.0, 125.9, 123.6, 91.2, 90.7. ESI-MS 359.13 [M+H], 381.14 [M+Na], 739.15 [2M+Na].

Synthesis of Iron Polypyridyl Complexes 1DB($Fe^{2-}$), 2DB($Fe^{2+}$), 2SB($Fe^{2+}$) and 2TB($Fe^{2+}$)

To a solution of $FeCl_2 \cdot 4H_2O$ (1.1 equiv., 0.36 mmol) in MeOH (10 ml) was added a solution of the corresponding ligand L1DB, L2DB, L2SB or L2TB (3 equiv., 0.98 mmol) in MeOH (10 ml). The solution was then stirred for 30 minutes, with occasional warming to 50° C. (every 10 minutes) and filtered. The filtrate was then concentrated to half its initial volume and an aqueous solution (50 ml) of $NH_4PF_6$ (320 mg, 1.96 mmol, 6 equiv.) was added. The precipitate was filtered and washed with water (3×25 ml) and ether (25 ml), and was dried to obtain the corresponding Fe complex as its $PF_6$ salt in near quantitative yield. Complex 1DB($Fe^{2+}$) ([Fe(L1DB)$_3$](PF$_6$)$_2$): $^1H$ NMR (400 MHz, $(CD_3)_2CO$) δ 9.09 (t, J=4.1 Hz, 1H), 8.82 (br s, 1H), 8.67-8.62 (m, 2H), 7.86 (dd, J=12.8, 5.8 Hz, 1H), 7.81 (d, J=4.4 Hz, 1H), 7.77-7.68 (m, 3H), 7.64-7.60 (m, 2H), 7.47 (br d, J=4.9 Hz, 1H), 2.64 (d, J=4.5 Hz, 3H); ESI/MS: 1020.44 $[MPF_6]^+$, 144.71 ($PF_6^-$). Elemental Analysis: Calc. C, 52.40; H, 4.32; N, 10.18. Found C, 51.81; H, 3.98; N, 10.20. Complex 2DB($Fe^{2+}$) ([Fe(L2DB)$_3$](PF$_6$)$_2$): $^1H$ NMR (400 MHz, MeOD+$CD_2Cl_2$) δ 8.97 (s, 2H), 8.52 (d, J=5.7

Hz, 4H), 7.71 (d, 0.1=16.4 Hz, 2H), 7.61-7.58 (m, 6H), 7.53 (d, J=16.5 Hz, 2H), 7.45 (d, J=6.1 Hz, 2H). $^{13}$C NMR (101 MHz, MeOD+CD$_2$Cl$_2$) δ 160.1, 154.2, 150.3, 147.7, 144.5, 134.9, 129.4, 125.6, 122.6, 122.1. $^{19}$F{$^1$H} NMR (282 MHz, CDCl$_3$+MeOD) δ −76.09 (d, 0.1=710.3 Hz); ESI/MS: 1143.52 [M-2PF$_6$+H]$^+$, 144.90 [PF$_6$]. Complex 2SB(Fe$^{2+}$) ([Fe(L2SB)$_3$](PF$_6$)$_2$): $^1$H NMR (400 MHz, MeOD+CD$_2$Cl$_2$) δ 8.42 (d, 0.1=1.0 Hz, 2H), 8.34 (dd, J=4.5, 1.5 Hz, 4H), 7.23 (dd, J=4.7, 1.4 Hz, 6H), 7.10 (d, 0.1=5.9 Hz, 2H), 3.17-3.13 (m, 4H), 3.07-3.03 (m, 4H). $^{13}$C NMR (101 MHz, MeOD+CD$_2$Cl$_2$) δ 159.6, 154.5, 153.7, 151.3, 149.6, 128.4, 125.0, 124.9, 35.9, 35.4. $^{19}$F NMR (282 MHz, MeOD) δ −73.59 (d, J=710.8 Hz). ESI MS 577.62 [M-2PF$_6$]$^{2+}$, 1299.6 [M-PF$_6$], 1154.73 [M-2PF$_6$], 144.90 [PF$_6$]. Complex 2TB (Fe$^{2+}$) ([Fe(L2TB)$_3$](PF$_6$)$_2$): 1H NMR (400 MHz, MeOD+CD$_2$Cl$_2$) δ 8.85 (d, J=1.1 Hz, 2H), 8.59 (dd, J=4.6, 1.6 Hz, 4H), 7.61 (dd, J=6.0, 1.6 Hz, 2H), 7.54 (dd, J=4.5, 1.7 Hz, 4H), 7.50 (d, 1=5.8 Hz, 2H). $^{13}$C NMR (101 MHz, MeOD+CD$_2$Cl$_2$) δ 158.9, 154.57, 150.1, 134.3, 130.3, 130.2, 126.7, 126.6, 96.2, 89.1. $^{19}$F NMR (282 MHz, MeOD+CD$_2$Cl$_2$) δ −74.12 (d, J=710.2 Hz). ESI MS 565.32 [M-2PF$_6$]$^{2+}$, 1275.96 [M-PF$_6$], 144.84 [PF$_6$].

A complex similar to complex 2DB(Fe$^{2+}$), in which each one of the nitrogen atoms of the six terminal pyridine groups (each represented by the group A in the general formula I) is substituted by methyl ([FeII(Me$_2$bbpe$_2^+$)$_3$][PF$_6$]$_8$), has already been disclosed (Coe et al., 2010). According to Coe et al., FeII(BF$_4$)$_2$.6H$_2$O was added to a solution of [Me$_2$bbpe$_2^+$]-[PF$_6$]$_2$.0.8H$_2$O in DMF (10 ml), and the deep blue solution was stirred at RT for 2 hours in the dark. Addition of aqueous NH$_4$PF$_6$ afforded a dark blue precipitate, which was filtered off, washed with water, and dried. Purification was effected by column chromatography to afford a dark blue solid.

Nevertheless, complexes as disclosed in Coe et al. are completely different both in structure and electronic, optical and electrochemical properties from the complex of the formula I. In particular, while the complex reported in Coe et al. consists of six pyridinium salts, wherein the overall charge of the complex is 8$^+$, the tris-bypiridyl complex of the general formula I has free pyridine (or pyrimidine) groups, wherein the overall charge is 2$^+$. Moreover, a complex as described in Coe et al. cannot form a network structure as it has no free binding sites for metal salts.

Furthermore, prima facie, it seems that a tris-bypiridyl complex of the general formula I such as complex 2DB (Fe$^{2+}$) cannot even be synthesized according to the procedure of Coe et al., considering that this complex is not very stable in DMF and some sort of ligand exchange may occur if left in DMF for some time. Moreover, while the complex of Coe et al. should be purified by column chromatography, the procedure described herein for the synthesis of a complex of the general formula I gives the product instantaneously, wherein the yield is quantitative and no further purification is required.

Single Electrochrome Laminated Devices (SELD)

Preparation of the gel electrolyte. Polymethylmethacrylate (PMMA, 700 mg), trifluoromethylsulfonamide lithium salt (300 mg), acetonitrile (dry, 7 g, ~8.9 ml) and propylene carbonate (dry, 2 g, 1.7 ml), in a weight percentage composition of 70:20:7:3, were added to an oven-dried glass vessel under inert atmosphere and stirred vigorously for 12 hours, giving a homogeneous casting electrolyte solution.

Device Fabrication and Measurements.

The modified ITO substrate was cleaned by rinsing in ethanol and drying under a flow of nitrogen. The electrolyte solution was then carefully drop-casted on to the corresponding modified ITO substrate and was kept in an air oven at 55° C. for 10 minutes. This ITO substrate was placed on top of a clean bare ITO coated glass substrate in such a way that the gel electrolyte was sandwiched between the substrates and was held tight with an insulating 2-sided sticking tape at each ends (to prevent short circuits as well as to hold the setup together). The ends were then connected to a potentiostat and the electrochromic property of the solid-state set-up was studied.

Figure 2A:
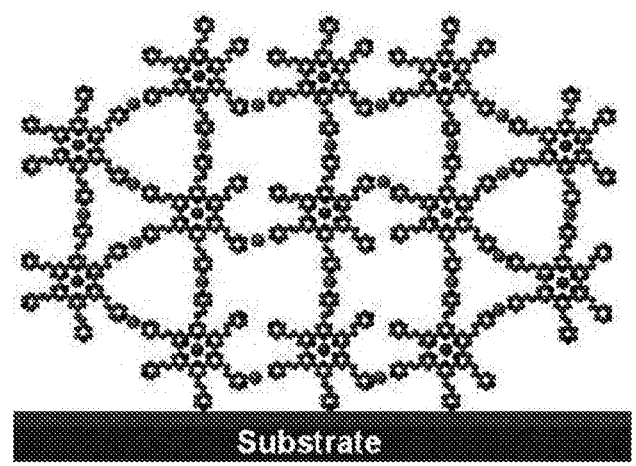
FIG. 2 shows the formation of the MAs. Schematic representation of (2A) a fully formed network via linear growth and (2B) a self-propagating molecular assembly via exponential growth.
Figure 2B:
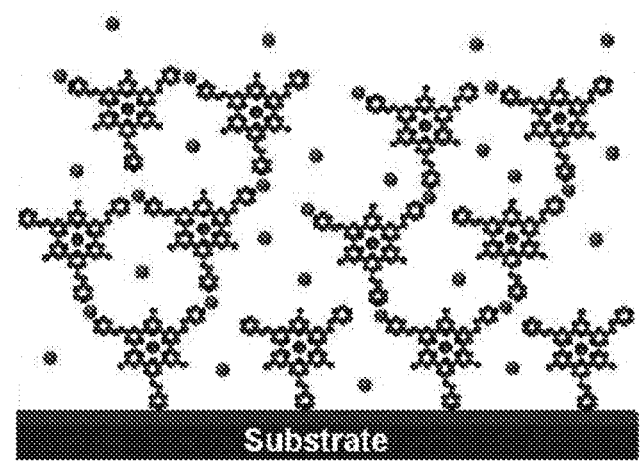

Study 1. Molecular Assemblies Based on Complexes 1DB (Fe$^{2+}$) and 2DB(Fe$^{2+}$), and their Electrochromic Behavior Pyridine terminated template layers (TLs) were generated from silane based coupling layers (CLs) covalently attached to silicon, quartz and glass substrates (FIG. 1) via a slight modification of the procedure previously reported (Motiei el al., 2008). Subsequently, two different multi-component MAs, herein identified MA1DB and MA2DB, were constructed via iterative immersion of these functionalized substrates for 15 minutes each in a 1 mM solution of PdCl$_2$(PhCN)$_2$ in THF and 0.2 mM solution of the respective iron polypyridyl complex 1DB(Fe$^{2+}$) (for the construction of MA1DB) or 2DB(Fe$^{2+}$) (for the construction of MA2DB) in CH$_2$Cl$_2$/MeOH (1:1, v/v) with sonication-wash cycles (3 minutes) in between (FIG. 2). Both the MAs were followed by ex-situ transmission UV/Vis Spectroscopy and ellipsometry and characterized by AFM, synchrotron XRR and XPS measurements.

Figure 3A:
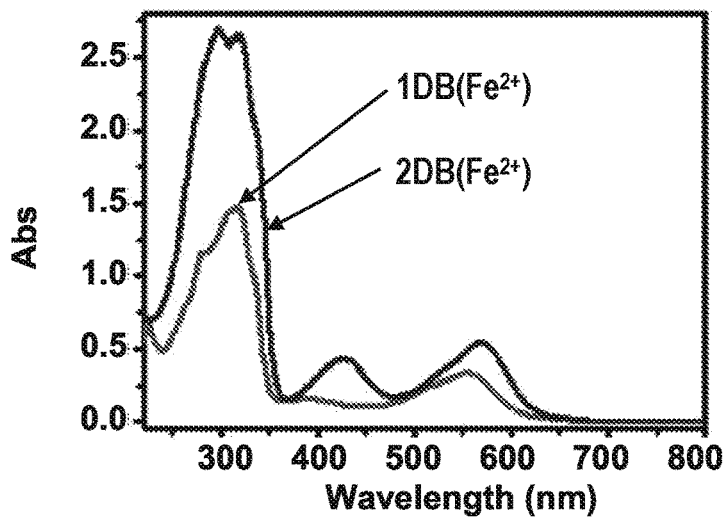
FIGS. 3A-3C show (3A) UV/vis spectra of 15 μM solutions of complexes 1DB(Fe$^{2+}$) and 2DB(Fe$^{2+}$) in CH$_2$Cl$_2$/MeOH (1:1, v/v); (3B) CVs of 15 μM solutions of complexes 1DB(Fe$^{2+}$) and 2DB(Fe$^{2+}$) in 0.1 M Bu$_4$NPF$_6$/MeCN electrolyte solution at room temperature using glassy carbon as the working electrode, Ag/Ag$^+$ as the reference electrode and Pt wire as the counter electrode at a scan rate of 100 mVs$^{-1}$; and (3C) differential-pulsed voltammetry (DPV) of 15 μM solutions of complexes 1DB(Fe$^{2+}$) and 2DB(Fe$^{2+}$) under the same conditions as (3B).
Figure 3B:
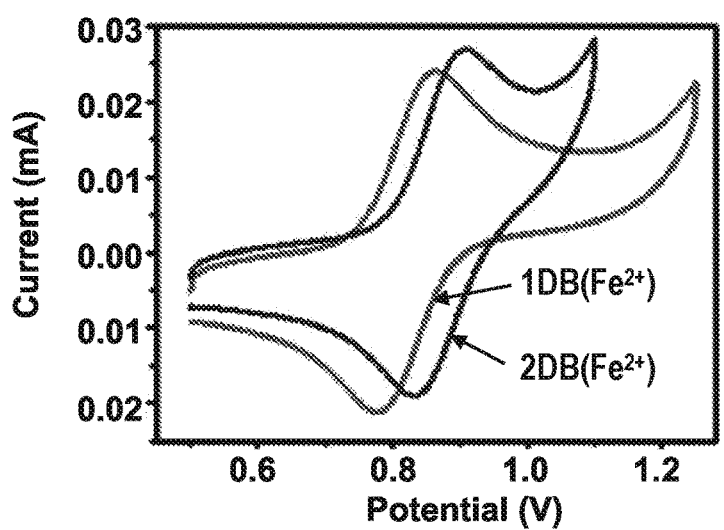
Figure 3C:
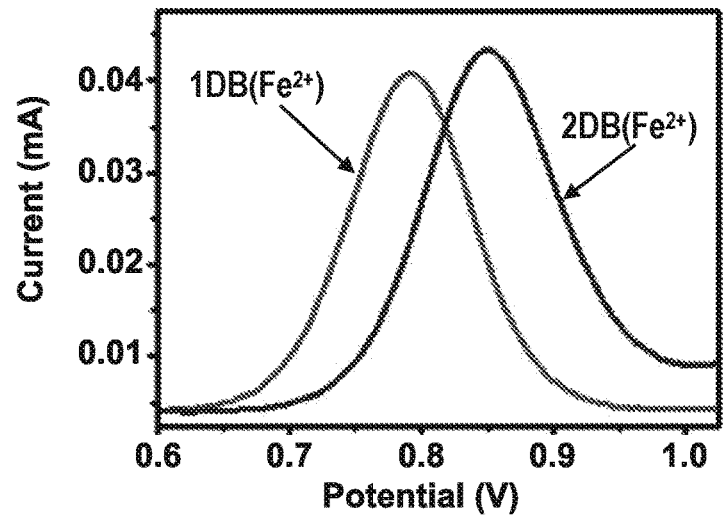
Figure 4A:
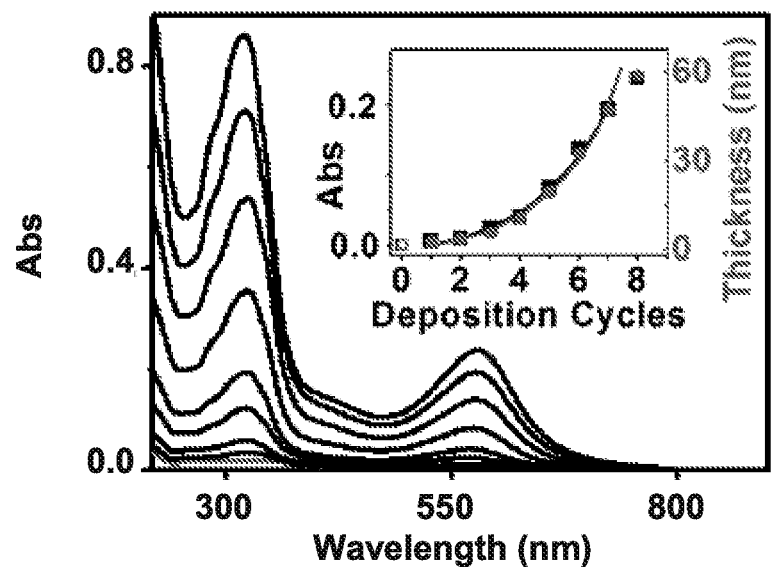
FIGS. 4A-4D show representative transmission optical absorbance spectra of (4A) MA1DB and (4B) MA2DB after each (1DB(Fe$^{2+}$), 2DB(Fe$^{2+}$)) deposition cycle. Insets: Intensities of absorption bands at 575 nm (MA1DB) and 591 nm (MA2DB) (left axis, black) and the ellipsometry derived thickness (right axis, red) vs. the number of deposition cycles. (4C) Total ejected charge as a function of the number of deposition cycles (MA1DB and MA2DB). Inset: Corresponding CVs of MA1DB and MA2DB. (4D) Raman intensity (1610 cm$^{-1}$) as a function of the number of deposition cycles. Inset: Raman spectra of MA1DB and MA2DB (8 deposition cycles). Each deposition cycle consists of a reaction with PdCl$_2$ and complex 1DB(Fe$^{2+}$) or 2DB(Fe$^{2+}$). Deposition cycle 0 corresponds to the template layer. ($R^2$>0.93 all fits).
Figure 4B:
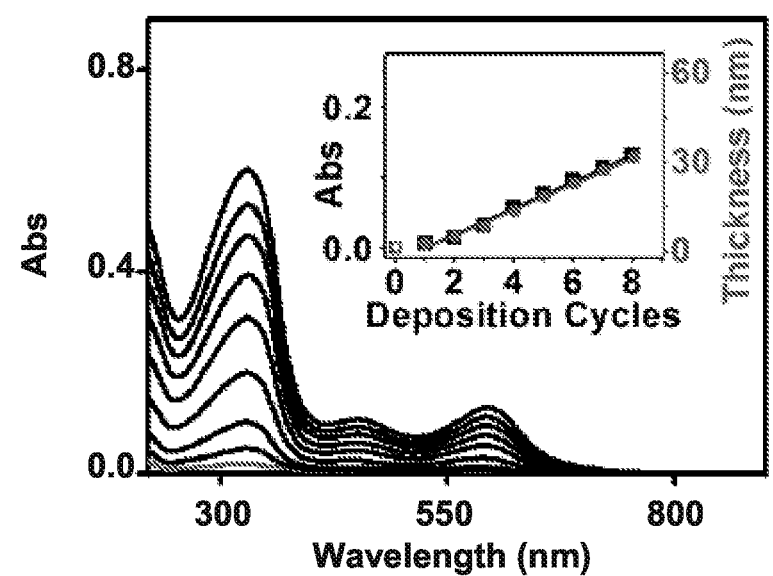
Figure 4C:
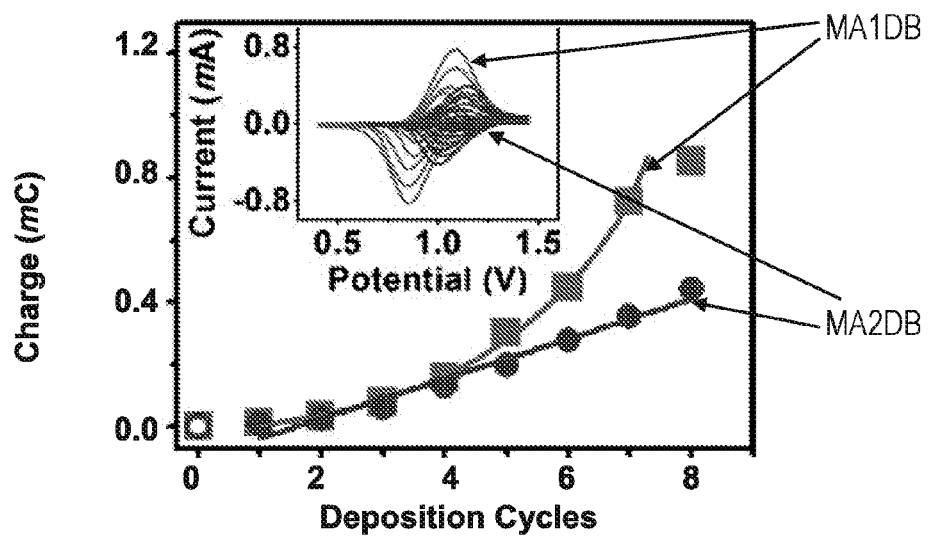
Figure 4D:
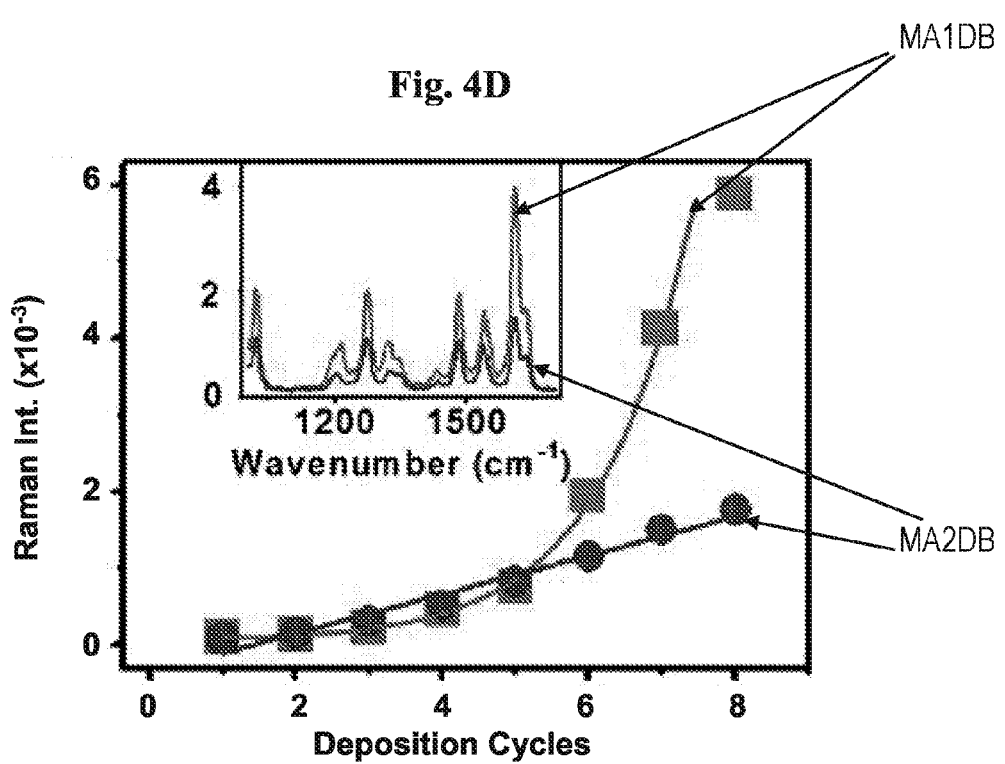
Figure 5A:
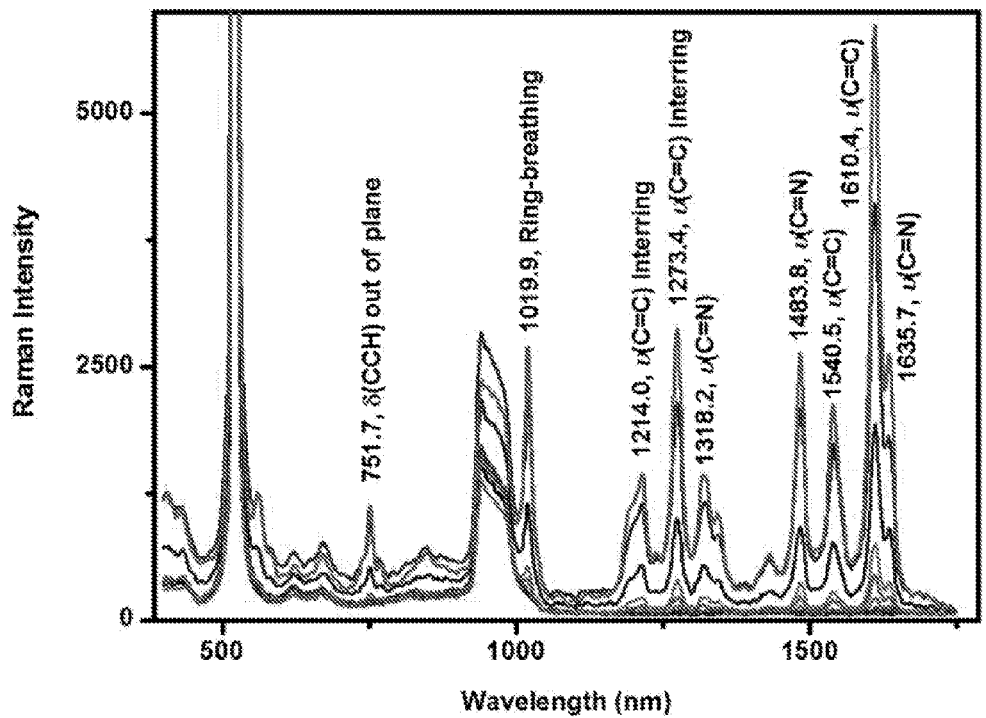
FIGS. 5A-5B show representative Raman spectra of (5A) MA1DB and (5B) MA2DB showing the corresponding increase in the intensities of peaks with increasing number of deposition cycles.
Figure 5B:
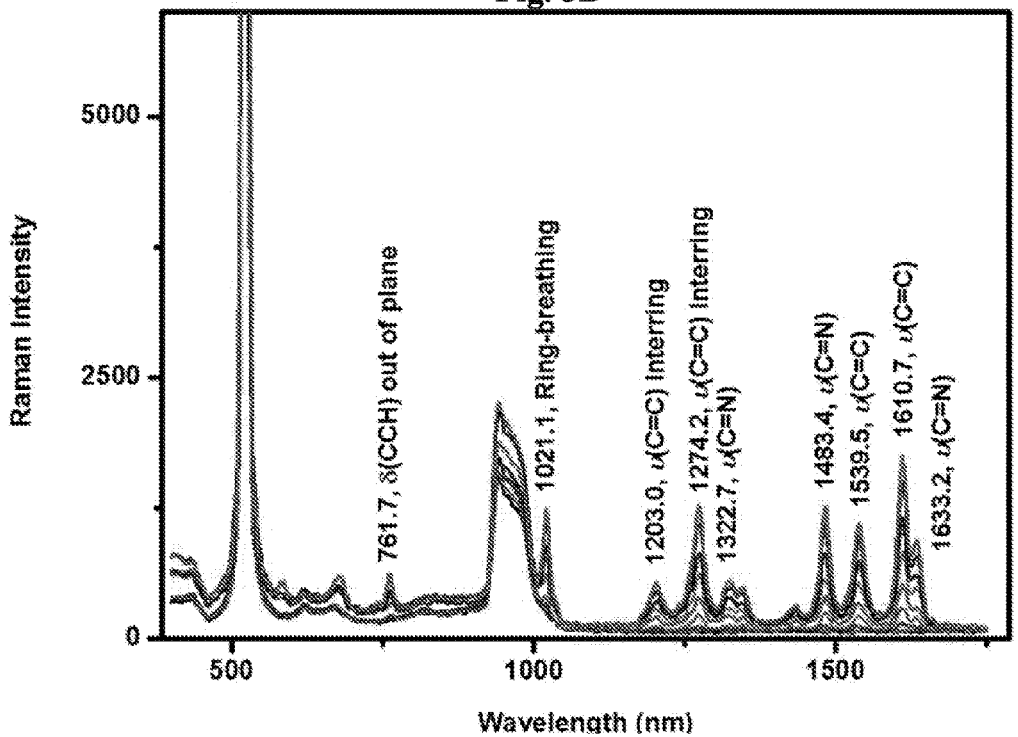
Figure 6A:
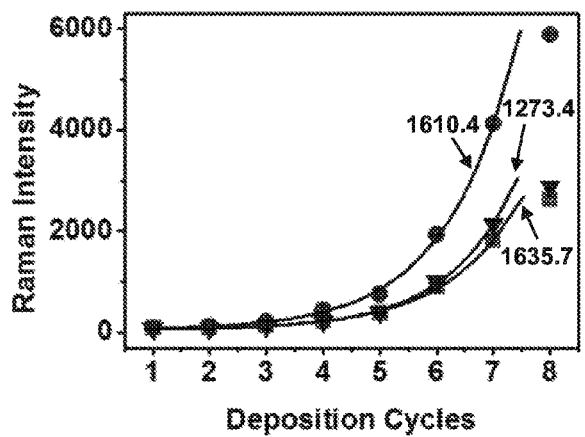
FIGS. 6A-6B show Raman intensity as a function of the number of deposition cycles: (6A) peaks at 1635.7 cm$^{-1}$, 1610.4 cm$^{-1}$, and 1273.4 cm$^{-1}$ for MA1DB; and (6B) 1633.2 cm$^{-1}$, 1610.7 cm$^{-1}$ and 1274.2 cm$^{-1}$ for MA2DB ($R^2>0.94$ for all fits).
Figure 6B:
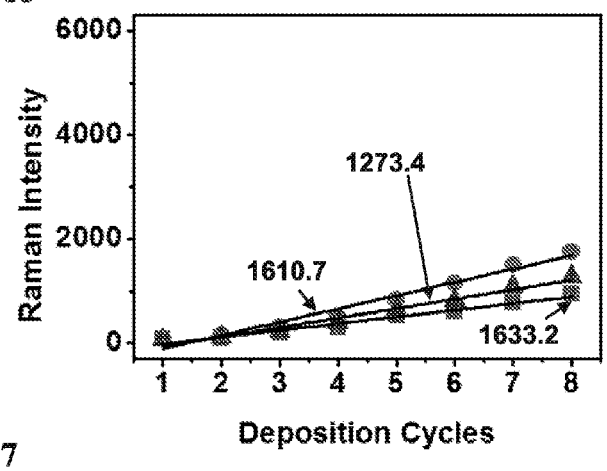

The characteristic MLCT band of MA1DB and MA2DB at λ=574 nm and 591 nm, respectively (see FIG. 3 for solution UV/vis spectra), were followed by transmission mode UV/vis spectroscopic measurements and a plot of the respective absorption maxima vs. deposition cycles revealed an exponential trend in the growth of MA1DB (FIG. 4A) and a linear trend in that of MA2DB (FIG. 4B). A similar growth pattern consistent with the UV/vis measurements was observed for both MA1DB and MA2DB when thickness of the assemblies was plotted against increasing deposition cycles (FIGS. 4A-4B, insets). Thus, the growth and hence the properties of the MAs are significantly affected by the coordination geometry and molecular structure of the ligands on the metal center as evidenced by the steep exponential growth of MA1DB and linear growth of MA2DB, under identical deposition conditions. It could well be emphasized that the linear growth of MA2DB resulted in a film approximately half as thick as the exponentially grown MA1DB after 8 deposition cycles and the thickness of the films obtained by ellipsometry and XRR measurements were found to be in good correlation. Raman intensity (1610 cm$^{-1}$) as a function of the number of deposition cycles also exemplifies the exponential-linear growth behavior of MA1DB and MA2DB respectively (FIGS. 4D, 5 and 6).

Figure 7:
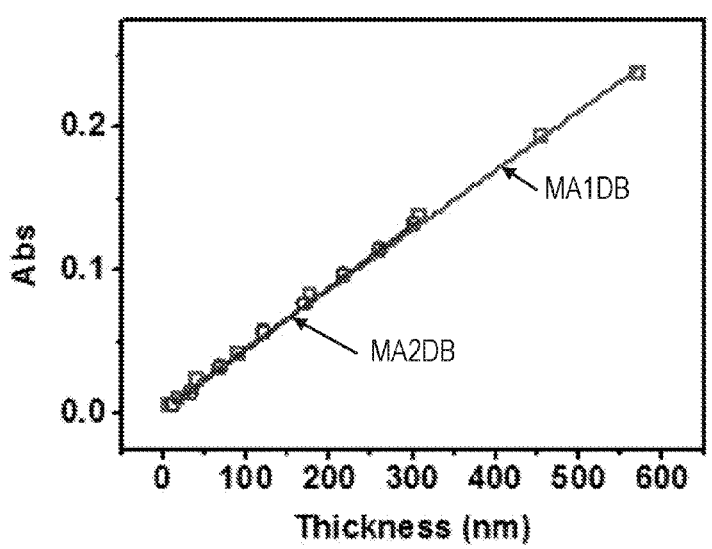
FIG. 7 shows linear correlation ($R^2>0.99$) between the ellipsometer derived thickness (nm) and MLCT $\lambda_{max}$ (abs) of MA1DB (575 nm) and MA2DB (591 nm) over 1-8 deposition cycles.

A linear correlation between the film thickness and absorption intensities (R$^2$>0.99) confirms the formation of thin films with uniform composition irrespective of the substrate used (FIG. 7). The AFM measurements indicated relatively smooth surfaces with roughness values less than 1 nm for MA1DB (thickness>57 nm) and less than 0.5 nm for MA2DB (thickness>30 nm), after 8 deposition cycles (Table 1). Even though the surface roughness was found to increase with increasing thickness for both the assemblies, no reasonable correlation was found to justify the exponential growth of MA1DB and linear growth of MA2DB.

TABLE 1

Root mean square roughness of the MAs measured using AFM

| Deposition cycle | Roughness (nm) | |
|---|---|---|
| | MA1DB | MA2DB |
| 2 | 0.4 | 0.4 |
| 4 | 0.6 | 0.4 |
| 6 | 0.7 | 0.4 |
| 8 | 0.9 | 0.5 |

The observed trends in growth of the assemblies are consistent with those reported in Moieti et al. (2008) on the exponential growth of the SPMAs, resulting from the porous nature of the assemblies capable of trapping excess Pd salt, which could later be used for subsequent coordination with more metal complex, via migration to the solid-solution interface. For a fully formed network, in which Pd bridges all the pyridines of one metal complex to another, the expected Pd/Fe ratio is 1.5 for MA1DB and 3 for MA2DB, and a reasonably higher ratio could be ascribed to a faster, non-linear growth of the assemblies using the trapped excess Pd via a diffusion controlled mechanism as described above. XPS analysis of our assemblies confirmed the Pd/Fe ratio in MA1DB was ~2.6 (>73% excess Pd) and that in MA2DB was 3.6-3.7 (~20% excess Pd) after 3-5 deposition cycles, which justifies the faster growth of the former compared to the slower growth of latter. This effect could presumably be due to the structural features of the complexes 1DB($Fe^{2+}$) and 2DB($Fe^{2+}$)—and clearly, sterically more demanding 2DB($Fe^{2+}$) allows a little excess of Pd to be trapped, moreover, its migration back to the surface would also be hindered.

Figure 8:
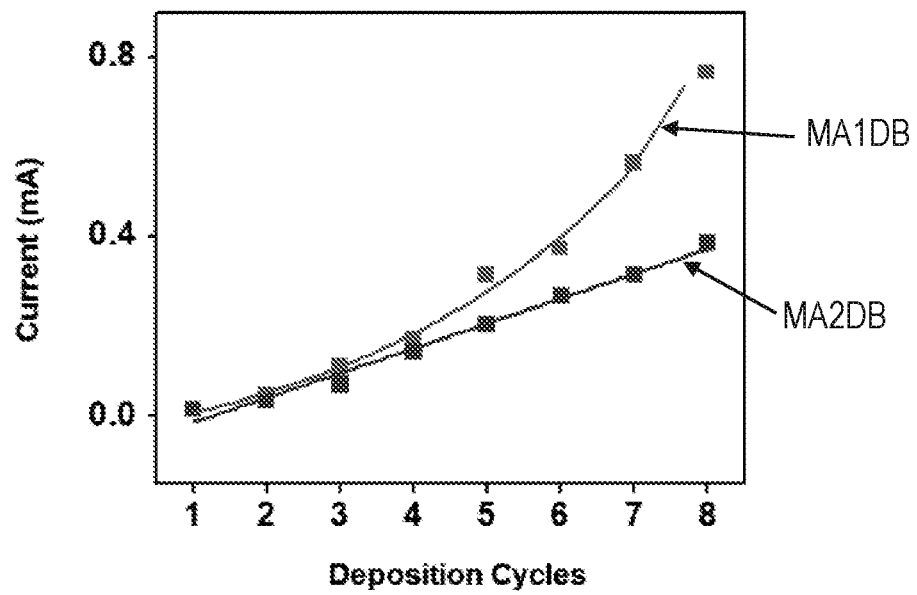
FIG. 8 shows comparison of the peak current of MA1DB and MA2DB as a function of deposition cycles. $R^2>0.98$ for all fits.
Figure 9:
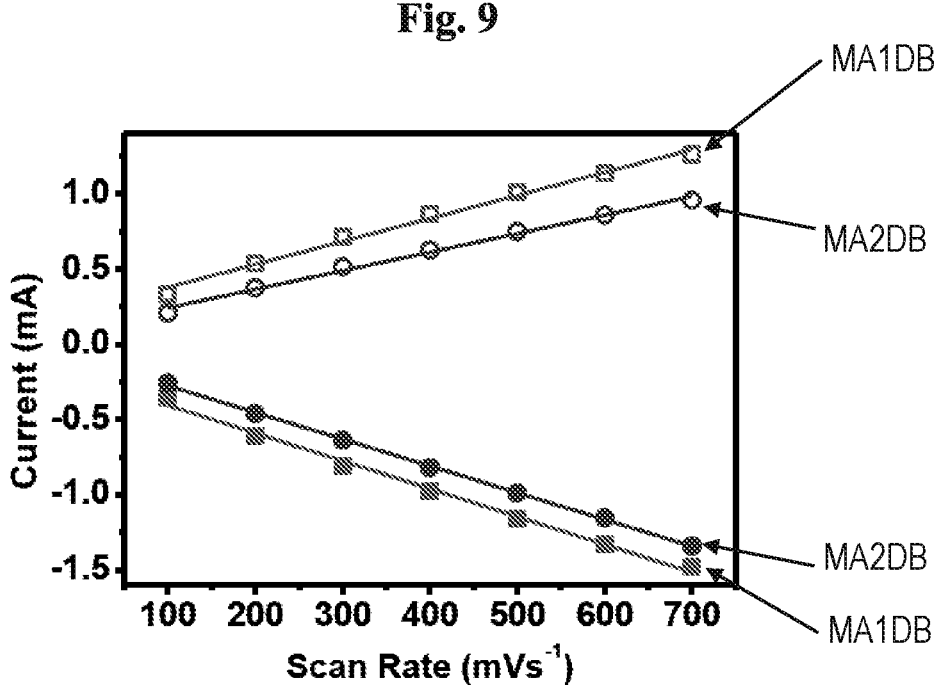
FIG. 9 shows linear correlation between scan rate (mVs$^{-1}$) and peak current (mA) of MA1DB and MA2DB (5 deposition cycles) during oxidative (unfilled) and reductive (solid) directions. $R^2 \geq 0.99$ for all fits.

As previously reported, multicomponent assemblies constructed from pyridine based complexes of ruthenium and osmium, and $PdCl_2$ are redox active (Motiei et al., 2008; de Ruiter et al., 2013a; de Ruiter et al., 2013b). Reversible redox processes characteristic of $Fe^{2+/3+}$ couple was revealed by CV measurements of MA1DB and MA2DB on ITO coated glass. The half wave potentials ($E_{1/2}$, Vs $Ag/Ag^+$) of 0.958 V and 1.079 V respectively at a scan rate of 100 $mVs^{-1}$. This anodic shift of $E_{1/2}$ by 121 mV in MA2DB could obviously be attributed to the comparably higher electron delocalization in the bipyridine derived ligands due to extended conjugation. The peak current and total charge (obtained by the integration of the voltammetric peaks) increase exponentially with increasing deposition cycles for MA1DB and linearly for MA2DB (FIGS. 4C and 8). This is in full agreement with the UV/vis and thickness measurements; more significantly, provides yet another proof for the substrate-independent growth of the assemblies. The slow nature of the electron transfer process in both the assemblies is indicated by the increase in peak-to-peak separation with increasing deposition cycles as well as the scan rates. The peak current was found to be linearly proportional to scan rate (100 mV/s to 1 V/s) (FIG. 9) and increases exponentially with the square root of scan rate (FIG. 6), showing a surface-confined electrochemical oxidation-reduction process that is not just limited by slow diffusion.

Figure 10A:
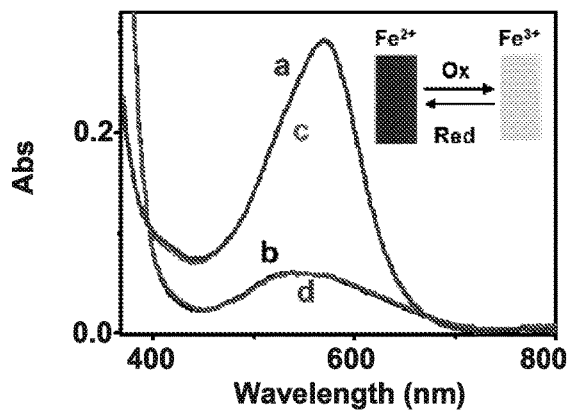
FIGS. 10A-10B show electrochromic switching of the MAs. Optical absorption spectra corresponding to consecutive oxidation and reduction of (10A) MA1DB and (10B) MA2DB. SEC was done using double-potential steps between 0.4 and 1.7 V: (a) reduced ($Fe^{2+}$), (b) oxidized ($Fe^{3+}$), (c) reduced ($Fe^{2+}$) and (d) oxidized ($Fe^{3+}$) states. Inset: photographs of MA1DB and MA2DB showing the colored ($Fe^{2+}$) and the bleached ($Fe^{3+}$) states.
Figure 10B:
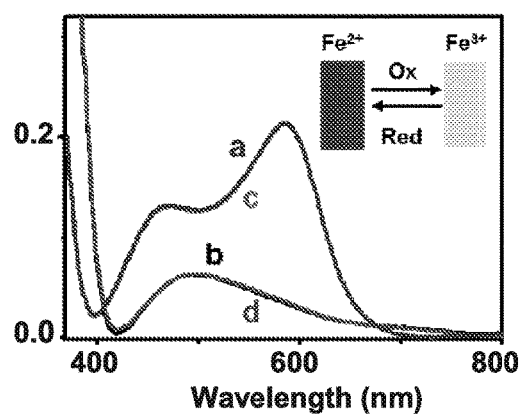

This single electron oxidation/reduction process is accompanied by a reversible change in color of the molecular assemblies assigning them with electrochromic properties. For instance, MA1DB ($Fe^{2+}$) is purple and MA2DB ($Fe^{2+}$) is grey-blue, which on oxidation ($Fe^{3+}$) turns more or less transmissive due to the bleaching of the MLCT bands (FIG. 10).

The electrochromic behavior of the assemblies was investigated by SEC using a square wave potential step method involving chronoamperometry coupled to optical spectroscopy. The optical response during the switching of potential in a stepwise manner between the oxidized (transmissive) and reduced (colored) states was recorded at the corresponding absorption maxima ($\lambda_{max}$=575 nm for MA1DB and 591 nm for MA2DB) as percentage transmittance ($\Delta\%$ T) over time, with the active area of the assemblies on the substrate fixed at 3.36 $cm^2$. The $\Delta\%$ T at a pulse width of 5 sec. was found to be larger for MA2DB compared to MA1DB for films of ~17 nm thickness (5 deposition cycles), even though the total injected charge for the same films were found to be higher for MA1DB. In fact, a superior degree of electro-optic response was evidenced for MA2DB compared to their MA1DB counterparts, suggesting an enhanced electrochromic performance and efficiency ($\Delta\%$ T $[MA1DB_8]_{\lambda_{max}=574\ nm}$ (41.3); $\Delta\%$ T $[MA2DB_8]_{\lambda_{max}=591\ nm}$ (33.8)).

Benefiting from their vibrant switching from coloured to transmissive states, these solution processable, electrochemically active molecular assemblies imply themselves as promising candidates for applications in ECDs. Nonetheless, coordination based molecular assemblies immobilised on surfaces do come with a stability concern and rational device design demands a judicious combination of both performance and robustness.

Figure 11A:
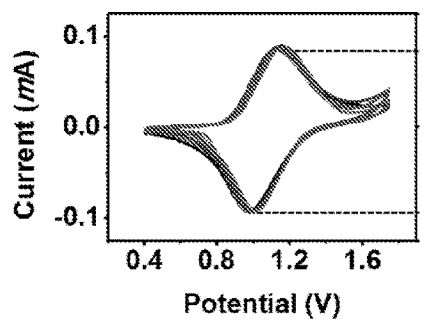
FIGS. 11A-11C show electrochemical stability of MA2DB. (11A) CV of MA2DB (23 nm, 8 deposition cycles) up to 112,000 switching cycles; (11B) maximum current as in 10A vs. the number of switching cycles; and (11C) SEC of MA2DB on ITO at 591 nm over a potential range of 0.55 to 1.45V with a 1 s pulse width, employing a 0.1 M Bu4NPF$_6$/PC electrolyte solution in a multistep square-wave potential measurement under in situ monitoring of % transmittance.
Figure 11B:
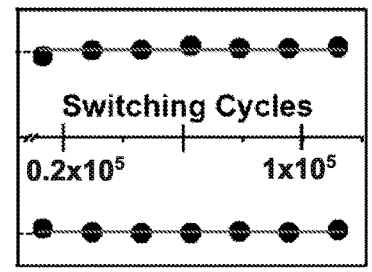
Figure 11C:
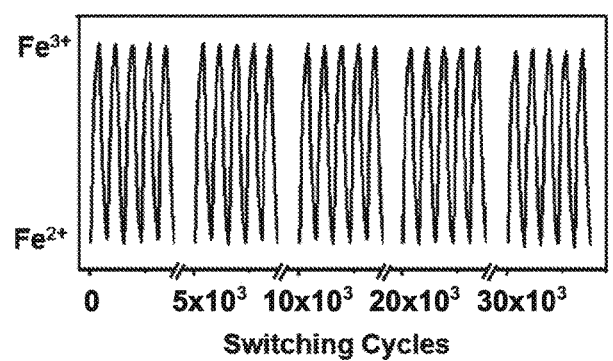
Figure 12A:
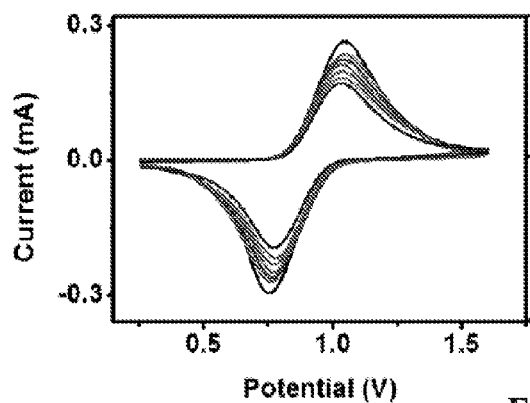
FIGS. 12A-12C show electrochemical stability of MA1. (12A) CV of MA1DB (57 nm, 8 deposition cycles) up to 30,000 switching cycles (black—start, red—after 5000 cycles, blue—after 10000 cycles, cyan—after 15000 cycles, magenta—after 20000 cycles, yellow—after 25000 cycles, navy—after 30000 cycles); (12B) maximum current as in 12A vs. the number of switching cycles; and (12C) SEC of MA1DB on ITO at 574 nm over a potential range of 0.55 to 1.55V with a 1 s pulse width, employing a 0.1 M Bu$_4$NPF$_6$/PC electrolyte solution in a multistep square-wave potential measurement under in situ monitoring of % transmittance.
Figure 12B:
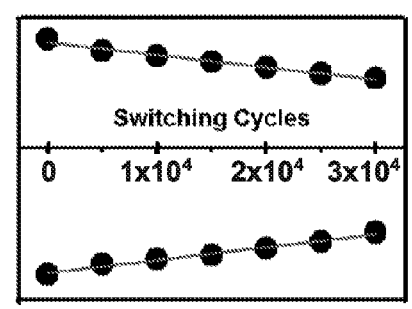
Figure 12C:
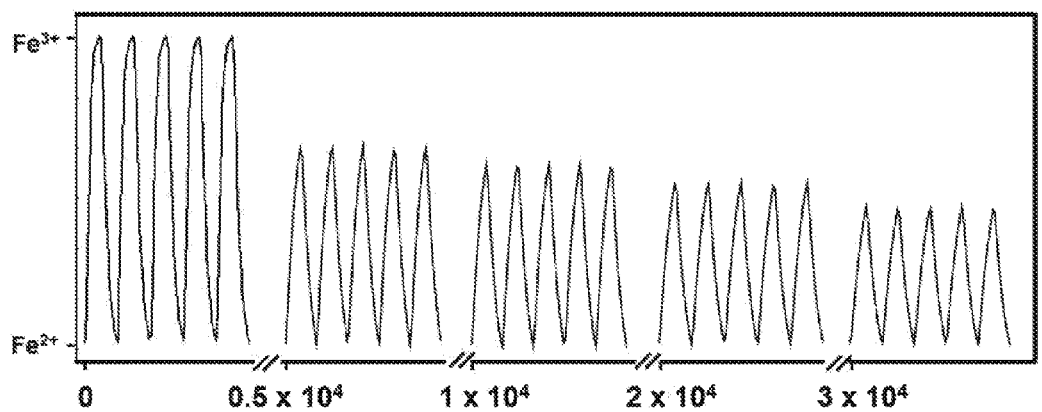

The electrochemical stability of the assemblies was followed by CV and SEC in $TBAPF_6$-propylene carbonate electrolyte solution over time. The CV of MA2DB after every few thousands of continuous spectroelectrochemical switching cycles confirmed its ultra-high stability. No detectable decrease in the maximum current (in both oxidative and reductive directions) was observed aleaset until 112,000 cycles (FIGS. 11A-B). The decrease in $\Delta\%$ T was found to be negligible (compared to maximum $\Delta\%$ T) after 30,000 redox cycles (FIG. 11C). MA1DB was found to electrochemically less stable compared to MA2DB (FIG. 12).

Figure 13:
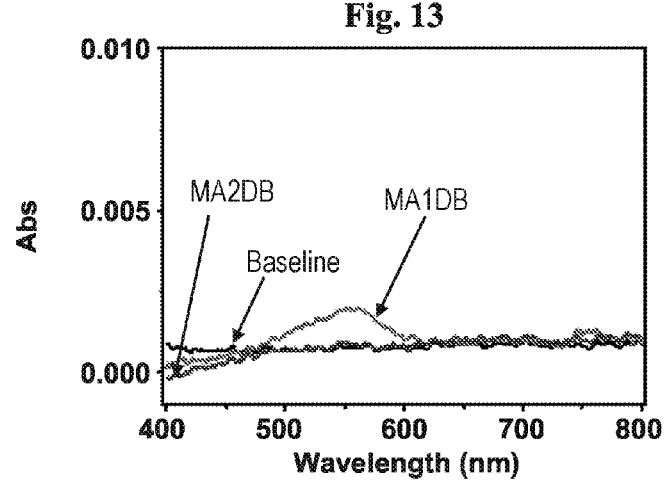
FIG. 13 shows representative UV-vis spectra of the electrolyte solution containing MA1DB and MA2DB after electrochemical switching experiments for 3 hours.

The electrochemical stability of MA2DB was also proved by repeating the same experiments (for 30,000 cycles) over 6 days with continuous exposure to UV/vis light and intentional stoppage of cycling for periods ranging from a few minutes to 10 hours, and leaving the assembly in the electrolyte solution for the whole duration. Thereafter, analysis of the electrolyte solution showed presence of traces of complex 2DB($Fe^{2+}$) with no free ligand or Fe salt in the detection limits (FIG. 13). The extra stability of MA2DB over MA1DB could be justified by (i) the larger number of binding sites; and (ii) the extended delocalization of electrons and the positive charge over a larger chain of the ligands, which in turn reduces the susceptibility of coordination based systems to dissociate, as explained by the anodic shift in the $E_{1/2}$ of MA2DB.

Figure 14A:
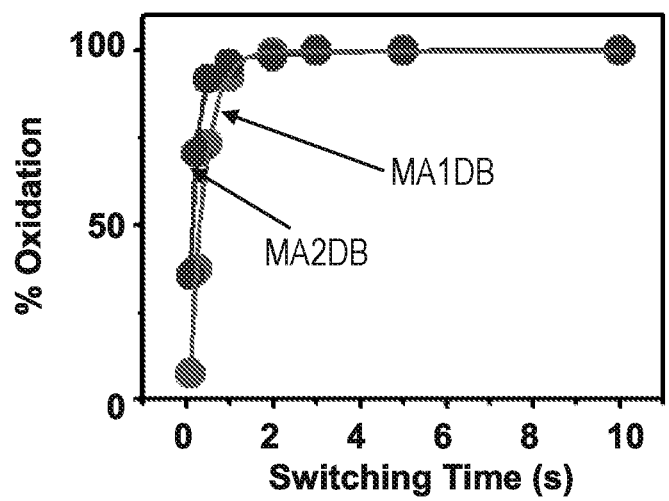
FIGS. 14A-14B show performance efficiency of MAs. (14A) Switching efficiency of MA1DB and MA2DB monitored as the variation of % oxidation vs. switching time (=pulse width) in a range of 0.1-10 s. ($R^2 \geq 0.99$). (14B) Coloration efficiency (CE) of MA1DB and MA2DB as a function of number of deposition cycles ($R^2>0.94$). Inset: variation in % transmittance (% T) with deposition cycles, in the SEC of MA1DB (574 nm) and MA2DB (591 nm) over a potential range of 0.55 to 1.45V with a 3 s pulse width, employing a 0.1 M Bu$_4$NPF$_6$/MeCN electrolyte solution in a multistep square-wave potential measurement.

MA1DB and MA2DB were confirmed to have excellent switching efficiencies as the assemblies switched at a pulse width ranging from 0.1 s to 10 s (FIG. 14A). The response time was found to be in the range of 400-500 ms for >95% switching for both the systems.

Figure 14B:
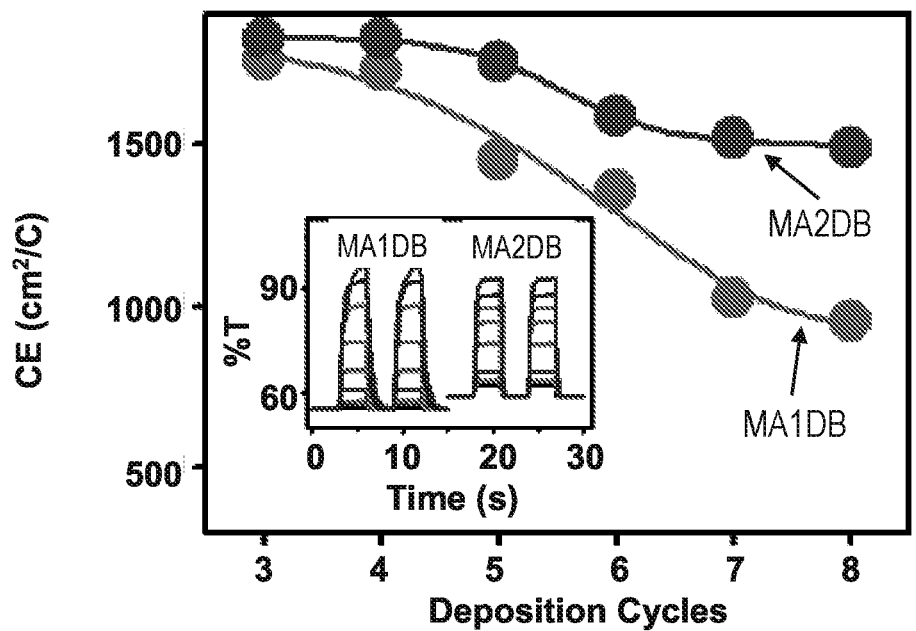

One of the key parameters determining the performance and power efficiency of any ECD is its coloration efficiency (CE), which is defined as the change in optical density ($\Delta$OD) per unit charge injected/ejected per unit area of the electrode and was calculated as described above. The CEs of the assemblies MA1DB and MA2DB after 8 deposition cycles were calculated at their MLCT $\lambda_{max}$ and were found to be 955 and 1488 $cm^2C^{-1}$, respectively (FIG. 14B). These values are exceptionally high for surface confined, coordination-based metal-organic assembles and to the best of our knowledge, no higher values of CEs have been reported for such systems, even though a slightly superlative value has been reported for PCBDT-PEDOT conjugated polymer based assemblies (CE=1728 $cm^2C^{-1}$).

Figure 15A:
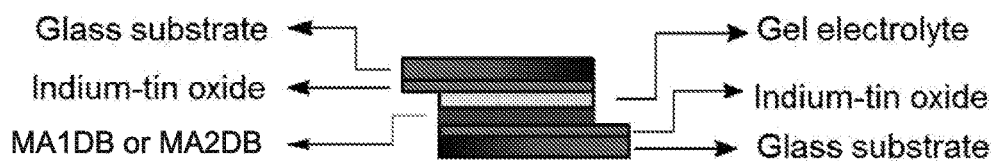
FIGS. 15A-15C show a schematic representation of the SELDs (15A); and photographs showing the SELD operation (15B-15C). A potential window of −2.7-+2.5V (MA1DB) and −3-+3V (MA2DB) was applied with a pulse width of 5 s.
Figures 15B, 15C:
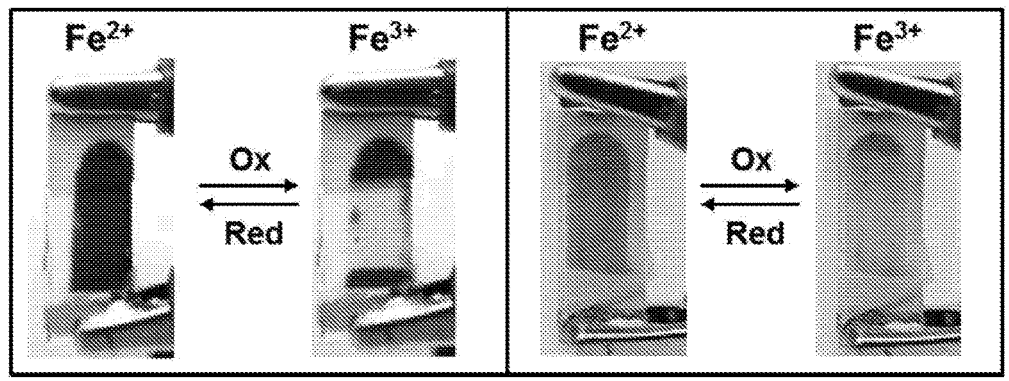
Figure 16A:
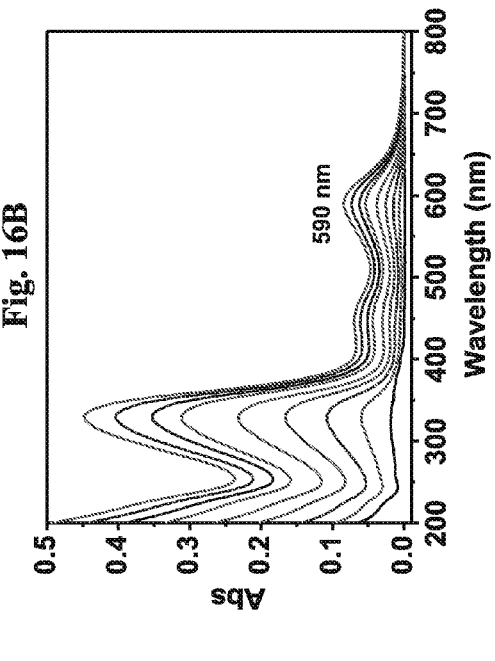
FIGS. 16A-16D show representative transmission optical absorbance spectra of MA2SB (16A), MA2DB (16B), MA2TB (16C) and MA2Mix (16D) after each deposition cycle.
Figure 16B:
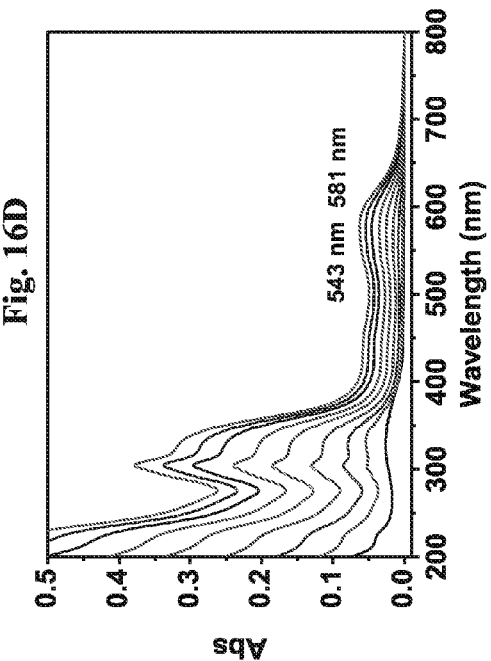
Figure 16C:
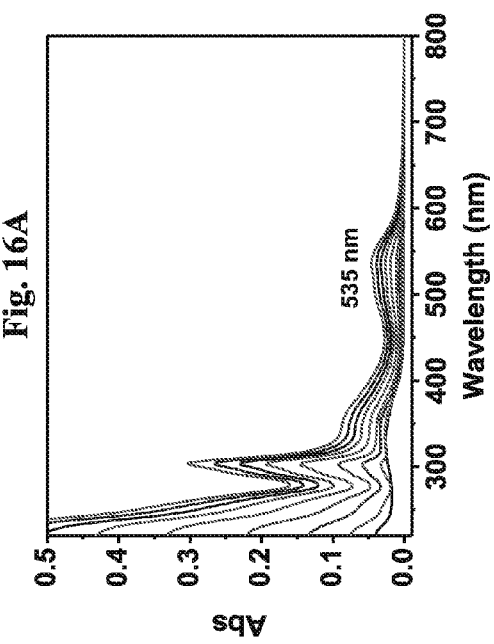
Figure 16D:
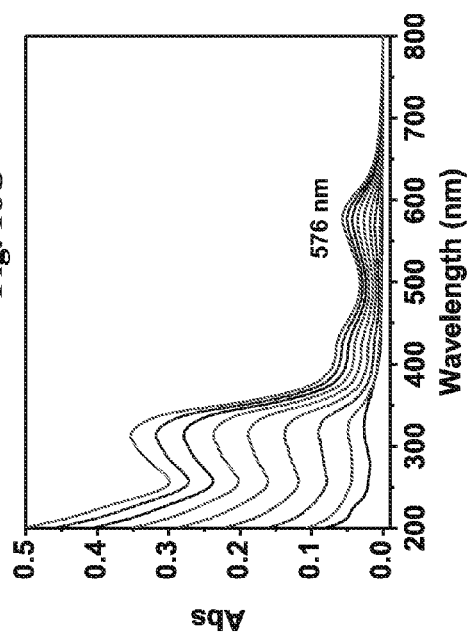
Figure 17A:
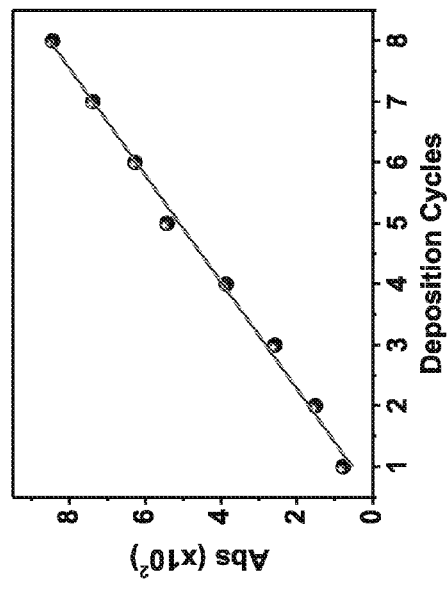
FIGS. 17A-17D show intensities of absorption bands (MLCT) at 535 nm (MA2SB, 17A, $R^2=0.99$), 590 nm (MA2DB, 17B, $R^2=0.99$), 576 nm (MA2TB, 17C, $R^2>0.99$), and 543 and 581 nm (MA2Mix, 17D, $R^2=0.99$) vs. the number of deposition cycles.
Figure 17B:
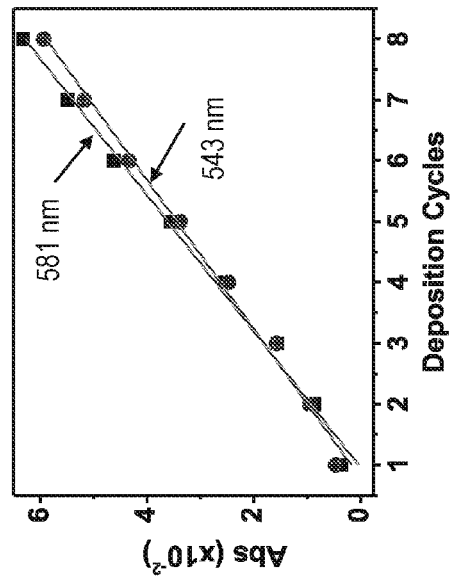
Figure 17C:
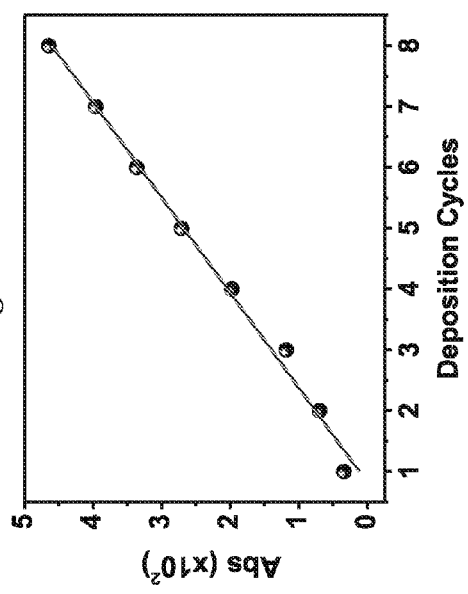
Figure 17D:
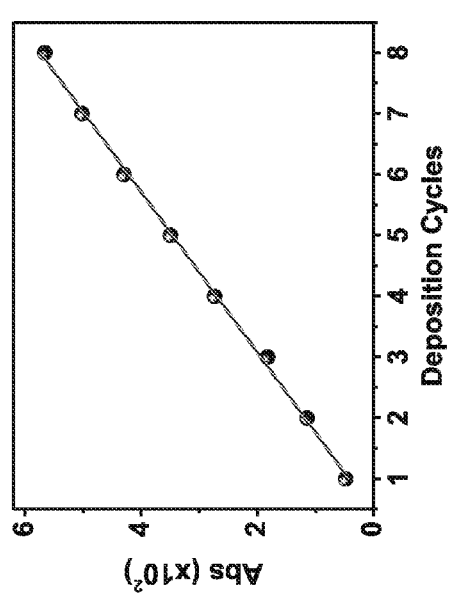
Figure 18A:
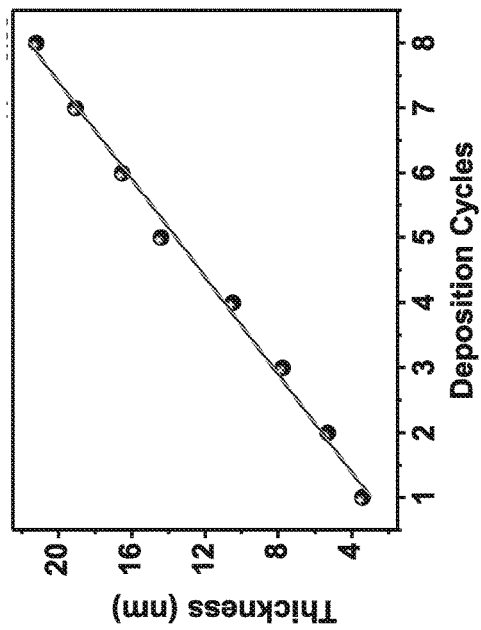
FIGS. 18A-18D show ellipsometer derived thickness of MA2SB (18A, $R^2>0.99$), MA2DB (18B, R=0.99), MA2TB (18C, $R^2>0.99$) and MA2Mix (18D, $R^2>0.99$) vs. the number of deposition cycles.
Figure 18B:
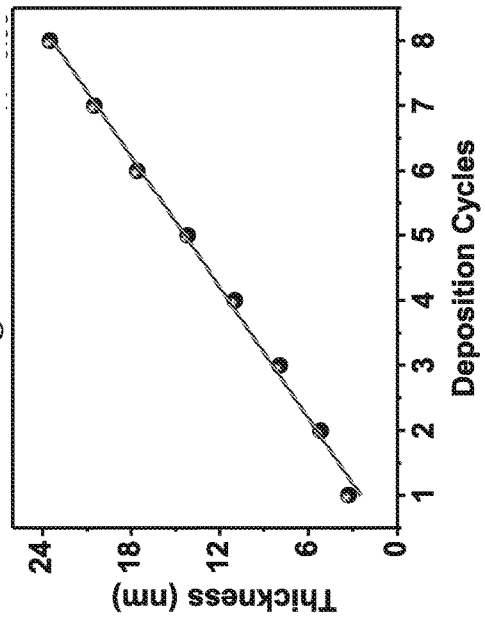
Figure 18C:
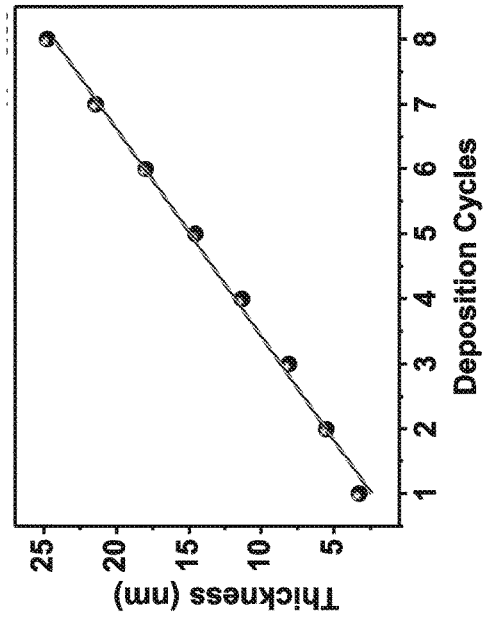
Figure 18D:
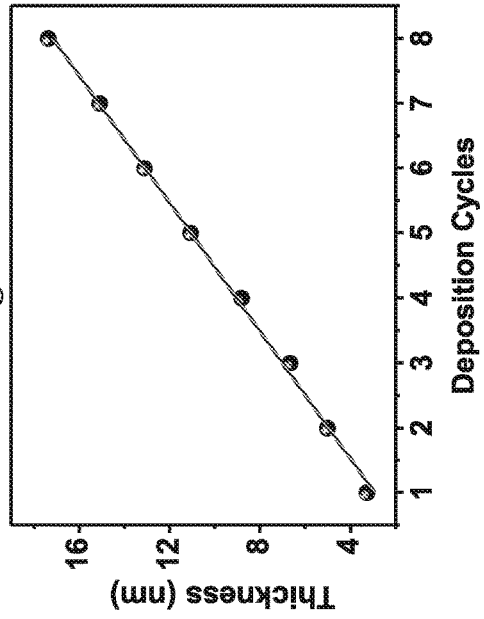
Figure 22A:
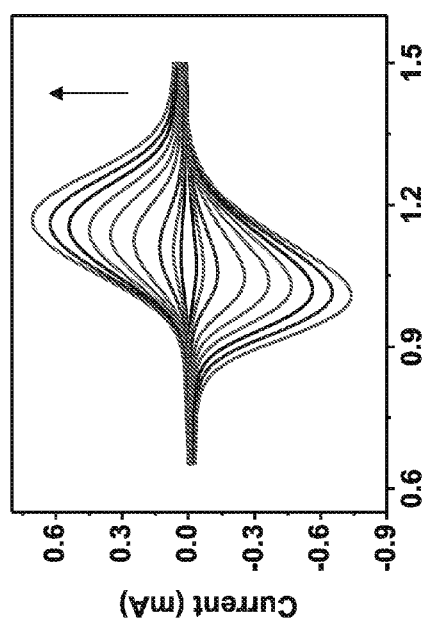
FIGS. 22A-22D show CV of MA2SB (22A), MA2DB (22B), MA2TB (22C) and MA2Mix (22D) for ~14 nm thick assemblies at scan rates of 25, 50, 100, 200, 300, 400, 500, 600 and 700 mV/s (as shown by the arrow) as immersed in a 0.1M TBAPF6 electrolyte solution using the modified ITO as working electrode, Pt wire as counter electrode and Ag/Ag$^+$ reference electrode.
Figure 22B:
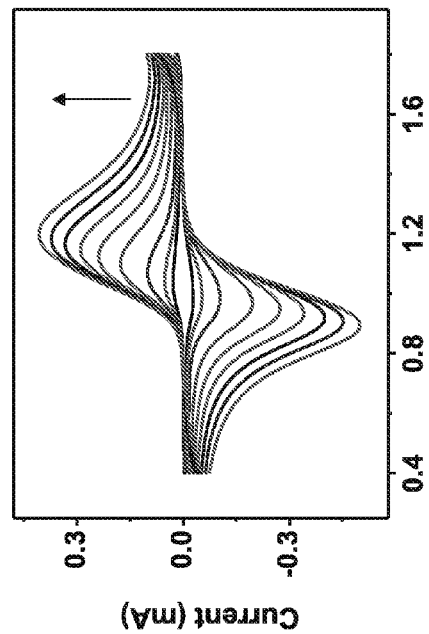
Figure 22C:
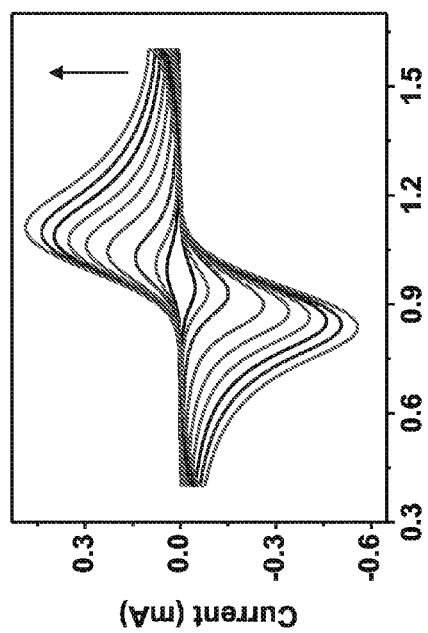
Figure 22D:
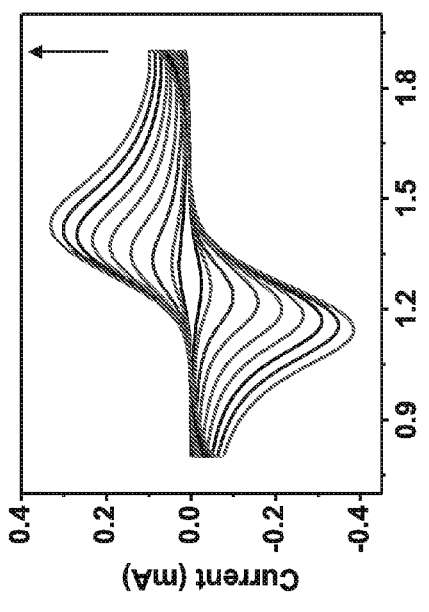
Figure 25A:
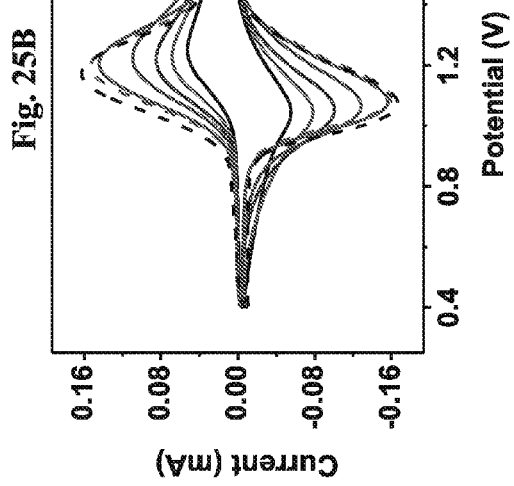
FIGS. 25A-25D show CV of MA2SB (25A), MA2DB (25B), MA2TB (25C) and MA2Mix (25D) after 8 deposition cycles at different temperature (at 100 mV/s as immersed in a 0.1M TBAPF6 electrolyte solution using the modified ITO as working electrode, Pt wire as counter electrode and Ag/Ag$^+$ reference electrode).
Figure 25B:
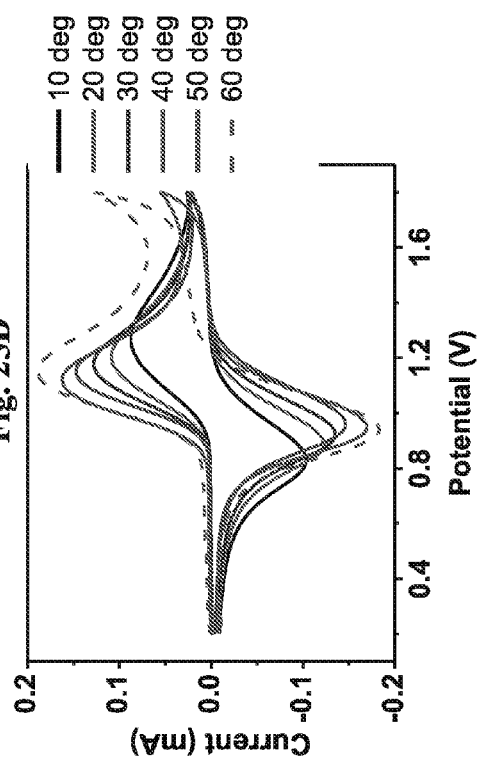
Figure 25C:
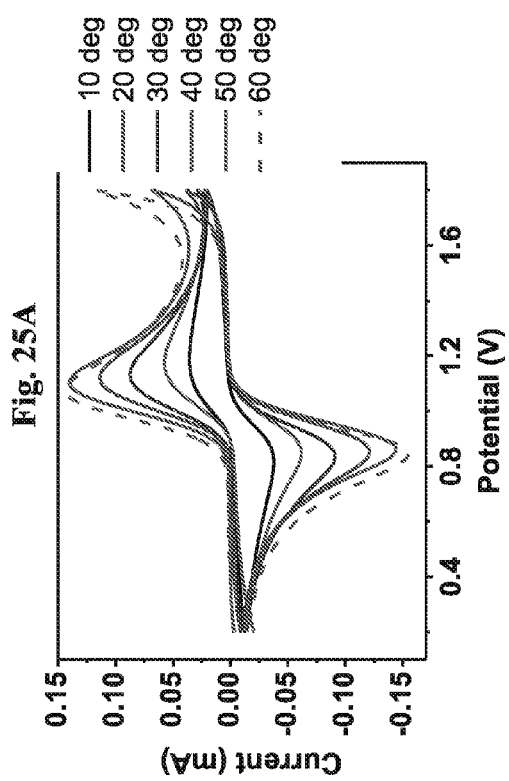
Figure 25D:
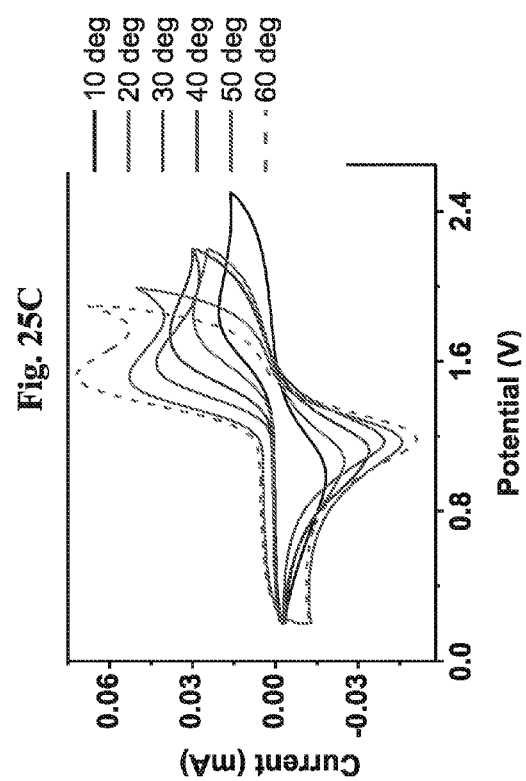
Figure 26A:
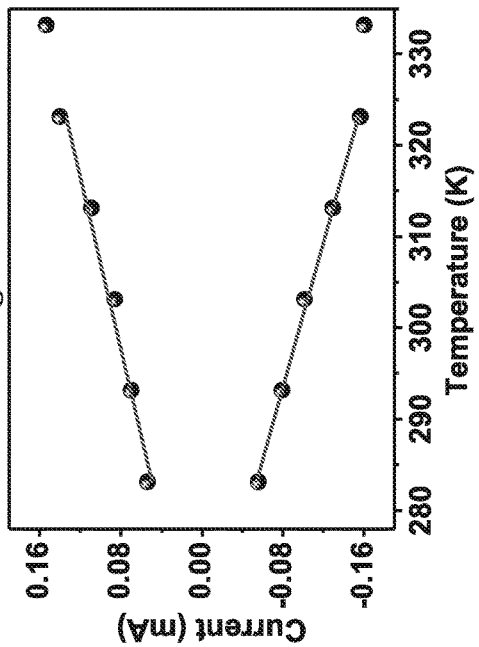
FIGS. 26A-26D show peak current (mA) derived from CV of MA2SB (26A, $R^2>0.99$), MA2DB (26B, $R^2=0.97$, 0.99), MA2TB (26C, $R^2>0.99$) and MA2Mix (26D, $R^2=0.99$) after 8 deposition cycles vs. temperature (at 100 mV/s as immersed in a 0.1M TBAPF6 electrolyte solution using the modified ITO as working electrode, Pt wire as counter electrode and Ag/Ag$^+$ reference electrode).
Figure 26B:
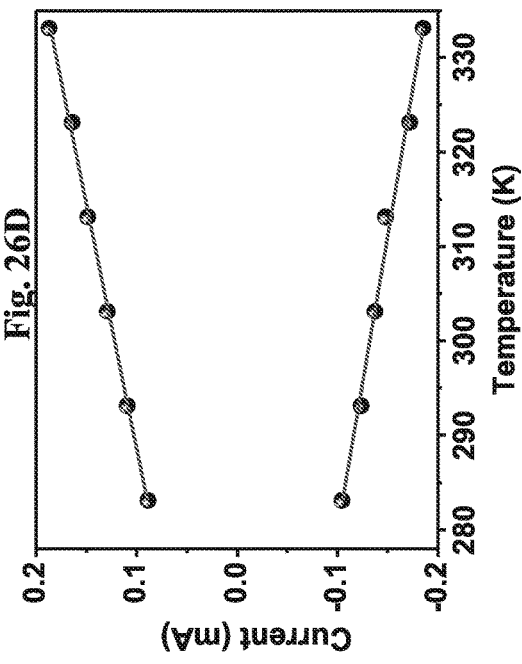
Figure 26C:
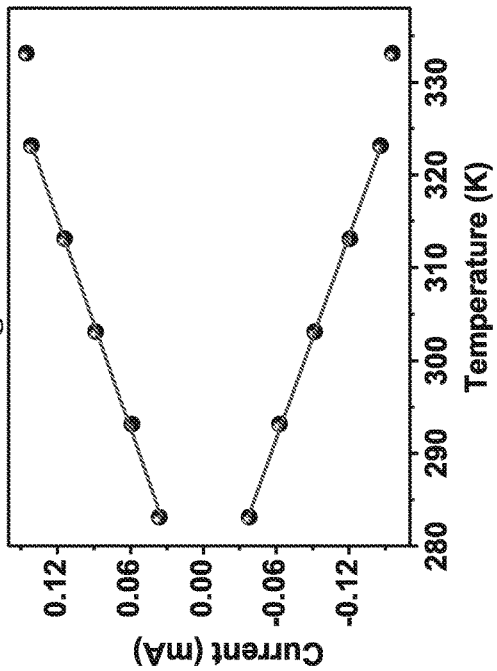
Figure 26D:
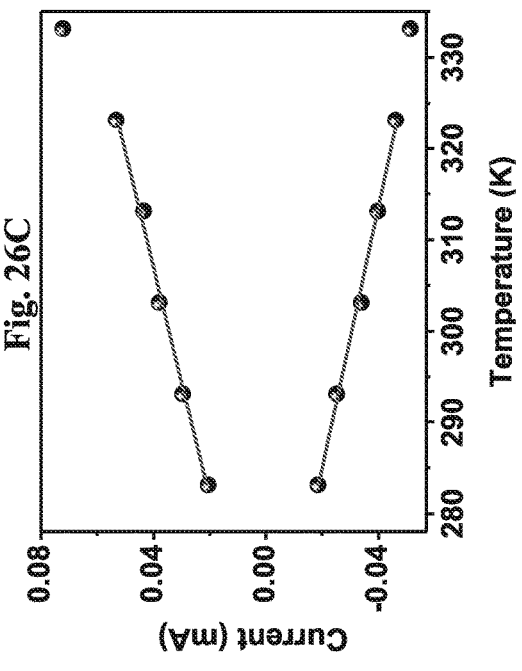

Electrochromic devices in solid state has attracted tremendous attention due to their intended applications and long term stability and we fabricated one of the first SELD of its kind using our molecular assemblies (FIG. 15). Electrochromic switching between the colored and transmissive states was observed for both the assemblies immobilized on ITO coated glass substrates, employing a gel electrolyte system (MeCN:PC:PMMA:$(CF_3SO_2)_2N^-Li^+$ 70:20:7:3 wt % composition) sandwiched between the ITO functionalized with MA1DB or MA2DB and a clean bare ITO substrate over a longer potential window (−2.7-+2.5V for MA1DB and −3-+3V for MA2DB).

In a further experiment the versatility of the SELD set-up was illustrated using the electrolyte systems (a) MeCN:PC: PMMA:$(CF_3SO_2)_2N^-Li^+$ 70:20:7:3 wt % composition; (b) MeCN:PC:PMMA:$Bu_4N^+PF_6^-$ 70:20:7:3 wt % composition; and (c) MeCN:PC:PMMA:$Bu_4N^+BPh_4^-$ 70:20:7:3 wt % composition. The switching was found to be efficient in the different electrolytes, wherein the $Bu_4N^+PF_6^-$ system being the most promising.

Study 2. Modulation of Electrochemical and Electro-Optical Signatures of MA2SB, MA2DB, MA2TB and MA2Mix In this study, pyridine terminated template layers were generated from silane based coupling layers covalently attached to silicon, quartz and glass substrates via a slight modification of the procedure previously reported (Motiei et al., 2008). Subsequently, four different multi-component MAs, herein identified MA2SB, MA2DB, MA2TB and MA2Mix, were constructed as described in Study 1, via iterative immersion of these functionalized substrates in a solution of the iron polypyridyl complex 2SB($Fe^{2+}$) (for the construction of MA2SB); 2DB($Fe^{2+}$) (for the construction of MA2DB); 2TB($Fe^{2+}$) (for the construction of MA2TB); or an equimolar mixture of 2SB($Fe^{2+}$), 2DB($Fe^{2+}$) and 2TB ($Fe^{2+}$) (for the construction of MA2Mix). Using different ligands that coordinate to the Fe centers, the electro-optical properties of the assemblies were controlled.

Figure 30B:
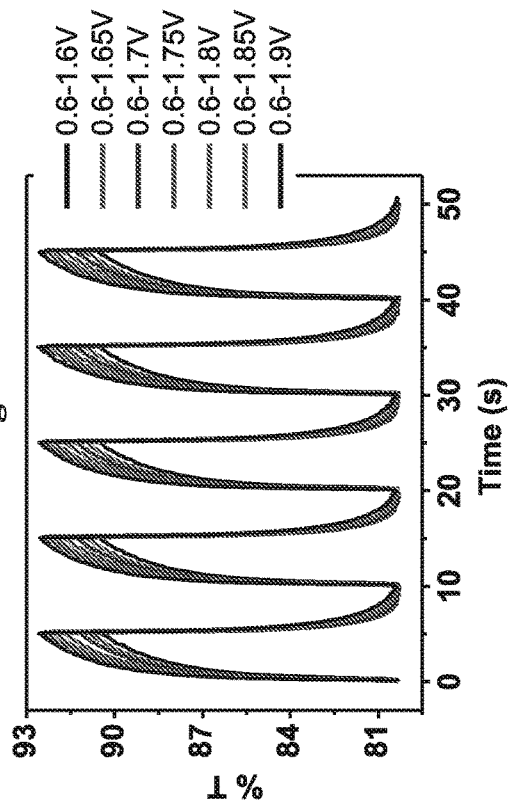
FIGS. 30A-30C show the effect of overpotential on the SEC of MA2SB (30A, 20° C.), MA2DB (30B, 10° C.) and MA2TB (30C, 20° C.) (8 deposition cycles) at low temperature (at a pulse width of 5 s. as immersed in a 0.1M TBAPF6 electrolyte solution using the modified ITO as working electrode, Pt wire as counter electrode and Ag/Ag$^+$ reference electrode). There was no detectable effect of overpotential on MA2SB and MA2TB assemblies at 10° C. and the signal to noise ratio was poor.
Figure 30A:
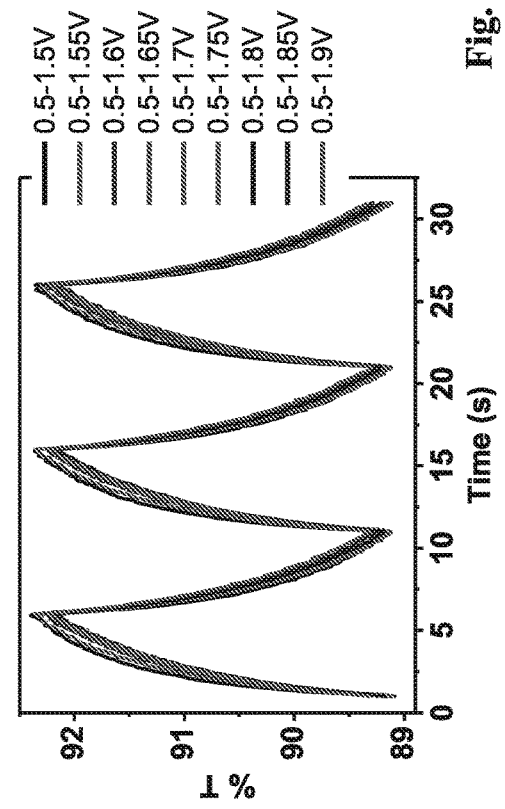
Figure 30C:
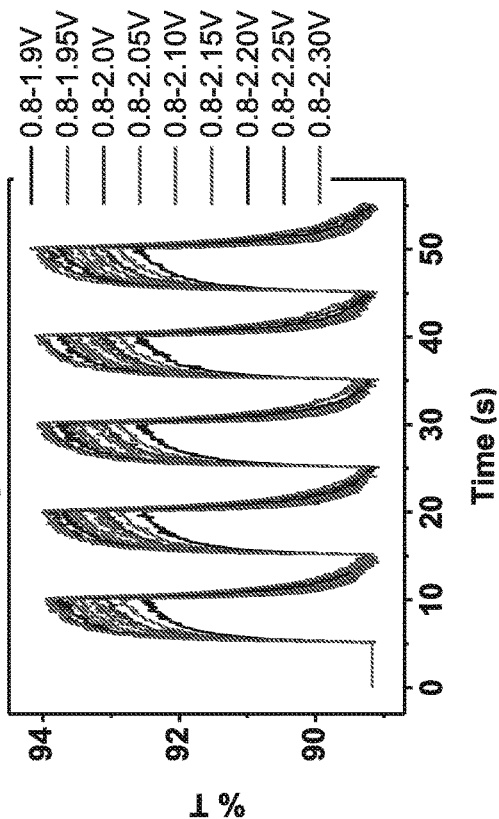
Figure 32A:
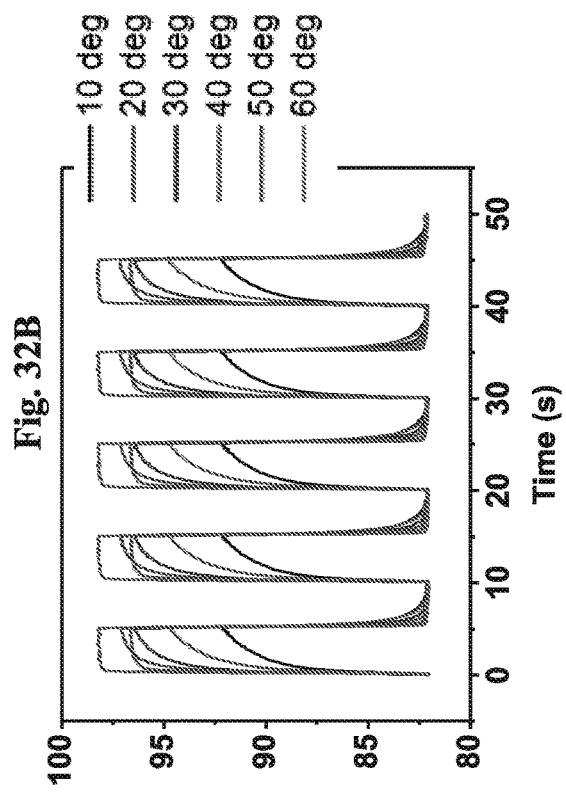
FIGS. 32A-32C show the effect of temperature on the SEC of MA2SB (32A), MA2DB (32B) and MA2TB (32C) (8 deposition cycles at a pulse width of 5 s. as immersed in a 0.1M TBAPF6 electrolyte solution using the modified ITO as working electrode, Pt wire as counter electrode and Ag/Ag$^+$ reference electrode).
Figure 32B:
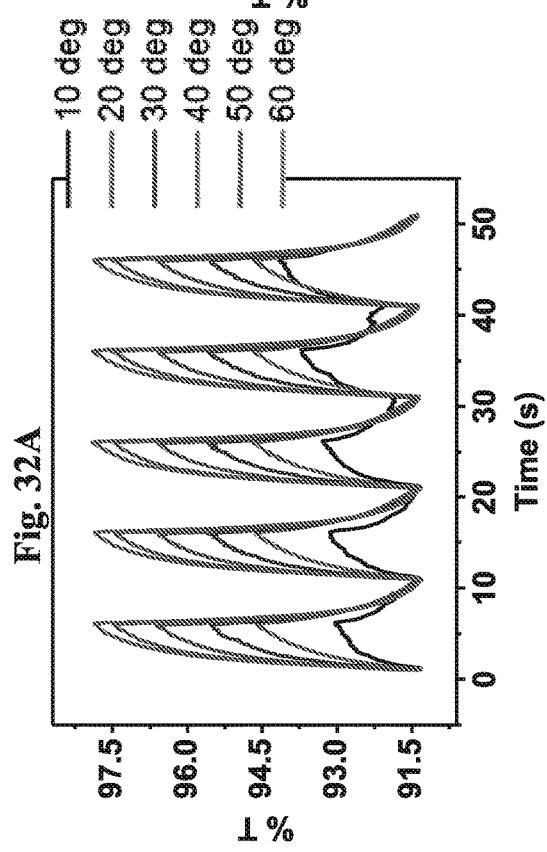
Figure 32C:
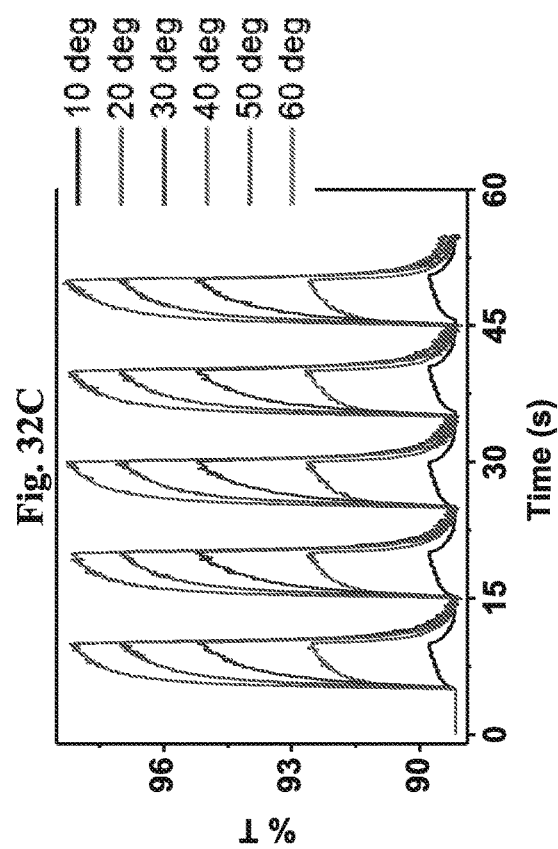
Figure 33B:
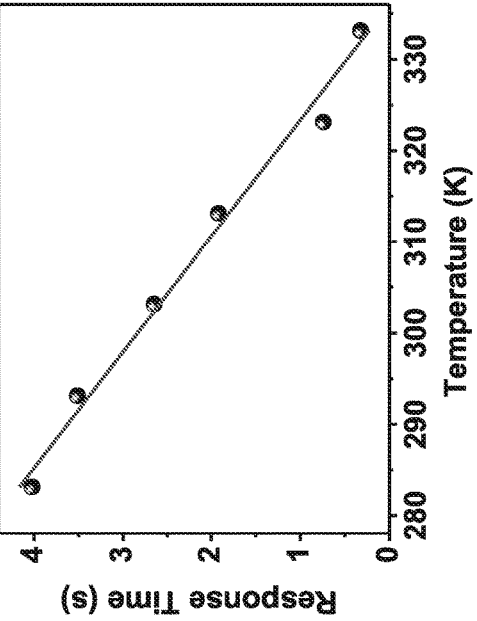
FIGS. 33A-33C show the effect of temperature on the response time of MA2SB (33A, $R^2>0.99$), MA2DB (33B, $R^2=0.98$) and MA2TB (31C, $R^2>0.99$) (8 deposition cycles, at a pulse width of 5 s. as immersed in a 0.1M TBAPF6 electrolyte solution using the modified ITO as working electrode, Pt wire as counter electrode and Ag/Ag$^+$ reference electrode).
Figure 33A:
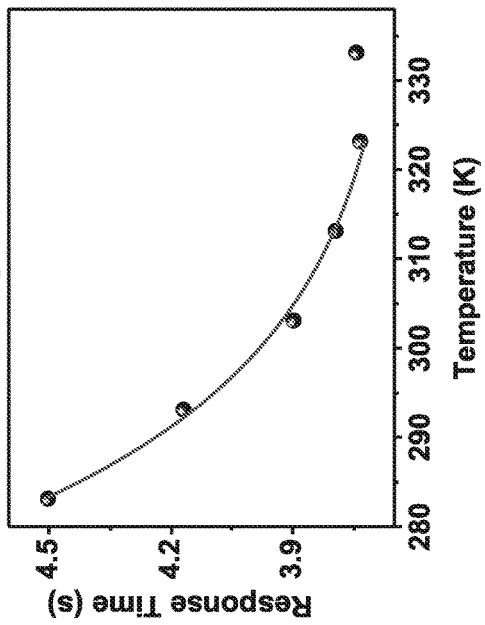
Figure 33C:
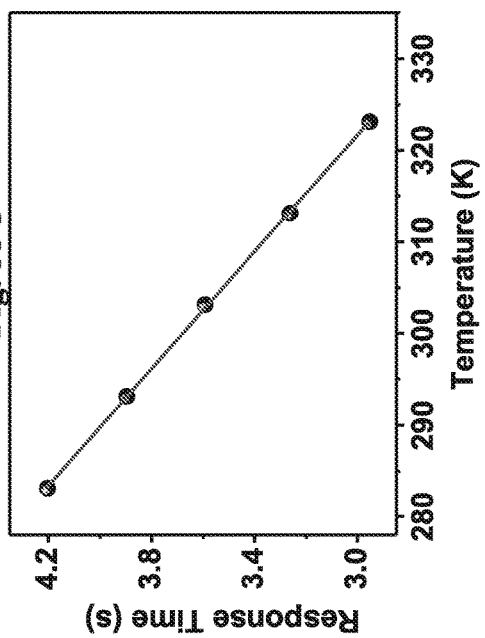
Figure 34A:
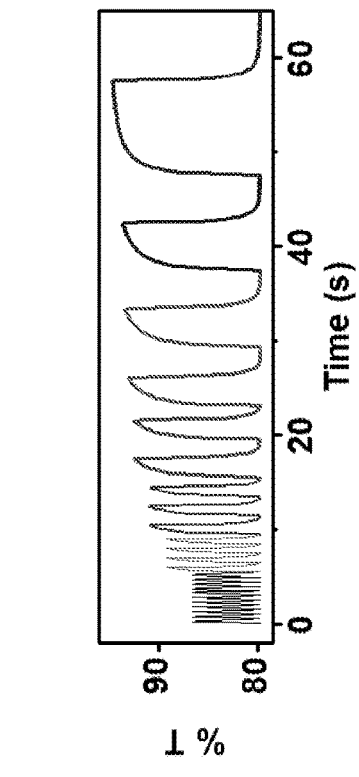
FIGS. 34A-34C show the effect of switching time (pulse width) on the SEC of MA2SB (34A, RT), MA2DB (34B, RT) and MA2TB (34C, RT) (8 deposition cycles, as immersed in a 0.1M TBAPF6 electrolyte solution using the modified ITO as working electrode, Pt wire as counter electrode and Ag/Ag$^+$ reference electrode).
Figure 34B:
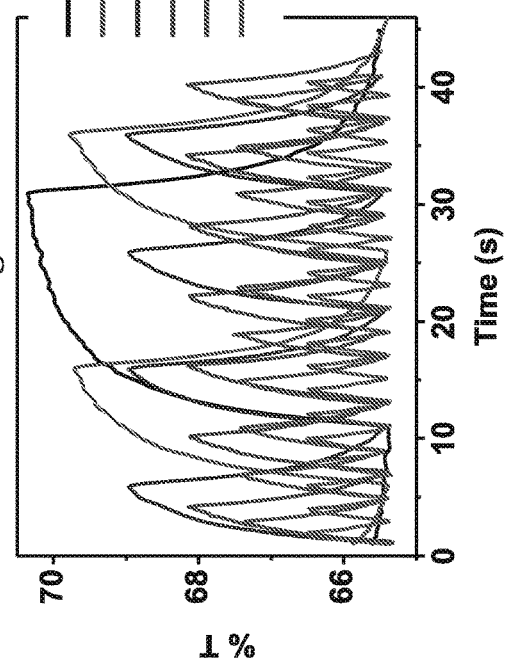
Figure 34C:
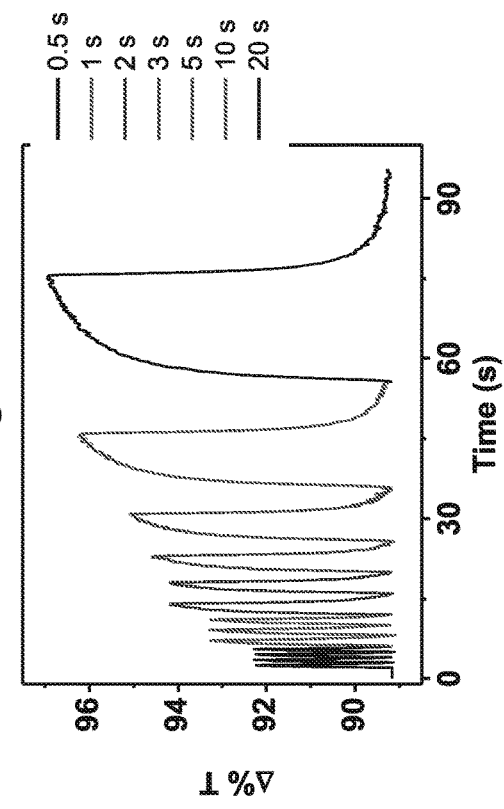
Figure 36A:
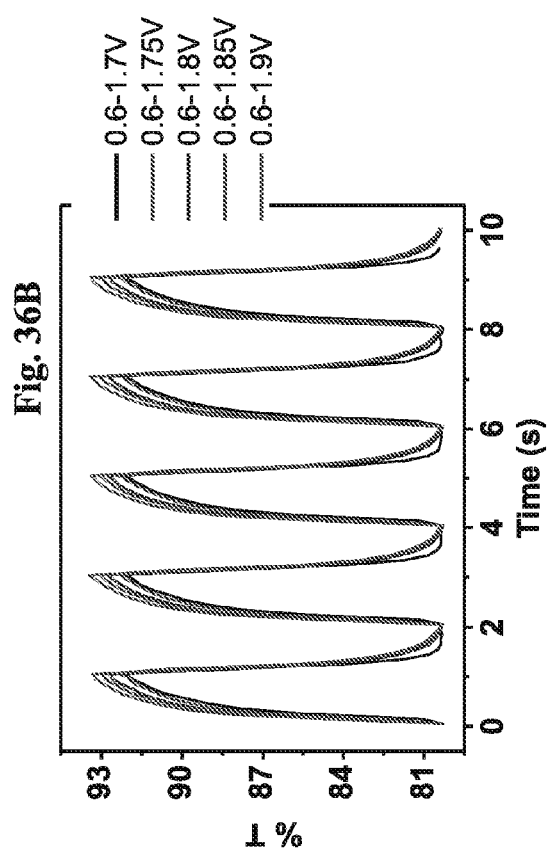
FIGS. 36A-36C show the effect of overpotential on the SEC of MA2SB (36A, RT), MA2DB (36B, RT) and MA2TB (36C, RT) (8 deposition cycles) at low switching time (pulse width 1 s), as immersed in a 0.1M TBAPF6 electrolyte solution using the modified ITO as working electrode, Pt wire as counter electrode and Ag/Ag$^+$ reference electrode.
Figure 36B:
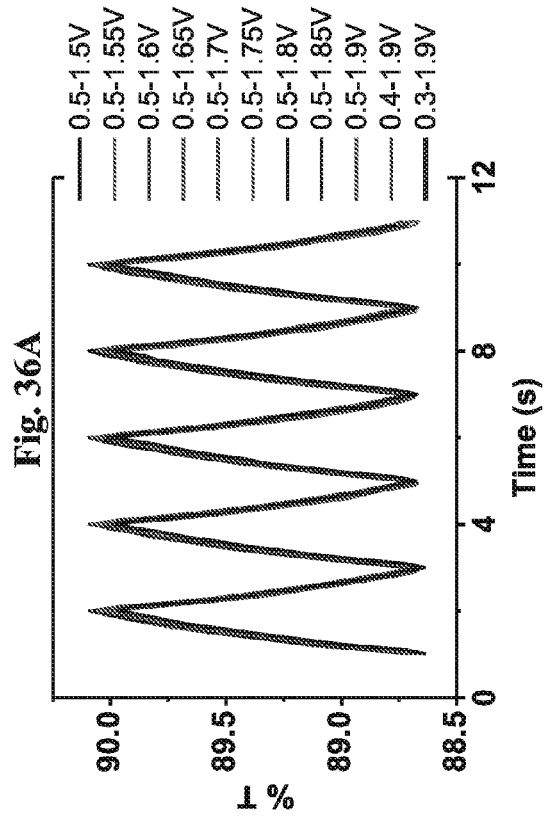
Figure 36C:
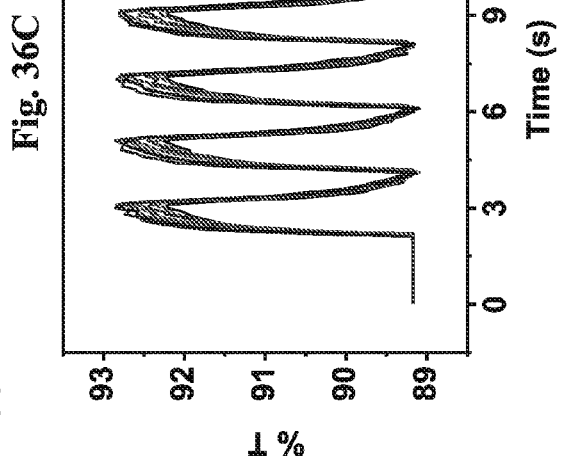
Figure 37B:
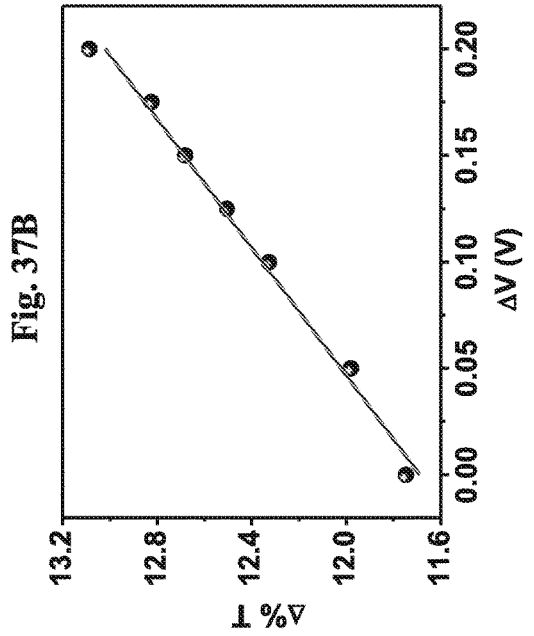
FIGS. 37A-37C show the effect of overpotential on the SEC of MA2SB (37A, RT), MA2DB (37B, RT, $R^2=0.99$) and MA2TB (37C, RT, $R^2>0.99$) (8 deposition cycles) at low switching time (pulse width 1 s), as immersed in a 0.1M TBAPF6 electrolyte solution using the modified ITO as working electrode, Pt wire as counter electrode and Ag/Ag$^+$ reference electrode.
Figure 37A:
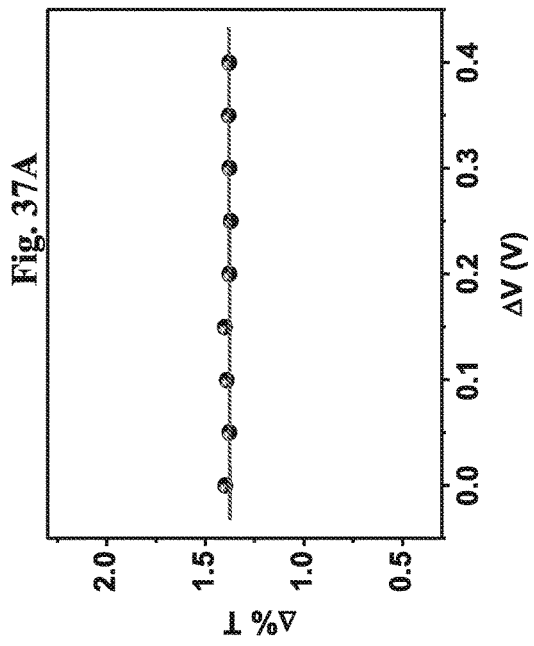
Figure 37C:
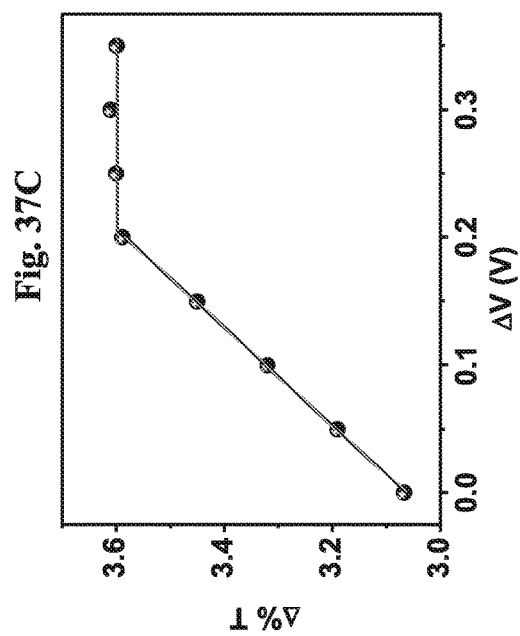
Figure 38E:
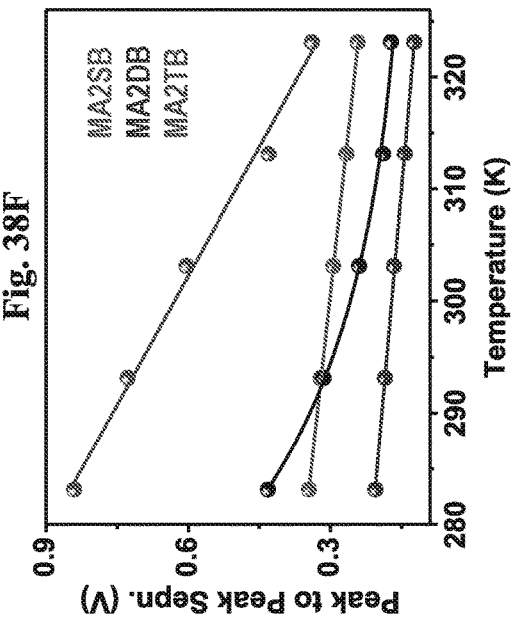
Figure 38F:
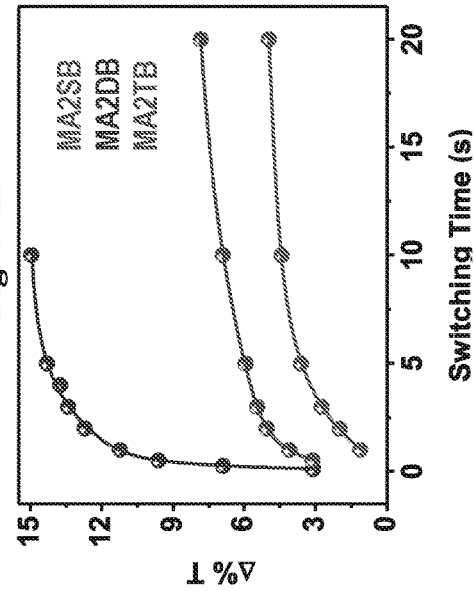
Figure 38G:
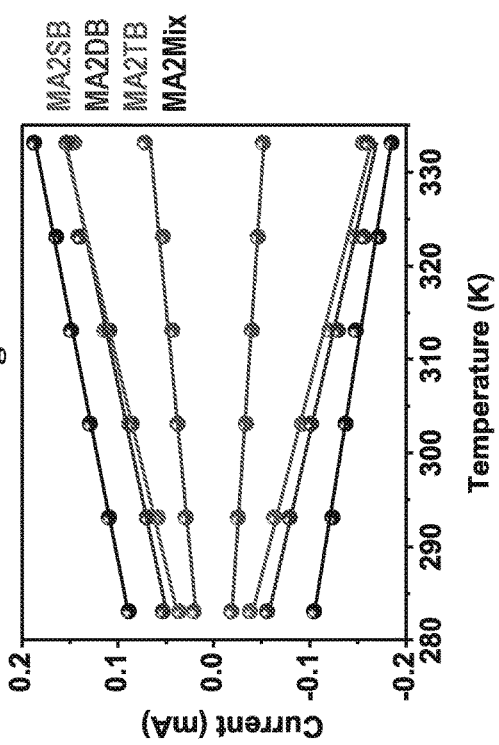
Figure 38H:
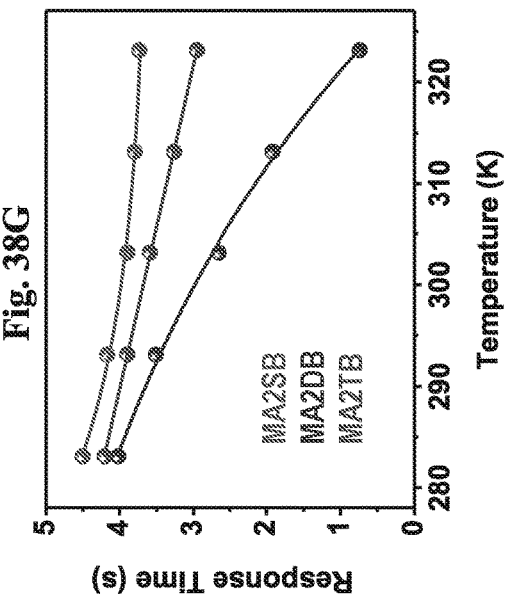

All these assemblies grew linearly and showed electrochemical switchings between colored (reduced) and transmissive (oxidized) states upon application of the right potential. Combined effect of the ligands and experimental parameters (temperature, switching time (=pulse width), overpotential, etc.) modulates the electro-optical signature of these assemblies. The assemblies showed better optical and electrochemical responses at higher temperature (up to 50° C., FIGS. 25-28) and on application of higher overpotential (FIGS. 29-31) (though the performance of MA2SB was not affected by overpotential, FIGS. 29A, 30A and 31A). Higher the temperature, smaller was the response time (FIGS. 32-33) for all the MAs. At higher switching times (=pulse width), the MAs showed superior electro-optical response (FIGS. 34-35). Application of overpotential at low temperature or smaller pulse width also resulted in better spectroelectrochemical properties (FIGS. 36-37).

Study 3. Stability and Coloration Efficiency of MA2DB Based Electrochromics

Figure 39A:
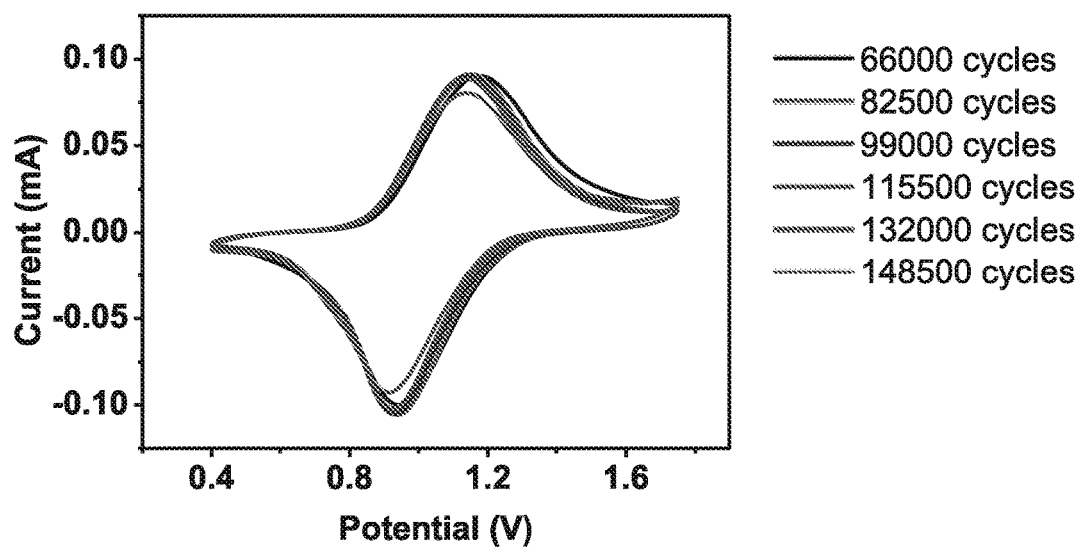
FIGS. 39A-39C show the electrochemical stability of MA2DB at 10° C. (39A) CV of MA2DB up to $1.485\times10^5$ switching cycles; (39B) Maximum current as in 39A vs. the number of switching cycles; (39C) SEC of MA2DB on ITO at 591 nm over a potential range of 0.55 to 1.45V with a 1 s pulse width. Each segment in 39C corresponds to the first five switching cycles in every interval. This multistep square-wave potential measurement was carried out using a 0.1 M Bu$_4$NPF$_6$/PC electrolyte solution.
Figure 39B:
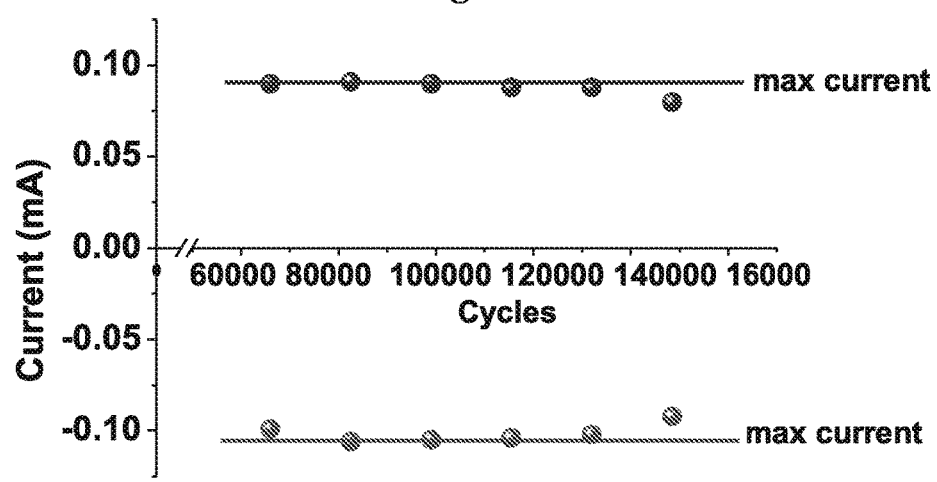
Figure 39C:
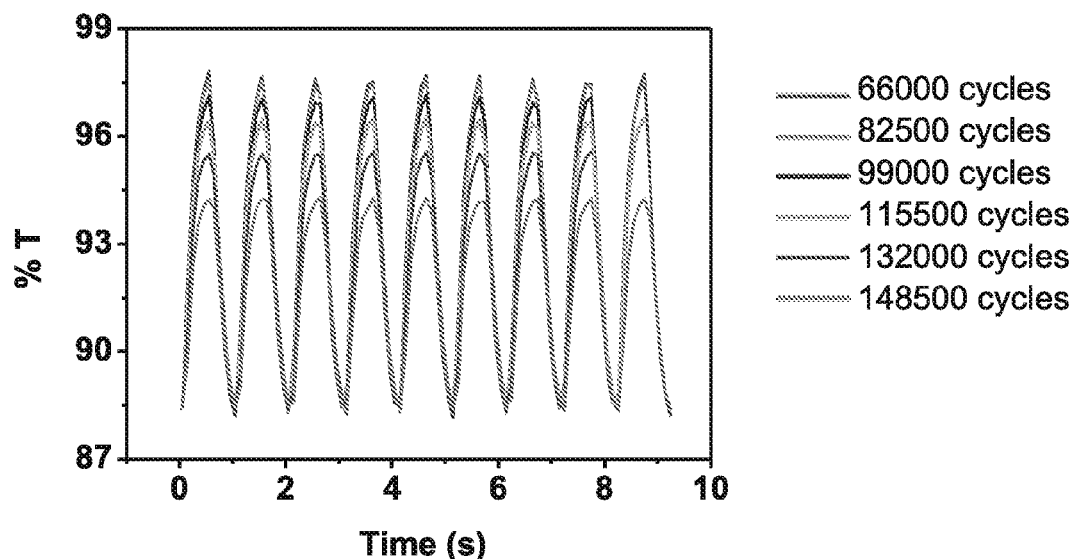
Figure 40A:
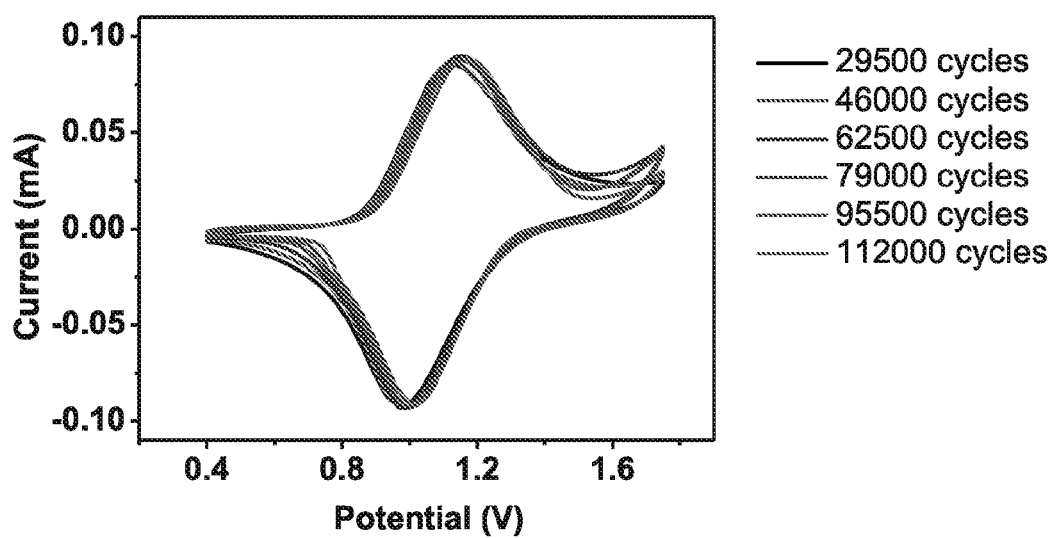
FIGS. 40A-40C show the electrochemical stability of MA2DB at 25° C. (40A) CV of MA2DB (23 nm thickness, 0.1 M TBAPF$_6$ in propylene carbonate, 100 mV/sec) up to $1.12\times10^5$ switching cycles; (40B) Maximum current as in 40A vs. the number of switching cycles; (40C) SEC of MA2DB on ITO at 591 nm over a potential range of 0.55 to 1.45V with a 1 s pulse width. Each segment in 40C corresponds to the first five switching cycles in every interval. This multistep square-wave potential measurement was carried out using a 0.1 M Bu$_4$NPF$_6$/PC electrolyte solution.
Figure 40B:
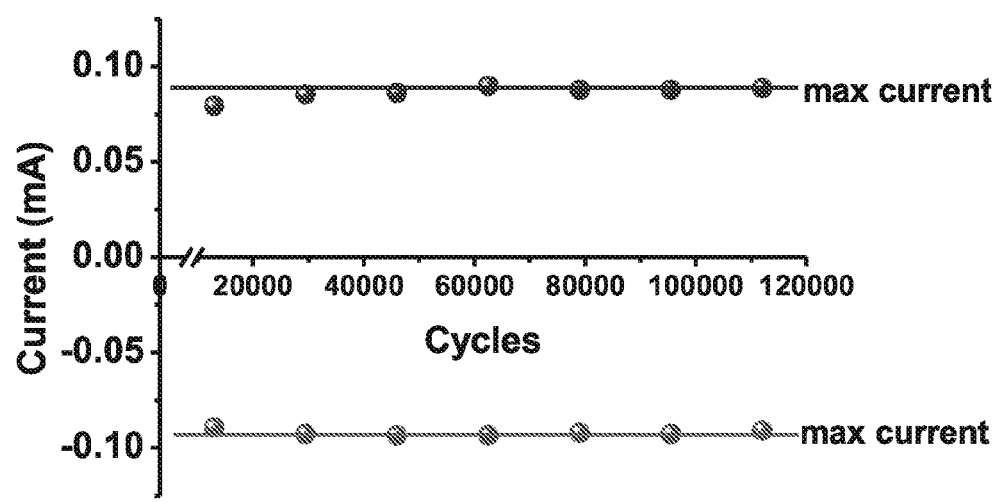
Figure 40C:
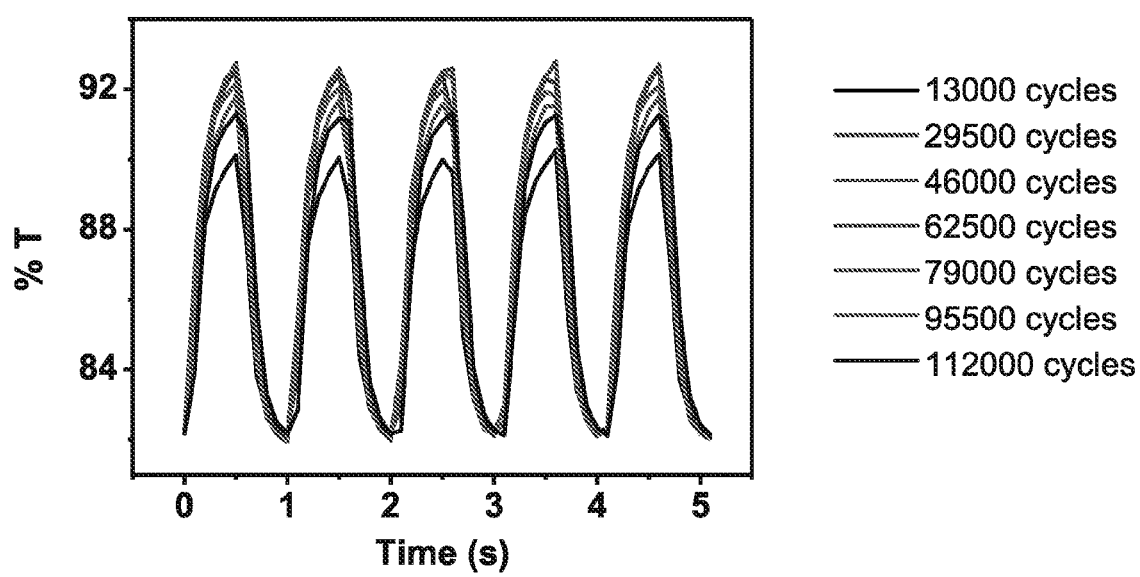
Figure 41A:
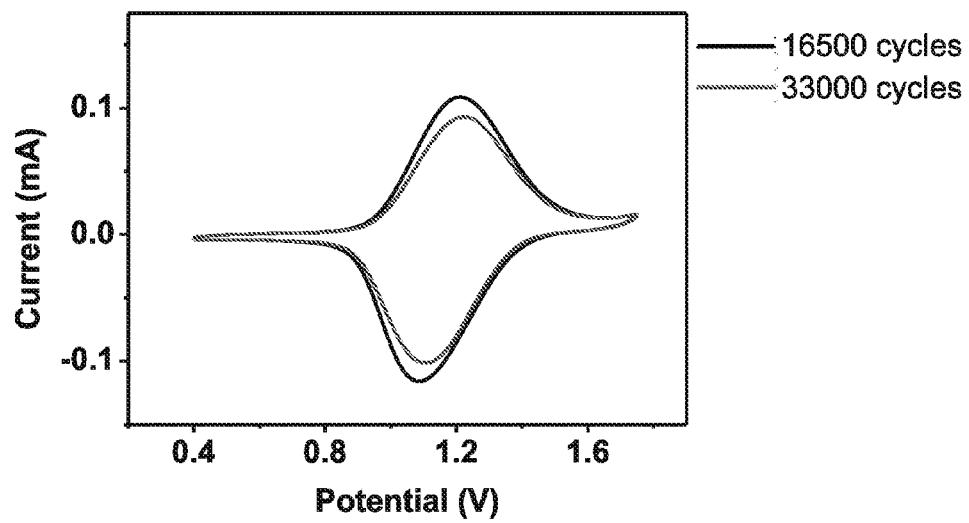
FIGS. 41A-41B show the electrochemical stability of MA2DB at 40° C. (41A) CV of MA2DB (23 nm thickness, 0.1 M TBAPF$_6$ in propylene carbonate, 100 mV/sec) up to $3.3\times10^4$ switching cycles; (41B) SEC of MA2DB on ITO at 591 nm over a potential range of 0.55 to 1.45V with a 1 s pulse width. Each segment in 41B corresponds to the first five switching cycles in every interval. This multistep square-wave potential measurement was carried out using a 0.1 M Bu$_4$NPF$_6$/PC electrolyte solution.
Figure 41B:
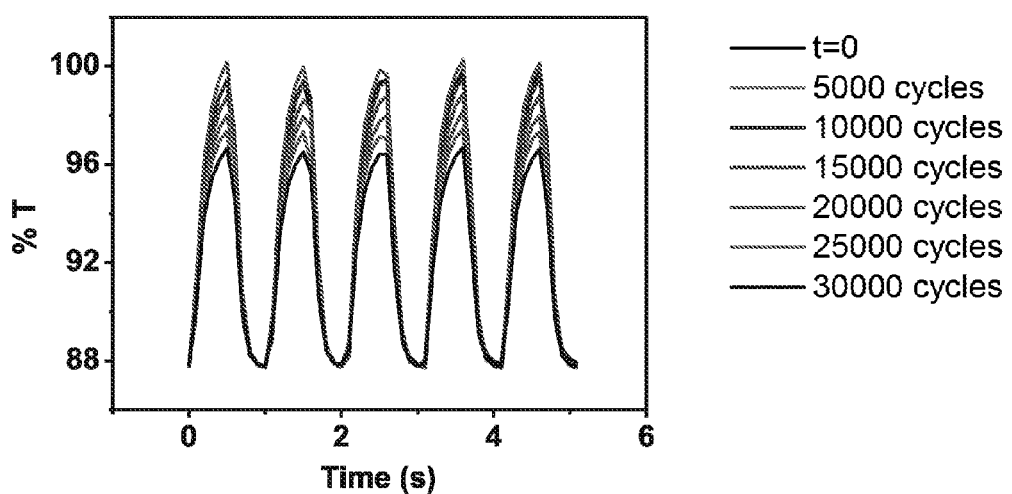
Figure 43A:
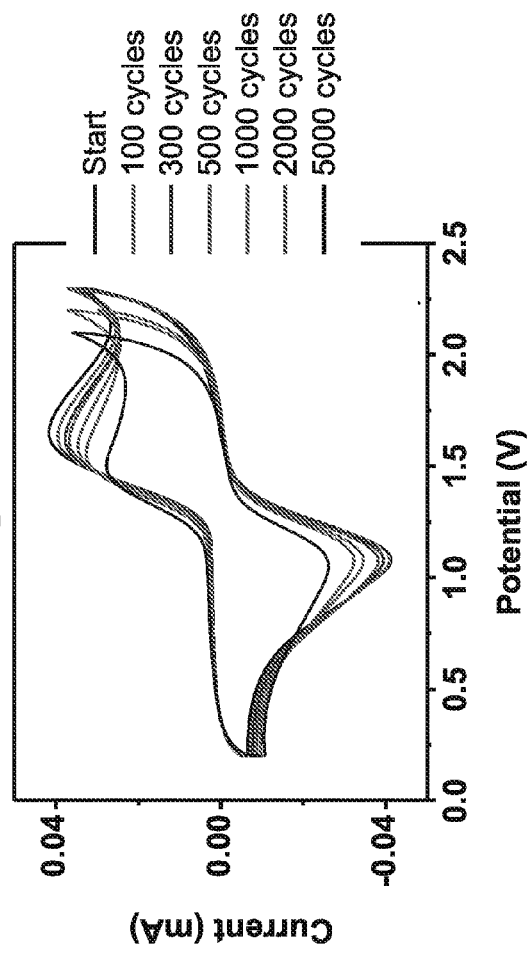
FIGS. 43A-43C show the electrochemical stability of MA2TB. (43A) CV of MA2DB up to 5000 switching cycles.
Figure 43C:
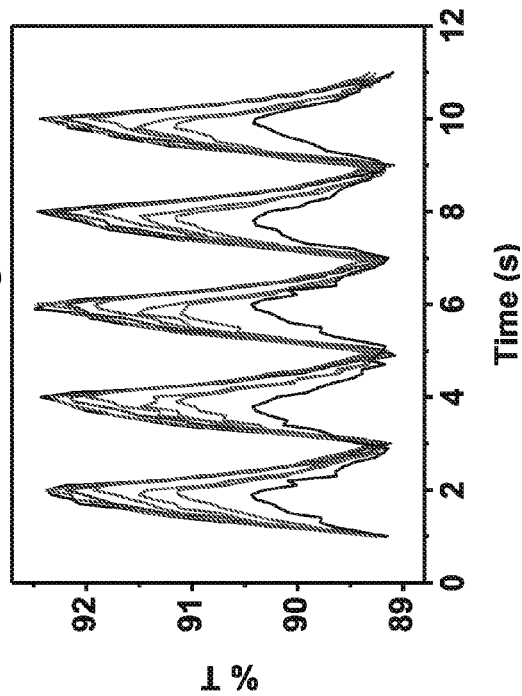
Figure 43B:
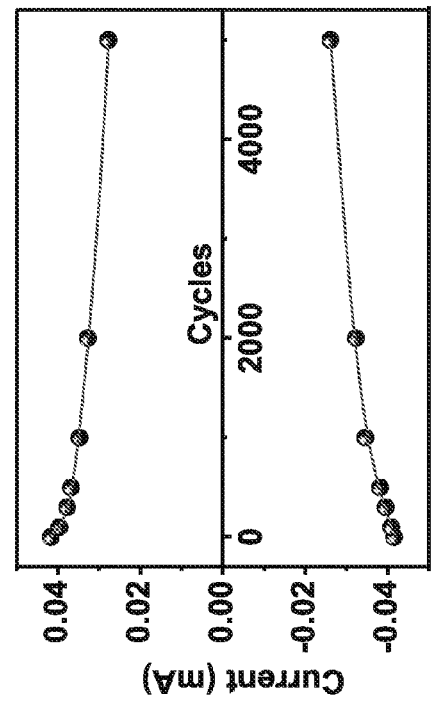

In this study, the effect of the molecular structure of the ligands in determining the stability and coloration efficiencies of the coordination based assemblies was determined. MA2DB was found to be electrochemically the most stable (FIGS. 40, 42 and 43) in the family and exhibited the highest coloration efficiency. MA2DB was electrochemically stable at lower temperature (10° C., FIG. 39) and at RT (FIG. 40), eventhough showed a slightly diminished stability at 40° C. (>86% after 33000 electrochemical switching cycles and >72% Δ% T after 30000 spectroelectrochemical switchings, FIG. 41). The thermal stability of MA1DB and MA2DB was also very high as no detectable loss in the intensity of MLCT band was observed after 50 days at 70° C. The coloration efficiency (see Study 1) for MA2DB (1488 $cm^2C^{-1}$) and MA1DB (955 $cm^2C^{-1}$) are amongst the highest reported values for such coordination based assemblies. The uniformity and color intensity of the assemblies was also found to be superlative (FIGS. 45-49).

APPENDIX

Scheme 1: Synthesis of ligands L1DB and L2DB

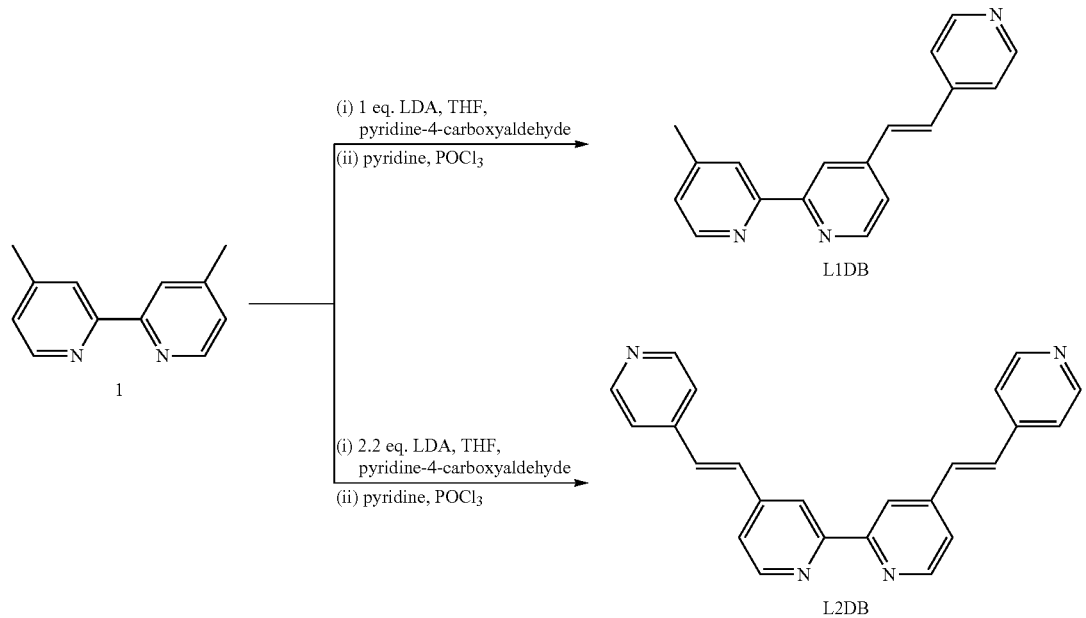

Scheme 2: Alternative synthesis of ligand L2DB
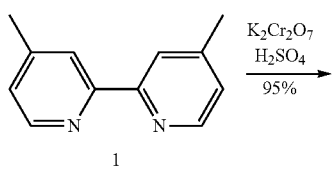
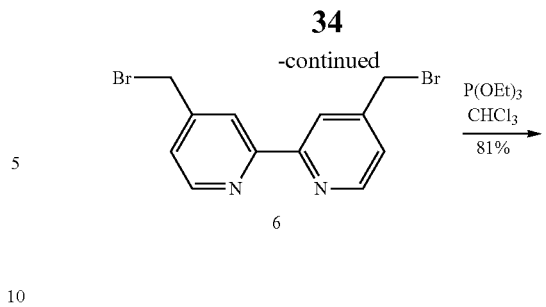
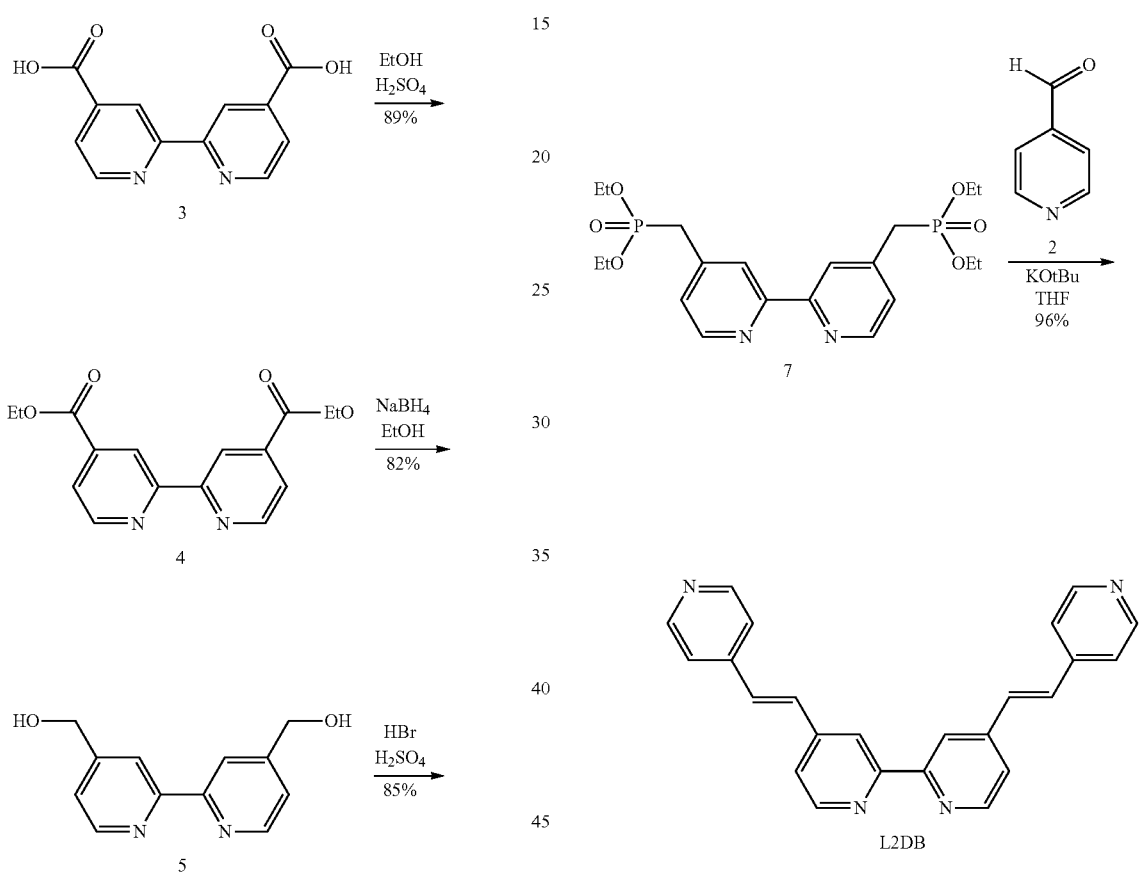
Scheme 3: Synthesis of ligands L2SB and L2TB
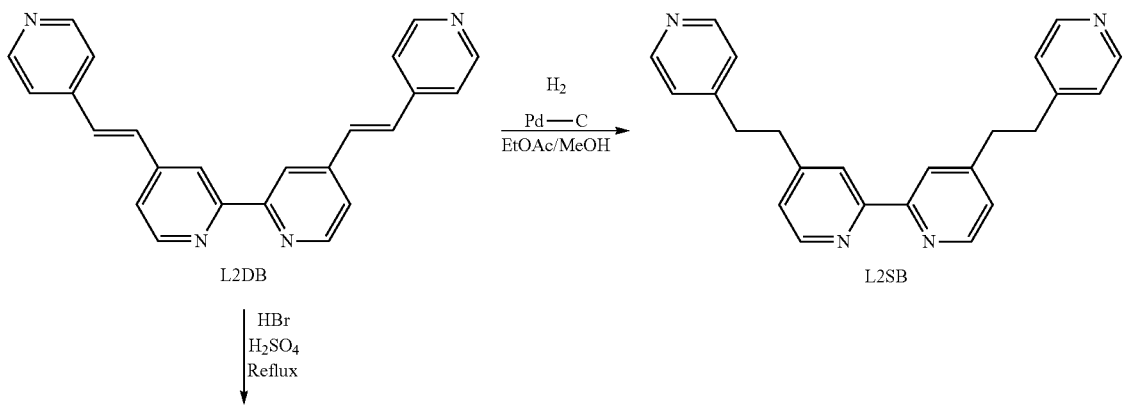

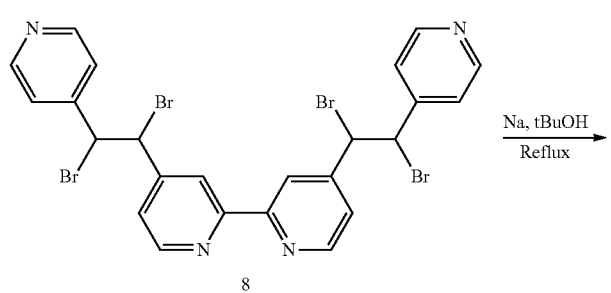

Structures: Specific Complexes of the General Formulas I and II

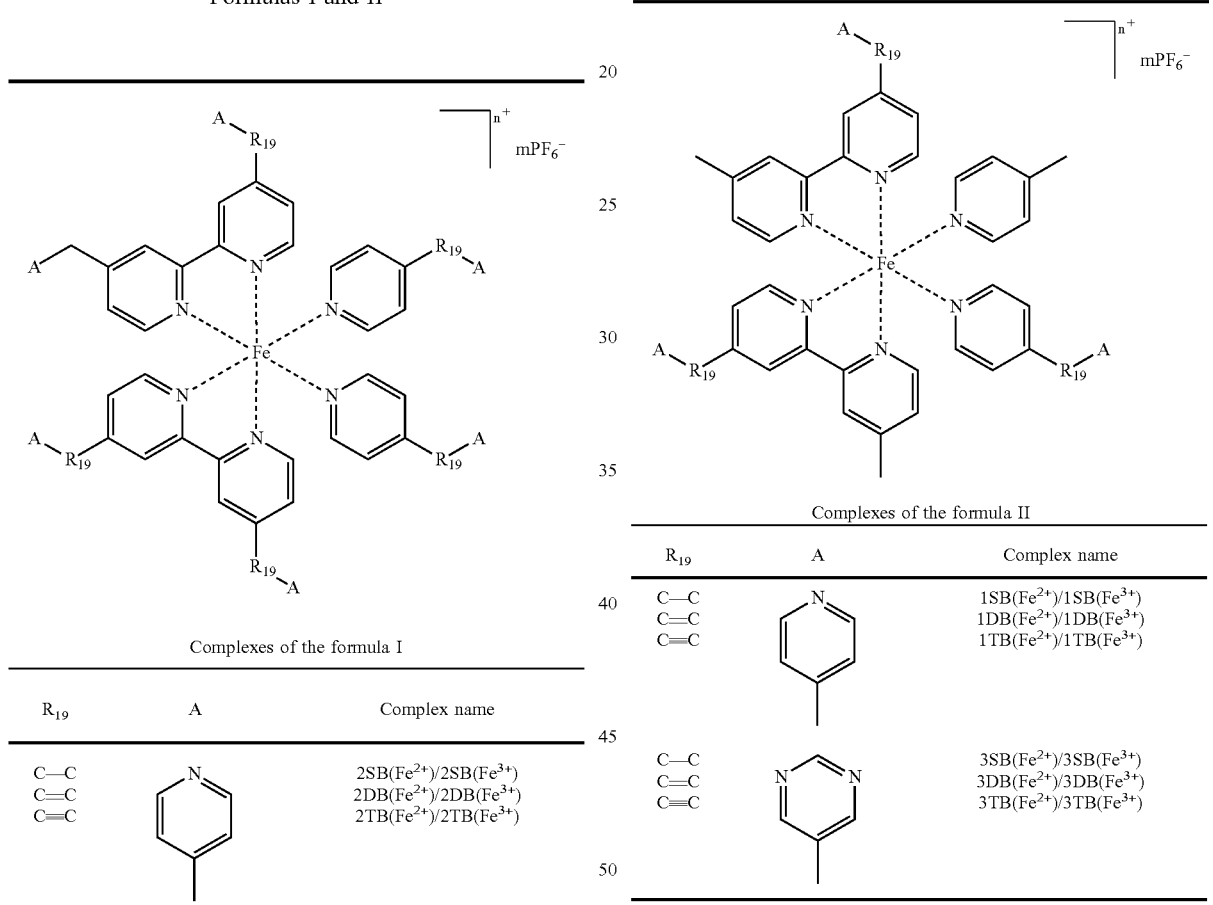

Complexes of the formula I

| $R_{19}$ | A | Complex name |
|---|---|---|
| C—C | 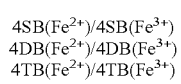 | 2SB(Fe$^{2+}$)/2SB(Fe$^{3+}$) |
| C=C | | 2DB(Fe$^{2+}$)/2DB(Fe$^{3+}$) |
| C≡C | | 2TB(Fe$^{2+}$)/2TB(Fe$^{3+}$) |
| C—C | 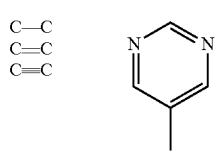 | 4SB(Fe$^{2+}$)/4SB(Fe$^{3+}$) |
| C=C | | 4DB(Fe$^{2+}$)/4DB(Fe$^{3+}$) |
| C≡C | | 4TB(Fe$^{2+}$)/4TB(Fe$^{3+}$) |

Complexes of the formula II

| $R_{19}$ | A | Complex name |
|---|---|---|
| C—C | pyridyl | 1SB(Fe$^{2+}$)/1SB(Fe$^{3+}$) |
| C=C | | 1DB(Fe$^{2+}$)/1DB(Fe$^{3+}$) |
| C≡C | | 1TB(Fe$^{2+}$)/1TB(Fe$^{3+}$) |
| C—C | pyrimidyl | 3SB(Fe$^{2+}$)/3SB(Fe$^{3+}$) |
| C=C | | 3DB(Fe$^{2+}$)/3DB(Fe$^{3+}$) |
| C≡C | | 3TB(Fe$^{2+}$)/3TB(Fe$^{3+}$) |

REFERENCES

Choudhury, J., Kaminker, R., Motiei, L., de Ruiter, G., Morozov, M., Lupo, F., Gulino, A., van der Boom, M. E., *J. Am. Chem. Soc.*, 2010, 132, 9295-9297

Coe, B. J., Fielden, J., Foxon, S. P., Brunschwig, B. S., Asselberghs, I., Clays, K., Samoc, A. Samoc, M., *J. Am. Chem. Soc.*, 2010, 132, 3496-3513 de Ruiter, G., Lahav, M., Keisar, H., van der Boom, M. E., *Angew. Chem., Int. Ed.*, 2013a, 52, 704-709 de Ruiter, G., Lahav, M., Evmenenko, G., Dutta, P., Cristaldi, D. A., Gulino, A., van der Boom, M. E., *J. Am. Chem. Soc.*, 2013b, 135, 16533-16544

Gillaizeau-Gauthier, I., Odobel, F., Alebbi, M., Argazzi, R., Costa, E., Bignozzi, C. A., Qu, P., Meyer, G. J., *Inorg. Chem.*, 2001, 40, 6073-6079

Motiei, L., Altman, M., Gupta, T., Lupo, F., Gulino, A., Evmenenko, G., Dutta, P., van der Boom, M. E., *J. Am. Chem. Soc.*, 2008, 130, 8913-8915

Nugent, P., Belmabkhout, Y., Burd, S. D., Cairns, A. J., Luebke, R., Forrest, K., Pham. T., Ma. S., Space, B., Wojtas, L., Eddaoudi, M., Zaworotko, M. J., *Nature*, 2013, 495, 80-84

Oki, A. R., Morgan, R. J., *Synthetic Commun.*, 1995, 25, 4093-4097

The invention claimed is:

1. A tris-bipyridyl complex of the general formula I:

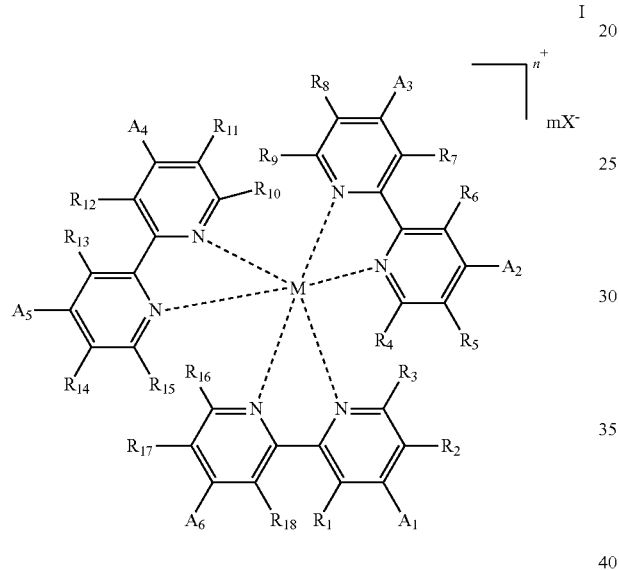

wherein

M is a transition metal selected from Mn, Fe, Co, Ni, Cu, Zn, Ti, V, Cr, Rh or Ir;

n is the formal oxidation state of the transition metal, wherein n is 0-6;

X is a counter anion such as Br⁻, Cl⁻, F⁻, I⁻, $PF_6^-$, $BF_4^-$, OH⁻, $ClO_4^-$, $SO_3^{2-}$, $SO_4^{2-}$, $CF_3COO^-$, CN⁻, alkylCOO⁻, arylCOO⁻, or a combination thereof;

m is a number ranging from 0 to 6;

$R_1$ to $R_{18}$ each independently is selected from H, halogen, —OH, —$N_3$, —$NO_2$, —CN, —$N(R_{20})_2$, —$CON(R_{20})_2$, —$COOR_{20}$, —$SR_{20}$, —$SO_3H$, —CH=CH-pyridyl, ($C_1$-$C_{10}$)alkyl, ($C_2$-$C_{10}$)alkenyl, ($C_2$-$C_{10}$)alkynyl, ($C_1$-$C_{10}$)alkoxy, cycloalkyl, heterocycloalkyl, aryl, heteroaryl, protected carboxyl, or protected amino, wherein said ($C_1$-$C_{10}$)alkyl, ($C_2$-$C_{10}$)alkenyl, ($C_2$-$C_{10}$)alkynyl, cycloalkyl, heterocycloalkyl, aryl and heteroaryl may optionally be substituted with halogen, —$OR_{20}$, —$COR_{20}$, —$COOR_{20}$, —$OCOOR_{20}$, —$OCON(R_{20})_2$, —($C_1$-$C_8$)alkylene-$COOR_{20}$, —CN, $N(R_{20})_2$, —$NO_2$, —$SR_{20}$, —($C_1$-$C_8$)alkyl, —O—($C_1$-$C_8$)alkyl, —$CON(R_{20})_2$, or —$SO_3H$;

$A_1$ to $A_6$ each independently is a group of the formula III or IV linked to the ring structure of the complex of general formula I via $R_{19}$

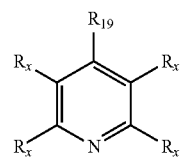

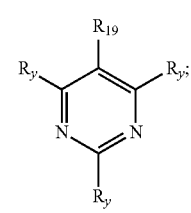

$R_{19}$ each independently is selected from C—C, C=C, C≡C, N=N, C=N, N=C, C—N, N—C, —COO—, —CONH—, —CON(OH)—, —$NR_{20}$—, —$Si(R_{20})_2$—, an alkylene optionally interrupted by one or more heteroatoms selected from O, S or N, phenylene, biphenylene, a peptide moiety consisting of 3 to 5 amino acid residues,

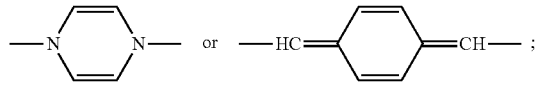

$R_x$ and $R_y$ each independently is selected from H, halogen, —OH, —$N_3$, —$NO_2$, —CN, —$N(R_{20})_2$, —$CON(R_{20})_2$, —$COOR_{20}$, —$SR_{20}$, —$SO_3H$, —CH=CH-pyridyl, ($C_1$-$C_{10}$)alkyl, ($C_2$-$C_{10}$)alkenyl, ($C_2$-$C_{10}$)alkynyl, ($C_1$-$C_{10}$)alkoxy, cycloalkyl, heterocycloalkyl, aryl, heteroaryl, protected carboxyl, or protected amino, wherein said ($C_1$-$C_{10}$)alkyl, ($C_2$-$C_{10}$)alkenyl, ($C_2$-$C_{10}$)alkynyl, cycloalkyl, heterocycloalkyl, aryl and heteroaryl may optionally be substituted with halogen, —$OR_{20}$, —$COR_{20}$, —$COOR_{20}$, —$OCOOR_{20}$, —$OCON(R_{20})_2$, —($C_1$-$C_8$)alkylene-$COOR_{20}$, —CN, $N(R_{20})_2$, —$NO_2$, —$SR_{20}$, —($C_1$-$C_8$)alkyl, —O—($C_1$-$C_8$)alkyl, —$CON(R_{20})_2$, or —$SO_3H$; and $R_{20}$ each independently is H, ($C_1$-$C_6$)alkyl or aryl.

2. The complex of claim 1, wherein $A_1$ to $A_6$ each independently is a group of the formula III, wherein $R_x$ is H, or of the formula IV, wherein $R_y$ is H.

3. The complex of claim 1, wherein $R_{19}$ each independently is C—C, C=C, C≡C, N=N, C=N, N=C, C—N, N—C, —COO—, —CONH—, —CON(OH)—, —$NR_{20}$—, —$Si(R_{20})_2$—, or an alkylene optionally interrupted by one or more heteroatoms selected from O, S or N, preferably C—C, C=C or C≡C.

4. The complex of claim 1, wherein $A_1$ to $A_6$ each is a group of the formula III wherein $R_x$ is H and $R_{19}$ is C—C, C=C or C≡C; or of the formula IV, wherein $R_y$ is H and $R_{19}$ is C—C, C=C or C≡C.

5. The complex of claim 1, wherein $R_1$ to $R_{18}$ each independently is H, halogen, —OH, —$N_3$, —$NO_2$, —CN, —$N(R_{20})_2$, —$SR_{20}$, —CH=CH-pyridyl, ($C_1$-$C_{10}$)alkyl, aryl, or heteroaryl, wherein said ($C_1$-$C_{10}$)alkyl, aryl and heteroaryl may optionally be substituted with halogen, —$OR_{20}$, —$COR_{20}$, —$COOR_{20}$, —$OCOOR_{20}$, —OCON($R_{20}$)$_2$, —($C_1$-$C_8$)alkylene-$COOR_{20}$, —CN, $N(R_{20})_2$, —$NO_2$, —$SR_{20}$, —($C_1$-$C_8$)alkyl, —O—($C_1$-$C_8$)alkyl, —$CON(R_{20})_2$, or —$SO_3H$; $A_1$ to $A_6$ each independently is a group of the formula III, wherein $R_x$ is H, or of the formula IV, wherein $R_y$ is H; $R_{19}$ each independently is C—C, C=C, C≡C, N=N, C=N, N=C, C—N, N—C, —COO—, —CONH—, —CON(OH)—, —NR$_{20}$—, —Si(R$_{20}$)$_2$—, or an alkylene optionally interrupted by one or more heteroatoms selected from O, S or N; and R$_{20}$ each is H.

6. The complex of claim 5, wherein $R_1$ to $R_{18}$ each is H; $A_1$ to $A_6$ each independently is a group of the formula III, wherein $R_x$ is H, or of the formula IV, wherein $R_y$ is H; and $R_{19}$ each independently is C—C, C=C or C≡C.

7. The complex of claim 6, wherein M is Fe; n and m each is 2 or 3; and $A_1$ to $A_6$ each is a group of the formula III, wherein $R_x$ is H and $R_{19}$ is C—C, C=C or C≡C.

8. The complex of claim 7, wherein X is $PF_6^-$; and (i) $R_{19}$ each is C—C, herein identified complex 2SB($Fe^{2+}$) or 2SB($Fe^{3+}$); (ii) $R_{19}$ each is C=C, herein identified complex 2DB($Fe^{2+}$) or 2DB($Fe^{3+}$); or (ii) $R_{19}$ each is C≡C, herein identified complex 2 TB($Fe^{2+}$) or 2 TB($Fe^{3+}$).

9. The complex of claim 6, wherein M is Fe; n and m each is 2 or 3; and $A_1$ to $A_6$ each is a group of the formula IV, wherein $R_y$ is H and $R_{19}$ is C—C, C=C or C≡C.

10. The complex of claim 9, wherein X is $PF_6^-$; and (i) $R_{19}$ each is C—C, herein identified complex 4SB($Fe^{2+}$) or 4SB($Fe^{3+}$); (ii) $R_{19}$ each is C=C, herein identified complex 4DB($Fe^{2+}$) or 4DB($Fe^{3+}$); or (ii) $R_{19}$ each is C≡C, herein identified complex 4TB($Fe^{2+}$) or 4TB($Fe^{3+}$).

11. An iron-based tris-bipyridyl complex of the general formula II:

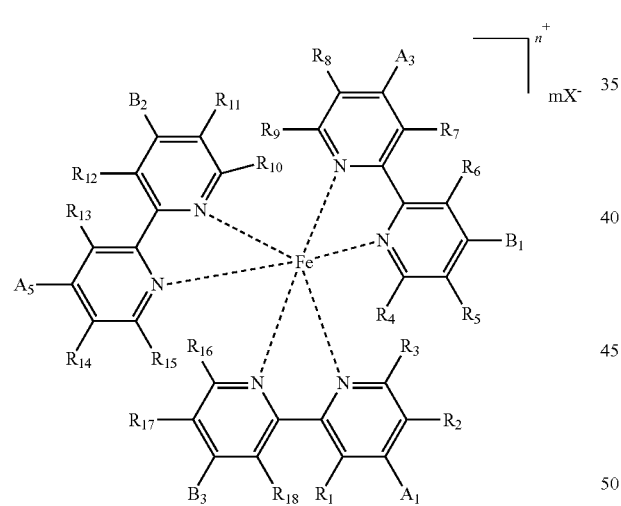

wherein
n is the formal oxidation state of the Fe, wherein n is 0-6;
X is a counter anion such as $Br^-$, $Cl^-$, $F^-$, $I^-$, $PF_6^-$, $BF_4^-$, $OH^-$, $ClO_4^-$, $SO_3^{2-}$, $SO_4^{2-}$, $CF_3COO^-$, $CN^-$, alkCOO$^-$, arylCOO$^-$, or a combination thereof;
m is a number ranging from 0 to 6;
$R_1$ to $R_{18}$ each independently is selected from H, halogen, —OH, —N$_3$, —NO$_2$, —CN, —N(R$_{20}$)$_2$, —CON(R$_{20}$)$_2$, —COOR$_{20}$, —SR$_{20}$, —SO$_3$H, —CH=CH-pyridyl, ($C_1$-$C_{10}$)alkyl, ($C_2$-$C_{10}$)alkenyl, ($C_2$-$C_{10}$)alkynyl, ($C_1$-$C_{10}$)alkoxy, cycloalkyl, heterocycloalkyl, aryl, heteroaryl, protected carboxyl, or protected amino, wherein said ($C_1$-$C_{10}$)alkyl, ($C_2$-$C_{10}$) alkenyl, ($C_2$-$C_{10}$)alkynyl, cycloalkyl, heterocycloalkyl, aryl and heteroaryl may optionally be substituted with halogen, —OR$_{20}$, —COR$_{20}$, —COOR$_{20}$, —OCOOR$_{20}$, —OCON(R$_{20}$)$_2$, —($C_1$-$C_8$)alkylene-COOR$_{20}$, —CN, N(R$_{20}$)$_2$, —NO$_2$, —SR$_{20}$, —($C_1$-$C_8$) alkyl, —O—($C_1$-$C_8$)alkyl, —CON(R$_{20}$)$_2$, or —SO$_3$H;
$A_1$, $A_3$ and $A_5$ each independently is a group of the formula III or IV linked to the ring structure of the complex of general formula II via $R_{19}$

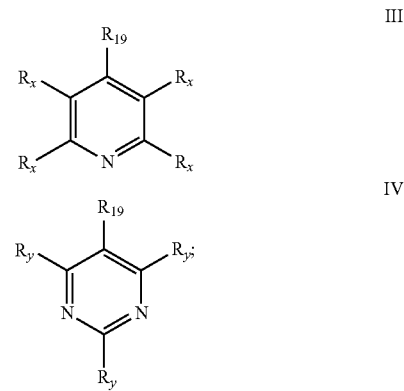

$R_{19}$ is selected from C—C, C=C, C≡C, N=N, C=N, N=C, C—N, N—C, —COO—, —CONH—, —CON (OH)—, —NR$_{20}$—, —Si(R$_{20}$)$_2$—, an alkylene optionally interrupted by one or more heteroatoms selected from O, S or N, phenylene, biphenylene, a peptide moiety consisting of 3 to 5 amino acid residues,

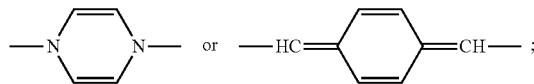

$R_x$ and $R_y$ each independently is selected from H, halogen, —OH, —N$_3$, —NO$_2$, —CN, —N(R$_{20}$)$_2$, —CON(R$_{20}$)$_2$, —COOR$_{20}$, —SR$_{20}$, —SO$_3$H, —CH=CH-pyridyl, ($C_1$-$C_{10}$)alkyl, ($C_2$-$C_{10}$)alkenyl, ($C_2$-$C_{10}$)alkynyl, ($C_1$-$C_{10}$)alkoxy, cycloalkyl, heterocycloalkyl, aryl, heteroaryl, protected carboxyl, or protected amino, wherein said ($C_1$-$C_{10}$)alkyl, ($C_2$-$C_{10}$) alkenyl, ($C_2$-$C_{10}$)alkynyl, cycloalkyl, heterocycloalkyl, aryl and heteroaryl may optionally be substituted with halogen, —OR$_{20}$, —COR$_{20}$, —COOR$_{20}$, —OCOOR$_{20}$, —OCON(R$_{20}$)$_2$, —($C_1$-$C_8$)alkylene-COOR$_{20}$, —CN, N(R$_{20}$)$_2$, —NO$_2$, —SR$_{20}$, —($C_1$-$C_8$) alkyl, —O—($C_1$-$C_8$)alkyl, —CON(R$_{20}$)$_2$, or —SO$_3$H;
$B_1$ to $B_3$ each independently is selected from H, halogen, —OH, —N$_3$, —NO$_2$, —CN, —N(R$_{20}$)$_2$, —CON(R$_{20}$)$_2$, —COOR$_{20}$, —SR$_{20}$, —SO$_3$H, —CH=CH-pyridyl, ($C_1$-$C_{10}$)alkyl, ($C_2$-$C_{10}$)alkenyl, ($C_2$-$C_{10}$)alkynyl, ($C_1$-$C_{10}$)alkoxy, cycloalkyl, heterocycloalkyl, aryl, heteroaryl, protected carboxyl, or protected amino, wherein said ($C_1$-$C_{10}$)alkyl, ($C_2$-$C_{10}$) alkenyl, ($C_2$-$C_{10}$)alkynyl, cycloalkyl, heterocycloalkyl, aryl and heteroaryl may optionally be substituted with halogen, —OR$_{20}$, —COR$_{20}$, —COOR$_{20}$, —OCOOR$_{20}$, —OCON(R$_{20}$)$_2$, —($C_1$-$C_8$)alkylene-COOR$_{20}$, —CN, N(R$_{20}$)$_2$, —NO$_2$, —SR$_{20}$—($C_1$-$C_8$) alkyl, —O—($C_1$-$C_8$)alkyl, —CON(R$_{20}$)$_2$, or —SO$_3$H; and
$R_{20}$ each independently is H, ($C_1$-$C_6$)alkyl or aryl.

12. The complex of claim 11, wherein $A_1$, $A_3$ and $A_5$ each independently is a group of the formula III, wherein $R_x$ is H, or of the formula IV, wherein $R_y$ is H.

13. The complex of claim 11, wherein $R_{19}$ each independently is C—C, C=C, C≡C, N=N, C=N, N=C, C—N, N—C, —COO—, —CONH—, —CON(OH)—, —NR$_{20}$—, —Si(R$_{20}$)$_2$—, or an alkylene optionally interrupted by one or more heteroatoms selected from O, S or N, preferably C—C, C=C or C≡C.

14. The complex of claim 11, wherein $A_1$, $A_3$ and $A_5$ each is a group of the formula III, wherein $R_x$ is H and $R_{19}$ is C—C, C=C or C≡C; or of the formula IV, wherein $R_y$ is H and $R_{19}$ is C—C, C=C or C≡C.

15. The complex of claim 11, wherein $R_1$ to $R_{18}$ each independently is H, halogen, —OH, —N$_3$, —NO$_2$, —CN, —N(R$_{20}$)$_2$, —SR$_{20}$, —CH=CH-pyridyl, (C$_1$-C$_{10}$)alkyl, aryl, or heteroaryl, wherein said (C$_1$-C$_{10}$)alkyl, aryl and heteroaryl may optionally be substituted with halogen, —OR$_{20}$, —COR$_{20}$, —COOR$_{20}$, —OCOOR$_{20}$, —OCON(R$_{20}$)$_2$, —(C$_1$-C$_8$)alkylene-COOR$_{20}$, —CN, N(R$_{20}$)$_2$, —NO$_2$, —SR$_{20}$, —(C$_1$-C$_8$)alkyl, —O—(C$_1$-C$_8$)alkyl, —CON(R$_{20}$)$_2$, or —SO$_3$H; $A_1$, $A_3$ and $A_5$ each independently is a group of the formula III, wherein $R_x$ is H, or of the formula IV, wherein $R_y$ is H; and $R_{19}$ each independently is C—C, C=C, C≡C, N=N, C=N, N=C, C—N, N—C, —COO—, —CONH—, —CON(OH)—, —NR$_{20}$—, —Si(R$_{20}$)$_2$—, or an alkylene optionally interrupted by one or more heteroatoms selected from O, S or N; $B_1$ to $B_3$ each independently is H, halogen, —OH, —N$_3$, —NO$_2$, —CN, —N(R$_{20}$)$_2$, —SR$_{20}$, —CH=CH— pyridyl, (C$_1$-C$_{10}$)alkyl, aryl, or heteroaryl, wherein said (C$_1$-C$_{10}$)alkyl, aryl and heteroaryl may optionally be substituted with halogen, —OR$_{20}$, —COR$_{20}$, —COOR$_{20}$, —OCOOR$_{20}$, —OCON(R$_{20}$)$_2$, —(C$_1$-C$_8$)alkylene-COOR$_{20}$, —CN, N(R$_{20}$)$_2$, —NO$_2$, —SR$_{20}$, —(C$_1$-C$_8$)alkyl, —O—(C$_1$-C$_8$)alkyl, —CON(R$_{20}$)$_2$, or —SO$_3$H; and $R_{20}$ each is H.

16. The complex of claim 15, wherein $R_1$ to $R_{18}$ each is H; $A_1$, $A_3$ and $A_5$ each independently is a group of the formula III, wherein $R_x$ is H, or of the formula IV, wherein $R_y$ is H; $R_{19}$ each independently is C—C, C=C or C≡C; and $B_1$ to $B_3$ each is (C$_1$-C$_4$)alkyl, preferably methyl or ethyl.

17. The complex of claim 16, wherein $A_1$, $A_3$ and $A_5$ each is a group of the formula III, wherein $R_x$ is H and $R_{19}$ is C—C, C=C or C≡C; and $B_1$ to $B_3$ each is methyl.

18. The complex of claim 17, wherein X is PF$_6^-$; n and m each is 2 or 3; and (i) $R_{19}$ each is C—C, herein identified complex 1SB(Fe$^{2+}$) or 1SB(Fe$^{3+}$); (ii) $R_{19}$ each is C=C, herein identified complex 1DB(Fe$^{2+}$) or 1DB(Fe$^{3+}$); or (ii) $R_{19}$ each is C≡C, herein identified complex 1TB(Fe$^{2+}$) or 1TB(Fe$^{3+}$).

19. The complex of claim 16, wherein $A_1$, $A_3$ and $A_5$ each is a group of the formula IV, wherein $R_y$ is H and $R_{19}$ is C=C; and $B_1$ to $B_3$ each is methyl.

20. The complex of claim 19, wherein X is PF$_6^-$; n and m each is 2 or 3; and (i) $R_{19}$ each is C—C, herein identified complex 3SB(Fe$^{2+}$) or 3SB(Fe$^{3+}$); (ii) $R_{19}$ each is C=C, herein identified complex 3DB(Fe$^{2+}$) or 3DB(Fe$^{3+}$); or (ii) $R_{19}$ each is C≡C, herein identified complex 3TB(Fe$^{2+}$) or 3TB(Fe$^{3+}$).

21. A device comprising a substrate having an electrically conductive surface and a layered structure disposed thereon, said layered structure comprising at least one redox-active compound configured to have a predetermined oxidation state being changeable upon subjecting said layered structure to an electric field,
wherein exposure of said device to a potential change causes reversible electron transfer, which results in a change in the electrochromic properties of said layered structure with high coloration efficiency, said device having high electrochemical stability when repeatedly exposed to a potential change,
wherein said redox-active compound each independently is a tris-bipyridyl complex of claim 1.

22. The device of claim 21, wherein said coloration efficiency is higher than 500 cm$^2$C$^{-1}$, preferably higher than 800 cm$^2$C$^{-1}$, more preferably higher than 1000 cm$^2$C$^{-1}$.

23. The device of claim 21, wherein said substrate comprises glass, a doped glass, indium tin oxide (ITO)-coated glass, transparent conductive oxide, silicon, a doped silicon, Si(100), Si(111), SiO$_2$, SiH, silicon carbide mirror, quartz, a metal, metal oxide, a mixture of metal and metal oxide, group IV elements, mica, a polymer such as polyacrylamide and polystyrene, a plastic, a zeolite, a clay, wood, a membrane, an optical fiber, a ceramic, a metalized ceramic, an alumina, an electrically-conductive material, a semiconductor, steel or a stainless steel and wherein said substrate is in the form of sheets, plates, columns, beads, microparticles, sub-microparticles, nanoparticles, quantum dots, metal-organic framework, or nanotubes and wherein said substrate is optically transparent to the ultraviolet (UV), infrared (IR), near-IR (NIR) and/or visible spectral ranges.

24. The device of claim 21, wherein said layered structure comprises (i) a monolayer of either one redox-active compound or two or more redox-active compounds, said redox-active compounds having identical or different metals; or (ii) a plurality of layers each comprising either one redox-active compound or two or more redox-active compounds, said redox-active compounds having identical or different metals.

25. The device of claim 24, wherein said layered structure comprises a monolayer of either one redox-active compound or two or more redox-active compounds, or a plurality of layers each comprising either one redox-active compound or two or more redox-active compounds, said redox-active compound each independently is:
a tris-bipyridyl complex of the general formula I in claim 1, wherein M is Fe; n and m each is 2 or 3; $R_1$ to $R_{18}$ each is H; and $A_1$ to $A_6$ each is a group of the formula III, wherein $R_x$ is H and $R_{19}$ is C—C, C=C or C≡C, or a group of the formula IV, wherein $R_y$ is H and $R_{19}$ is C—C, C=C or C≡C.

26. The device of claim 25, wherein said redox-active compound each independently is a tris-bipyridyl complex of the general formula I or II, wherein X is PF$_6^-$.

27. The device of claim 21, for use in smart windows, electrochromic windows, smart mirrors, optical filters, frequency doubling devices, optical switches, modulators, spatial light modulators, phase masks, data transfer devices, data storage devices, pulse shapers, optical processors, electrochromic display devices, smart papers, electrochromic goggles, electrochromic helmets, electrochromic paints, or visors.

28. The device of claim 27, for use in smart windows or electrochromic windows, wherein said layered structure comprises a plurality of layers each comprising either one redox-active compound or two or more redox-active compounds, said redox-active compound each independently is:
a tris-bipyridyl complex of the general formula I in claim 1, wherein M is Fe; n and m each is 2 or 3; $R_1$ to $R_{18}$ each is H; and $A_1$ to $A_6$ each is a group of the formula III, wherein $R_x$ is H and $R_{19}$ is C—C, C=C or C≡C, or a group of the formula IV, wherein $R_y$ is H and $R_{19}$ is C—C, C=C or C≡C.

29. The device of claim 28, wherein said redox-active compound each independently is a tris-bipyridyl complex of the general formula I or II, wherein X is PF$_6^-$.

30. A memory device comprising a substrate having an electrically conductive surface and a layered structure disposed thereon, said layered structure comprising at least one redox-active compound configured to have at least one a predetermined electronic property, including at least one of electrodensity and oxidation state, said predetermined electronic property being changeable upon subjecting said layered structure to an electric field,
wherein said redox-active compound each independently is a tris-bipyridyl complex of claim 1.

31. A device comprising a substrate having an electrically conductive surface and a layered structure disposed thereon, said layered structure comprising at least one redox-active compound configured to have a predetermined oxidation state being changeable upon subjecting said layered structure to an electric field,
wherein exposure of said device to a potential change causes reversible electron transfer, which results in a change in the electrochromic properties of said layered structure with high coloration efficiency, said device having high electrochemical stability when repeatedly exposed to a potential change,
wherein said redox-active compound each independently is a tris-bipyridyl complex of claim 11.

32. The device of claim 31, wherein said coloration efficiency is higher than 500 $cm^2C^{-1}$, preferably higher than 800 $cm^2C^{-1}$, more preferably higher than 1000 $cm^2C^{-1}$.

33. The device of claim 31, wherein said substrate comprises glass, a doped glass, indium tin oxide (ITO)-coated glass, transparent conductive oxide, silicon, a doped silicon, Si(100), Si(111), $SiO_2$, SiH, silicon carbide mirror, quartz, a metal, metal oxide, a mixture of metal and metal oxide, group IV elements, mica, a polymer such as polyacrylamide and polystyrene, a plastic, a zeolite, a clay, wood, a membrane, an optical fiber, a ceramic, a metalized ceramic, an alumina, an electrically-conductive material, a semiconductor, steel or a stainless steel and wherein said substrate is in the form of sheets, plates, columns, beads, microparticles, sub-microparticles, nanoparticles, quantum dots, metal-organic framework, or nanotubes and wherein said substrate is optically transparent to the ultraviolet (UV), infrared (IR), near-IR (NIR) and/or visible spectral ranges.

34. The device of claim 31, wherein said layered structure comprises (i) a monolayer of either one redox-active compound or two or more redox-active compounds, said redox-active compounds having identical or different metals; or (ii) a plurality of layers each comprising either one redox-active compound or two or more redox-active compounds, said redox-active compounds having identical or different metals.

35. The device of claim 34, wherein said layered structure comprises a monolayer of either one redox-active compound or two or more redox-active compounds, or a plurality of layers each comprising either one redox-active compound or two or more redox-active compounds, said redox-active compound each independently is:
a tris-bipyridyl complex of the general formula II in claim 11, wherein n and m each is 2 or 3; $R_1$ to $R_{18}$ each is H; $A_1$, $A_3$ and $A_5$ each is a group of the formula III, wherein $R_x$ is H and $R_{19}$ is C—C, C=C or C≡C, or a group of the formula IV, wherein $R_y$ is H and $R_{19}$ is C—C, C=C or C≡C; and $B_1$ to $B_3$ each is methyl.

36. The device of claim 35, wherein said redox-active compound each independently is a tris-bipyridyl complex of the general formula I or II, wherein X is $PF_6^-$.

37. The device of claim 31, for use in smart windows, electrochromic windows, smart mirrors, optical filters, frequency doubling devices, optical switches, modulators, spatial light modulators, phase masks, data transfer devices, data storage devices, pulse shapers, optical processors, electrochromic display devices, smart papers, electrochromic goggles, electrochromic helmets, electrochromic paints, or visors.

38. The device of claim 37, for use in smart windows or electrochromic windows, wherein said layered structure comprises a plurality of layers each comprising either one redox-active compound or two or more redox-active compounds, said redox-active compound each independently is:
a tris-bipyridyl complex of the general formula II in claim 11, wherein n and m each is 2 or 3; $R_1$ to $R_{18}$ each is H; $A_1$, $A_3$ and $A_5$ each is a group of the formula III, wherein $R_x$ is H and $R_{19}$ is C—C, C=C or C≡C, or a group of the formula IV, wherein $R_y$ is H and $R_{19}$ is C—C, C=C or C≡C; and $B_1$ to $B_3$ each is methyl.

39. The device of claim 31, wherein said redox-active compound each independently is a tris-bipyridyl complex of the general formula I or II, wherein X is $PF_6^-$.

40. A memory device comprising a substrate having an electrically conductive surface and a layered structure disposed thereon, said layered structure comprising at least one redox-active compound configured to have at least one a predetermined electronic property, including at least one of electrodensity and oxidation state, said predetermined electronic property being changeable upon subjecting said layered structure to an electric field,
wherein said redox-active compound each independently is a tris-bipyridyl complex of claim 11.

* * * * *